US007405198B2

(12) United States Patent
DeFrees et al.

(10) Patent No.: US 7,405,198 B2
(45) Date of Patent: Jul. 29, 2008

(54) GLYCOPEGYLATED ERYTHROPOIETIN

(75) Inventors: Shawn DeFrees, North Wales, PA (US); Robert J. Bayer, San Diego, CA (US); David A. Zopf, Wayne, PA (US)

(73) Assignee: Neose Technologies, Inc., Horsham, PA (US)

(*) Notice: Subject to any disclaimer, the term of this patent is extended or adjusted under 35 U.S.C. 154(b) by 0 days.

(21) Appl. No.: 10/997,405

(22) Filed: Nov. 24, 2004

(65) Prior Publication Data

US 2005/0143292 A1 Jun. 30, 2005

Related U.S. Application Data

(60) Provisional application No. 60/623,387, filed on Oct. 29, 2004, provisional application No. 60/614,518, filed on Sep. 29, 2004, provisional application No. 60/592,744, filed on Jul. 29, 2004, provisional application No. 60/590,573, filed on Jul. 23, 2004, provisional application No. 60/555,504, filed on Mar. 22, 2004, provisional application No. 60/539,387, filed on Jan. 26, 2004, provisional application No. 60/524,989, filed on Nov. 24, 2003.

(51) Int. Cl.
*A61K 38/16* (2006.01)
*C07K 1/00* (2006.01)

(52) U.S. Cl. .......................................... 514/8; 530/395
(58) Field of Classification Search ....................... None
See application file for complete search history.

(56) References Cited

U.S. PATENT DOCUMENTS

| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts et al. |
| 4,412,989 A | 11/1983 | Iwashita et al. |
| 4,414,147 A | 11/1983 | Klibanov |
| 4,496,689 A | 1/1985 | Mitra |
| 4,806,595 A | 2/1989 | Noishiki et al. |
| 4,925,796 A | 5/1990 | Bergh et al. |
| 5,154,924 A | 10/1992 | Friden |
| 5,182,107 A | 1/1993 | Friden |
| 5,352,670 A | 10/1994 | Venot |
| 5,374,541 A | 12/1994 | Wong |
| 5,405,753 A | 4/1995 | Brossmer |
| 5,432,059 A | 7/1995 | Bean |
| 5,527,527 A | 6/1996 | Friden |
| 5,545,553 A | 8/1996 | Gotschlich |
| 5,614,184 A | 3/1997 | Sytkowski et al. |
| 5,621,039 A | 4/1997 | Hallahan et al. |
| 5,672,683 A | 9/1997 | Friden et al. |
| 5,716,812 A | 2/1998 | Withers et al. |
| 5,728,554 A | 3/1998 | Bayer et al. |
| 5,833,988 A | 11/1998 | Friden |
| 5,834,251 A | 11/1998 | Maras et al. |
| 5,876,980 A | 3/1999 | DeFrees et al. |
| 5,922,577 A | 7/1999 | Defrees et al. |
| 5,932,462 A | 8/1999 | Harris et al. |
| 5,969,040 A | 10/1999 | Hallahan et al. |
| 5,977,307 A | 11/1999 | Friden |
| 6,015,555 A | 1/2000 | Friden |
| 6,030,815 A | 2/2000 | DeFrees et al. |
| 6,037,452 A | 3/2000 | Minamino et al. |
| 6,057,292 A | 5/2000 | Cunningham et al. |
| 6,096,512 A | 8/2000 | Elhammer et al. |
| 6,166,183 A | 12/2000 | Ishikawa et al. |
| 6,183,738 B1 | 2/2001 | Clark |
| 6,692,931 B1 | 2/2004 | Reutter et al. |
| 7,202,208 B2 * | 4/2007 | Papadimitriou ................. 514/8 |
| 2002/0037841 A1 | 3/2002 | Papadimitriou |
| 2002/0115833 A1 | 8/2002 | Burg et al. |
| 2002/0137134 A1 | 9/2002 | Gerngross et al. |

FOREIGN PATENT DOCUMENTS

| EP | 0605963 A2 | 7/1994 |
| WO | WO 87/00056 | 1/1987 |
| WO | WO 89/10134 A1 | 11/1989 |
| WO | WO 90/07572 A1 | 7/1990 |

(Continued)

OTHER PUBLICATIONS

Cointe et al, Unusual N-glycosylation of a recombinant human erythropoietin expressed in a human lymphoblastoid cell line does not alter its biological properties, Glycobiology (2000), vol. 10, 511-519.*
Abuchowski et al., 1977, J. Biol. Chem. 252:3582-2586.
Abuchowski et al., 1984, Cancer Biochem. Biophys. 7:175-186.
Abuchowski et al., 1977, J. Biol. Chem. 252:3578-3581.
Ailor et al., 2000, Glycobiology 10:837-847.
Altmann et al., 1999, Glycoconjugate J. 16:109-123.
Aplin et al., 1981, CRC Crit Rev. Biochem. 259-306.
Beauchamp et al., 1983, Anal Biochem. 131:25-33.
Berger et al., 1988 71:1641-1647.

(Continued)

*Primary Examiner*—Cecilia J. Tsang
*Assistant Examiner*—Thomas S. Heard
(74) *Attorney, Agent, or Firm*—Morgan, Lewis & Bockius, LLP

(57) ABSTRACT

The present invention provides conjugates between erythropoietin and PEG moieties. The conjugates are linked via an intact glycosyl linking group interposed between and covalently attached to the peptide and the modifying group. The conjugates are formed from glycosylated peptides by the action of a glycosyltransferase. The glycosyltransferase ligates a modified sugar moiety onto a glycosyl residue on the peptide. Also provided are methods for preparing the conjugates, methods for treating various disease conditions with the conjugates, and pharmaceutical formulations including the conjugates.

36 Claims, 12 Drawing Sheets

FOREIGN PATENT DOCUMENTS

| WO | WO 92/18135 | 5/1993 |
|---|---|---|
| WO | WO 94/05332 | 3/1994 |
| WO | WO 94/15625 A1 | 7/1994 |
| WO | WO 95/02421 A1 | 1/1995 |
| WO | WO 96/40731 | 6/1996 |
| WO | WO 96/32491 | 10/1996 |
| WO | WO 97/05330 | 2/1997 |
| WO | WO 98/05363 | 2/1998 |
| WO | WO 87/05330 A1 | 7/1998 |
| WO | WO 98/31826 | 7/1998 |
| WO | WO 98/58694 | 12/1998 |
| WO | WO 99/22764 A1 | 5/1999 |
| WO | WO 99/00150 A2 | 7/1999 |
| WO | WO 00/65087 | 11/2000 |
| WO | WO 01/49830 A2 | 7/2001 |
| WO | WO 01/60411 A1 | 8/2001 |
| WO | WO 02/02597 A2 | 1/2002 |
| WO | WO 02/13843 A2 | 2/2002 |
| WO | WO 02/13873 A2 | 2/2002 |
| WO | WO 02/074806 A2 | 9/2002 |

OTHER PUBLICATIONS

BErg-Fassman et al. 1993, J. Biol. Chem. 268:14861-14866.
Bhadra et al., 2002, Pharmazie 57:5-29.
Bhatia et al., 1989, Anal. Biochem. 178:408-413.
Bickel et al., 2001, Adv. Drug Deliv. Rev. 46:247-279.
Bjoern, et al., 1992, J. Biol. Chem., 266(17):11051-11057.
Boccu et al., 1983, Z. Naturforsch 38C:94-99.
Boime et al., 1995, Endocrinology 136:2635-2640.
Boissel et al., 1993, J. Biol. Chem. 268:15983-15993.
Bouizar et al., 1986, Eur. J. Biochem. 155:141-147.
Boyd et al, 1995, Mol. Immunol. 32:1311-1318.
Browning et al., 1989, J. Immunol. 143:1859-1867.
Buckmann et al., 1981, Makromol. Chem. 182:1379-1384.
Burns et al., 2002, Blood 99:4400-4405.
Busterbosch et al., 1996, Eur. J. Biochem. 237:344-349.
Butnev et al., 1998, Biology of Reproduction 58:458-469.
Byun et al., 1992, ASAIO Journal M649-M653.
Casares et al., 2001, Nature Biotech 19:142-147.
Chaffee et al., 1992, J. Clin. Invest 89:1643-1651.
Charter et al., 2000, Glycobiology 10:1049-1056.
Chern et al., 1991, Eur. J. Biochem. 2002:225-229.
Chiba et al., 1995, Biochem J. 308:405-409.
Chrisey et al., 1996, Nucleic Acids Res. 24:3031-3039.
Clark, et al., 1996, J. Biol. Chem,271(36)21969-21977.
Cointe, et al., 2000, Glycobiology, 10(5):511-519.
Conradt et al., 1987, J. Biol. Chem. 262:14600-14605.
Copeland, Robert A., 2000, Enzymes, Second Edition, 146-150.
Crout et al., 1998, Curr. Opin. Chem. Biol. 2:98-111.
Degado et al., 1992, Critical Reviews in Therapeutic 9:249-304.
Delgaldo et al., Biotechnol. Appl. Biochem. 12:119-128.
Detty et al., 1982, J. Org. Chem. 47:5416-5418.
Dunn et al., 1991, Rds. Polymeric Drugs and Drug Delivery Systems, ACS Symposium Series vol. 469, American Chemical Society, Washington D.C.
Durieux, et al., 2001, Tetrahedron Letters, 42:2297-2299.
Dwek et al., 1995, J. Anat. 187:279-292.
Eavarone et al., 2000, J. Biomed Mater. Res. 51:10-14.
Fibi et al., 1995, Cells Blood 85:1229-1236.
Fischer et al., 1998, Thrombosis Research 89:147-150.
Flynn et al., 2000, Curr. Opin. Oncol. 12:574-581.
Garnett et al., 2002, Advanced Drug Delivery Reviews 53:171-216.
Gatot, et al., 1998, J. Biol. Chem., 273(21):12870-12880.
Gillis et al., 1988, Behring Inst. Mitt. Aug. 83:1-7.
Ginns, Dr. Edward, PEG Glucocerebrosidase, Internet page from www.gaucher.org.uk/peg2.prg, printed Jun. 21, 2002.
Grodberg et al., 1993, Eur. J. Biochem. 218:597-601.
Gross, H.J., 1992, Eur. J. Bioche,. 203(1-2):269-275.
Hall et al., 2001, Methods in Molecular Biology 166:139-154.
Haneda et al., Carbohydr. Res. 292:61-70.
Hang et al., 2001, J. Am. Chem. Soc. 123:1242-1243.
Harris, 1985, Macronol. Chem. Phys. C25: 325-373.
Hellstrom et al., 2001, Methods in Molecular Biology 166:3-16.
Hermanson et al., 1992, Immobilized Affinity Ligand Techniques, Academic Press.
Hermanson, 1996, Bioconjugate Techniques, Academic Press, San Diego.
Hills et al., 2002, American Biotechnology Laboratory, 20(11):30.
Hollister et al., 2001, Glycobiology 11:1-19.
Hounsell et al., 1996, Glycoconj. J. 13:19-26.
Ichikawa et al., 1992, J. Am. Chem. Soc. 114:9283-9298.
Inoue et al., 1995, Biotechnology Annual Review 1:297-313.
Ito et al., 1992, Pure Appl. Chem. 65:753-762.
Jackson et al., 1987, Anal. Biochem. 165:114-127.
Jarvis et al., 1998, Curr, Opin, Biotechnol. 9:528-533.
Joppich et al., 1979, Makromol Chem. 180:1381-1384.
Joshi et al., 1990, J. Biol. Che,. 265:14518-14525.
Jung et al., 1983, Biochem. Biophys. Acta, 761:152-162.
Kalsner et al., 1995, Glycoconj. J. 12:360-370.
Kasina et al., 1998 Bioconjugate Chem., 9:108-117.
Katre et al., 1987, Proc. Natl. Acad. Sci. U.S.A. 84:1487-1491.
Keppler et al., 2001, Glycobiology 11:11R-18R.
Kitamura et al., 1990, Biochem. Biophys. Res. Commun. 28:1387-1394.
Kitamura et al., 1991, Cancer Res. 51:4310-4315.
Kodama et al., 1993, Tetrahedron Lett. 34:6419-6422.
Koeller et al., 2000, Nature Biotechnology 18:835-841.
Koide et al., 1983, Biochem Biophys. Res. Commun. 111:659-667.
Kreitmann 2001, Current Pharaceutical Biotechnology 2:313-325.
Kuhn, et al., 1995, J. Biol. Chem. 270(49):29493-29497.
Lai et al, 1986, J. Biol. Che,. 261:3116-3121.
Lee-Huang et al., 1984, Proc. Natl. Acad. Sci. U.S.A. 81:2708-2712.
Lee et al., 1989, Biochemistry 28:1856-1861.
Li et al., 2002, Trends in Pharmacological Science 23:206-209.
Li et al., 2002, Medicinal Research Reviews 22:225-250.
Liu et al., 2002, 1996, Chem. Eur. J. 2:1359-1362.
Lord et al., 2001, Clin. Cancer Res. 7:2085-2090.
Lougheed et al., 1999, J. Biol. Che,. 274:37717-37722.
Luckow et al., 1993, Curr. Opin, Biotechnol 4:564-572.
Lund et al., 1995, FASEB J. 9:115-119.
Lund et al., 1996, J. Immunol. 157:4963-4969.
Mahal et al., 1997, Science 276:1125-1128.
Maras et al., 2000, Molecular cloning and enzymatic characterization of a Trichoderma reesei , 2-α-D-mannosidase, 77:255-263.
Miller et al., 1993, Curr. Opin. genet. Dev. 3:97-101.
Min et al., 1996, Endocr. J. 43:585-593.
Mistry et al., 1996, Lancet 348:1555-1559.
Morimoto et al., 1996, Glycoconjugate J. 13:1013-1020.
Nilsson et al., 1984, Methods Enzymol. 104:56-69.
O'Connell et al., 1992, J. Biol. Chem. 267:25010-25018.
Olson et al., 1999, J. Biol. Chem. 274:29889-29896.
Palacpac et al., 1999, PNAS USA 96:4692-4697.
Park et al., 1986, J. Biol Chem. 261:205-210.
Paulson et al., 1997, J. Biol. Chem. 252:8624-8628.
PNGase-F Amidase Sequence from F. Meningosepticum (Registry numbers 128688-70-0).
PNGase-F Amidase Sequence from F. Meningosepticum (Registry numbers 128688-71-7).
Pyatak et al., 1980, Res. Commun. Chem. Pathol Pharmacol 29:113-127.
Rabouille et al., 1999, J. Cell. Biol. 112:3319-3330.
Reff et al., 2002, Cancer Control 9:152-166.
Sadler et al., 1982, Methods in Enzymology 83:458-514.
Saneyoshi et al., 2001, Biology of Reproduction 65:1686-1690.
Saxon et al., 2000, Science 287:2007-2010.
Schwientek et al., 1994, Gene 145:299-303.
Scouten 1987, Methods in Enzymology 135:30-65.
Shah et al., 1996, J. Pharm. Sci. 85:1306-1311.
Singh et al., 1996, Chem. Commun. 1996:993-994.
Song et al., 2002, J. Pharmacol. Exp. Ther. 301:605-610.
Srinivasachar et al., 1989, Biochemcitry 28:2501-2509.
Takane et al., 2000, J. Pharmacology and Experimental Therapeutics 294:746-752.

Takeda et al., 1995, Trends Biochem. Sci. 20:367-371.
Tanner et al., 1987, Biochem. Biophys. Acta., 906:81-91.
Taylor et al., 1991, Protein Immobilization Fundamentals and Applications, Manual.
Thotakura et al., 1987, Meth Enzymol 138: 350-359.
Tsuboi et al., 2000 Archives of Biochemistry and Biophysics 374: 100-106.
Udenfriend et al., 1995, Ann. Rev. Biochem. 64:563-591.
Ulloa-Aguirre et al., 1999, Role of Glycosylation in Function of Follicle-Stimulating Hormone, Endocrine 11:205-215.
Uludag et al., 2002, Biotechnol. Prog. 18:604-611.
Urdal et al, 1984, J. Chromatog, 296:171-179.
Van Berkel et al., 1996, Biochem J. 319:117-122.
Veronse et al., 1985, Appl. Biochem. Biotech. 11:141-152.
Vocadlo et al., 2000, In Carbohydrate Chemistry and Biology, vol. 2.
Vyas et al., 2001, Crit. Rev. Ther. Drug Carrier Syst. 18:1-76.
Wang et al., 1996, Tetrahedron Lett. 37:1975-1978.
Wellhoner et al., 1991, J. Biol. Chem. 226:4309-4314.
Witte K. et al., 1997, J. Am. Chem. Soc. 119:2114-2118.
Woghiren et al., 1993, Bioconjugate Chem. 4:314-318.
Wong et al., 1992, Enzyme Microb. Technol. 14:866-874.
Woods et al., 1989, Eur. J. Cell. Biol. 50:132-143.
Wright et al., 1998, J. Immunol. 160:3393-3402.
Wu et al., 2002, J. Drug targeting 10:239-245.
Xing et al., 1998, Biochem. J. 336:667-673.
Yamamoto et al., 1998, Carbohydr. Res. 305:415-422.
Yarema et al., 1998, J. Biol. Chem. 47:31168-31179.
Yoshida et al., 1999, Glycobiology 9:53-58.
Zalipsky 1995, Bioconjugate Chem. 6:150-165.
Zalipsky et al., 1992, Poly (ethylene glycol) Chemistry: Biotechnical and Biomedical Applications 347-370.
Makoto Takeuchi, et al., "Role of Sugar Chains in the in Vitro Biological Activity of Human Erythropoietin Produced in Recombinant Chinese Hamster Ovary Cells," *The Journal of Biological Chemistry*, 265(21): 12127-12130, 1990.

\* cited by examiner and

Structure of CMP-SA-PEG(40K)

Structure of CMP-SA-PEG(30K)

*30 kDa*

COMPARATIVE PLASMA CLEARANCE RATES FOR PEGYLATED AND NON-PEGYLATED EPO VARIANTS.

- ♦ Non-glycopegylated CHO-EPO
- ● Non-glycopegylated CHO-EPO
- ■ Glycopegylated insect-derived EPO
- ▲ 40K glycopegylated CHO-EPO

```
                        SEQUENCE LISTING

<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
```

```
                85                  90                  95
Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

GLYCOPEGYLATED ERYTHROPOIETIN

CROSS-REFERENCES TO RELATED APPLICATIONS

The present application claims priority to U.S. Provisional Patent Application No. 60/524,989, filed Nov. 24, 2003; U.S. Provisional Patent Application No. 60/539,387, filed Jan. 26, 2004; U.S. Provisional Patent Application No. 60/555,504, filed Mar. 22, 2004; U.S. Provisional Patent Application No. 60/590,573, filed Jul. 23, 2004; U.S. Provisional Patent Application No. 60/592,744, filed Jul. 29, 2004; U.S. Provisional Patent Application No. 60/614,518, filed Sep. 29, 2004; and U.S. Provisional Patent Application No. 60/623,387, filed Oct. 29, 2004 each of which is incorporated herein by reference in their entirety for all purposes.

BACKGROUND OF THE INVENTION

Erythropoietin (EPO) is a cytokine produced by the kidney and liver which acts on hematopoietic stem cells to stimulate the production of red blood cells. The protein exists in two forms: one being a 165 amino acid peptide, and the other is a 166 amino acid peptide. The 166 amino acid peptide has the same sequence as the 165 amino acid peptide except that the 166 amino acid peptide has an additional arginine in the most C-terminal position. The mature 165 amino acid peptide is a 34 kD glycoprotein comprising three N-glycosylation sites (Asn-24, Asn-38, and Asn-83), and 1 O-glycosylation site (Ser-126), and some variants are "hyperglycosylated" comprising 5 N-linked glycosylation sites.

Erythropoietin synthesis is induced by conditions that effectively create tissue hypoxia, such as lowering of the arterial $O_2$ tension or increasing the oxygen affinity of the blood. Under usual conditions of homeostasis, hematocrit and the concentration of hemoglobin in blood are maintained constant with erythropoiesis counterbalancing the permanent destruction of aged red blood cells by macrophages in bone marrow, spleen and liver. Quantitatively, about 1% of the red cell mass, which is about $2\text{-}3 \times 10^{11}$ red blood cells, is renewed each day. However, in situations that effectively generate tissue hypoxia, such as blood loss or location to high altitudes, the induction of EPO may stimulate erythropoesis 10-fold or more over normal levels.

Because EPO stimulates red blood cell production, it is an effective therapy for many diseases and conditions associated with reduced hematocrit. Initial trials of replacement therapy with recombinant human EPO to restore the hematocrit in patients with end-stage renal failure were first reported about 20 years ago (see e.g., Winearls, C. G.; et al. (1986) Lancet, 2, 1175-1178, and Eschbach, J. W.; et al. (1987) N. Engl. J. Med., 316, 73-78). This work provided an impetus for further studies into the pathophysiology and pharmacology of EPO (see e.g., Jelkmann, W. and Gross, A. (1989) Erythropoietin; Springer, Berlin Heidelberg New York).

Since those early studies, recombinant human EPO has been used successfully to treat numerous pathological conditions. For example, the pharmacological application of recombinant human EPO to surgical patients can lower the severity and duration of postoperative anemia. The administration of recombinant human EPO has also proven to be effective therapy for patients suffering from several non-renal diseases, such as chronic inflammation, malignancy and AIDS, wherein a relative lack of endogenous EPO contributes to the development of anemia (see e.g., Means, R. T. and Krantz, S. B. (1992) Blood, 80, 1639-1647, and Jelkmann, W. (1998) J. Interf. Cytokine Res., 18, 555-559). Furthermore, it has been reported that EPO is tissue protective in ischemic, traumatic, toxic and inflammatory injuries (see e.g., Brines M., et al. (2004) PNAS USA 101:14907-14912 and Brines, M. L., et al. (2000). Proc. Natl. Acad. Sci. USA 97, 10526-10531).

The usefulness and effectiveness of EPO for the treatment of anemias and other conditions arising from such a wide variety of causes makes recombinant human EPO perhaps the best selling drug in the world. Indeed, estimated sales amount to more than 5 billion US dollars per year.

Only one recombinant human EPO, produced in Chinese Hamster Ovary (CHO) cell line, is used extensively as a therapeutic. Since mammals all produce glycans of similar structure, Chinese Hamster Ovary (CHO), Baby Hamster Kidney (BHK), and Human Embryonic Kidney-293 (HEK-293) are the preferred host cells for production of glycoprotein therapeutics. As is known in the art, proper glycosylation is a critically important factor influencing the in vivo the half life and immunogenicity of therapeutic peptides. Indeed, poorly glycosylated proteins are recognized by the liver as being "old" and thus, are more quickly eliminated from the body than are properly glycosylated proteins.

Unfortunately, one frustrating, and well known aspect of of protein glycosylation is the phenomenon of microheterogeneity. Thus, even the preferred host cells for production of human therapeutic glycoproteins such as EPO, typically produce peptides comprising a range of variations in the precise structure of the glycan. The extent of this heterogeneity can vary considerably from glycosylation site to glycosylation site, from protein to protein, and from cell type to cell type. Therefore, numerous glycoforms, each of which each is effectively a distinct molecular species, typically exist in any given glycoprotein preparation.

The problem of microheterogeneity thus poses numerous problems for the large industrial scale production of therapeutic glycoproteins. In particular, since each glycoform can represent a distinct molecular species, preparations of therapeutic glycoproteins must be fractionated to purify the desired single glycoform. Further complications arise from the fact that different production batches may vary with respect to the percentage of the desired glycoform comprising the batch of glycoprotein therapeutic. Thus, large, not always predictable portions of each preparation may be have to be discarded, so that ultimately the final yeild of a desired glycoform can be low. Overall, the problem of microheterogeneity means that therapeutic glycopeptides produced by mammalian cell culture require higher production costs, which ultimately translate to higher health care costs than might be necessary if a more efficient method for making longer lasting, more effective glycoprotein therapeutics was available.

One solution to the problem of providing cost effective glycopeptide therapeutics has been to provide peptides with longer in vivo half lives. For example, glycopeptide therapeutics with improved pharmacokinetic properties have been produced by attaching synthetic polymers to the peptide backbone. An exemplary polymer that has been conjugated to peptides is poly(ethylene glycol) ("PEG"). The use of PEG to derivatize peptide therapeutics has been demonstrated to reduce the immunogenicity of the peptides. For example, U.S. Pat. No. 4,179,337 (Davis et al.) discloses non-immunogenic polypeptides such as enzymes and peptide hormones coupled to polyethylene glycol (PEG) or polypropylene glycol. In addition to reduced immunogenicity, the clearance time in circulation is prolonged due to the increased size of the PEG-conjugate of the polypeptides in question.

The principal mode of attachment of PEG, and its derivatives, to peptides is a non-specific bonding through a peptide amino acid residue (see e.g., U.S. Pat. No. 4,088,538 U.S. Pat. No. 4,496,689, U.S. Pat. No. 4,414,147, U.S. Pat. No. 4,055,635, and PCT WO 87/00056). Another mode of attaching PEG to peptides is through the non-specific oxidation of glycosyl residues on a glycopeptide (see e.g., WO 94/05332).

In these non-specific methods, poly(ethyleneglycol) is added in a random, non-specific manner to reactive residues on a peptide backbone. Of course, random addition of PEG molecules has its drawbacks, including a lack of homogeneity of the final product, and the possibility for reduction in the biological or enzymatic activity of the peptide. Therefore, for the production of therapeutic peptides, a derivitization strategy that results in the formation of a specifically labeled, readily characterizable, essentially homogeneous product is superior. Such methods have been developed.

Specifically labeled, homogeneous peptide therapeutics can be produced in vitro through the action of enzymes. Unlike the typical non-specific methods for attaching a synthetic polymer or other label to a peptide, enzyme-based syntheses have the advantages of regioselectivity and stereoselectivity. Two principal classes of enzymes for use in the synthesis of labled peptides are glycosyltransferases (e.g., sialyltransferases, oligosaccharyltransferases, N-acetylglucosaminyltransferases), and glycosidases. These enzymes can be used for the specific attachment of sugars which can be subsequently modified to comprise a therapeutic moiety. Alternatively, glycosyltransferases and modified glycosidases can be used to directly transfer modified sugars to a peptide backbone (see e.g., U.S. Pat. No. 6,399,336, and U.S. Patent Application Publications 20030040037, 20040132640, 20040137557, 20040126838, and 20040142856, each of which are incorporated by reference herein). Methods combining both chemical and enzymatic synthetic elements are also known (see e.g., Yamamoto et al. *Carbohydr. Res.* 305: 415-422 (1998) and U.S. Patent Application Publication 20040137557 which is incorporated herein by reference).

Erythropoietin (EPO) is an extremely valuble therapeutic peptide. Although commercially available forms of EPO are in use today, these peptides are less than maximally effective due factors including microheterogeneity of the glycoprotein product which increases production costs, poor pharmacokinetics of the resulting isolated glycoprotein product, or a combination of the two. Thus, there remains a need in the art for long lasting EPO peptides with improved effectiveness and better pharmacokinetics. Furthermore, to be effective for the largest number of individuals, it must be possible to produce, on an industrial scale, an EPO peptide with improved therapeutic pharmacokinetics that has a predictable, essentially homogeneous, structure which can be readily reproduced over, and over again.

Fortunately, EPO peptides with improved the therapeutic effectiveness and methods for making them have now been discovered. Indeed, the invention provides EPO peptides with improved pharmacokinetics. The invention also provides industrially practical and cost effective methods for the production of modified EPO peptides. The EPO peptides of the invention comprise modifying groups such as PEG moieties, therapeutic moieties, biomolecules and the like. The present invention therefore fulfills the need for EPO peptides with improved the therapeutic effectiveness and improved pharmacokinetics for the treatment of conditions and diseses wherein EPO provides effective therapy.

SUMMARY OF THE INVENTION

It has now been discovered that the controlled modification of erythropoietin (EPO) with one or more poly(ethylene glycol) moieties affords novel EPO derivatives with improved pharmacokinetic properties. Furthermore, cost effective methods for reliable production of the modified EPO peptides of the invention have been discovered and developed.

In one aspect, the present invention provides an erythropoietin peptide comprising the moiety:

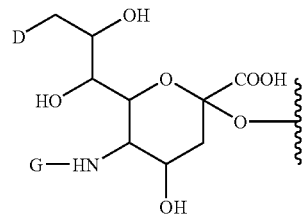

wherein D is a member selected from —OH and $R^1$-L-HN—; G is a member selected from $R^1$-L- and —C(O)($C_1$-$C_6$)alkyl; $R^1$ is a moiety comprising a member selected a moiety comprising a straight-chain or branched poly(ethylene glycol) residue; and L is a linker which is a member selected from a bond, substituted or unsubstituted alkyl and substituted or unsubstituted heteroalkyl, such that when D is OH, G is $R^1$-L-, and when G is —C(O)($C_1$-$C_6$)alkyl, D is $R^1$-L-NH—. In one embodiment, a $R^1$-L has the formula:

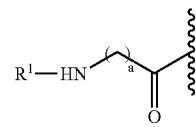

wherein a is an integer from 0 to 20. In another embodiment, $R^1$ has a structure that is a member selected from:

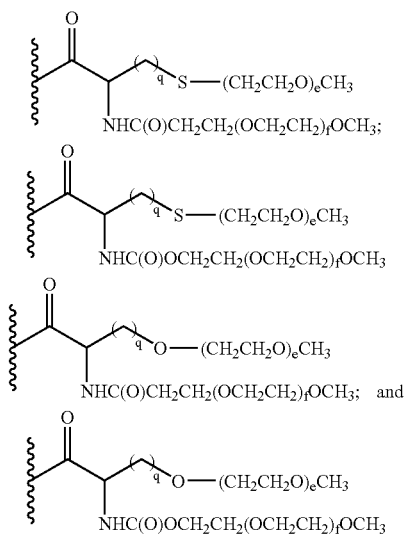

wherein e and f are integers independently selected from 1 to 2500; and q is an integer from 1 to 20. In other embodiments $R^1$ has a structure that is a member selected from:

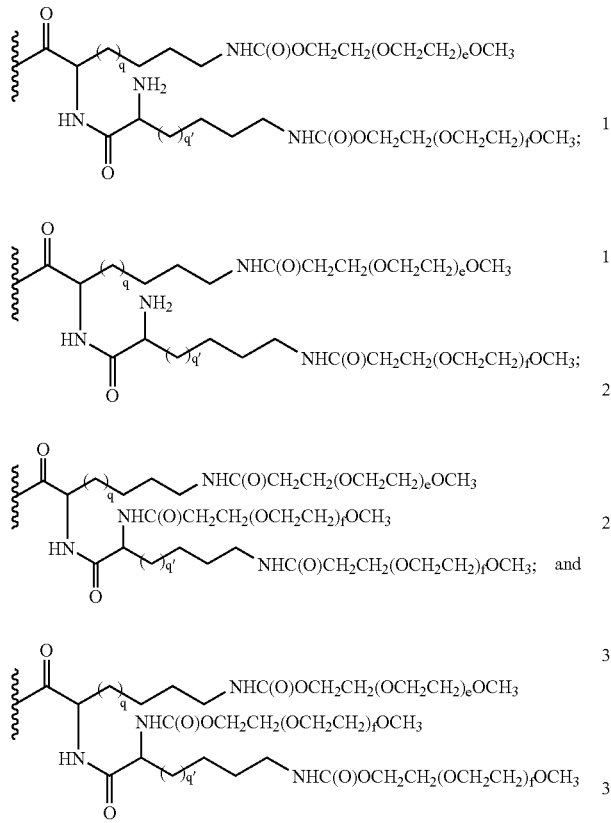

wherein e, f and f' are integers independently selected from 1 to 2500; and q and q' are integers independently selected from 1 to 20.

In still another embodiment, the invention provides a peptide wherein $R^1$ has a structure that is a member selected from:

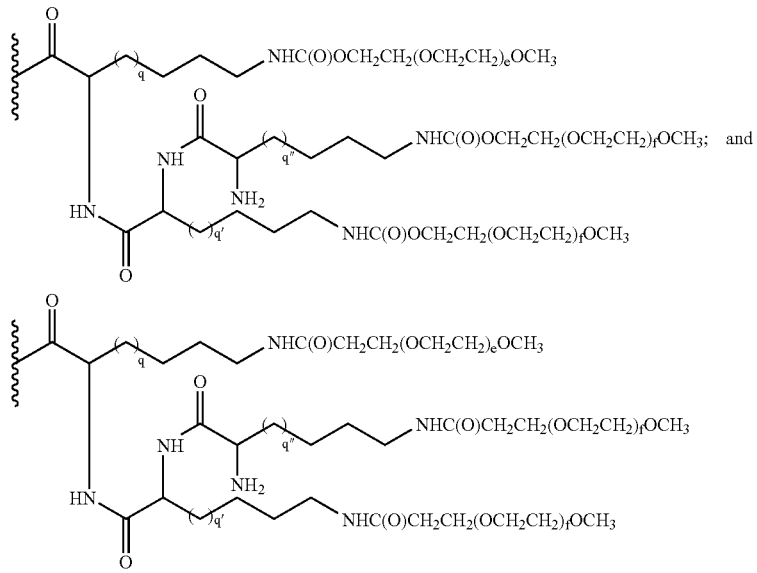

wherein e, f and f' are integers independently selected from 1 to 2500; and q, q' and q" are integers independently selected from 1 to 20. In other embodiments, $R^1$ has a structure that is a member selected from:

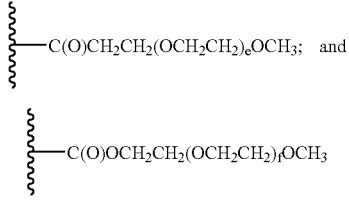

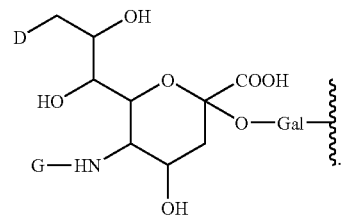

wherein e and f are integers independently selected from 1 to 2500.

In another aspect, the invention provides a peptide comprising a moiety having the formula:

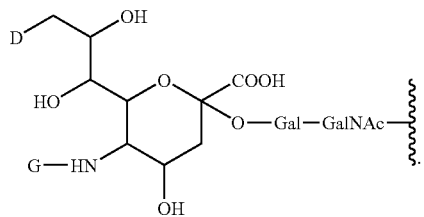

In other embodiments, the moiety has the formula:

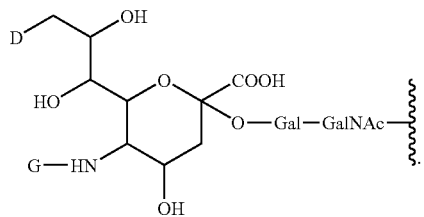

In another exemplary embodiment the peptide comprises a moiety according to the formula

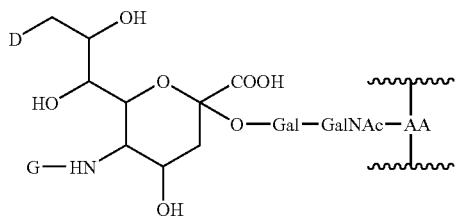

wherein AA is an amino acid residue of said peptide. In some embodiments the amino acid residue is a member selected from serine, threonine and tyrosine. In a preferred embodiment the amino acid residue is a serine at position 126 of SEQ. ID. NO:1.

In another exemplary embodiment, the invention provides an erythropoeitin peptide wherein the peptide comprises at least one moiety that has the formula:

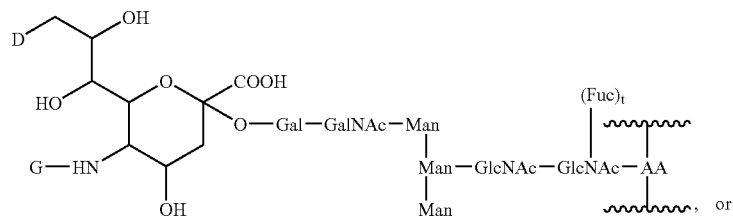

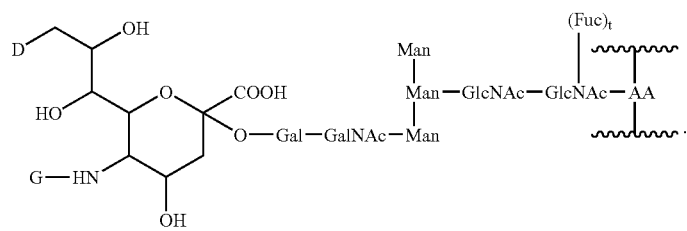

wherein t is an integer from equal to 0 or 1. Thus, in this embodiment, the modified sialic acid moiety may occur on either branch of the biantennary structure.

In another related embodiment, the invention provides an erythropoeitin peptide wherein the peptide comprises at least one moiety that has the formula:

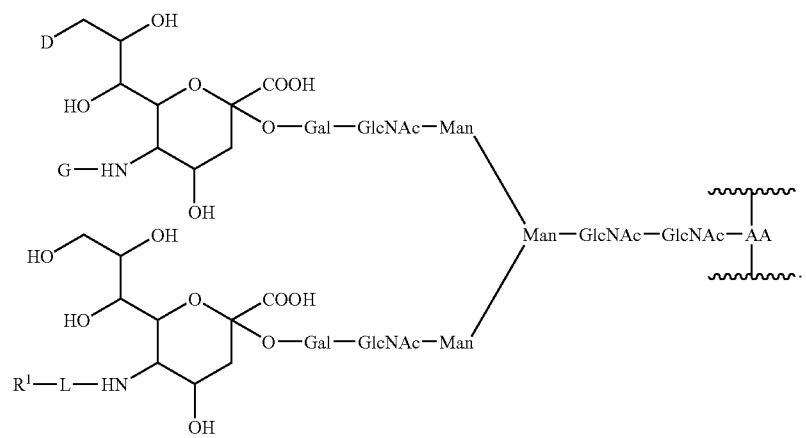

In another embodiment, the invention provides an erythropoeitin peptide wherein the peptide comprises at least one moiety that has a formula according to:

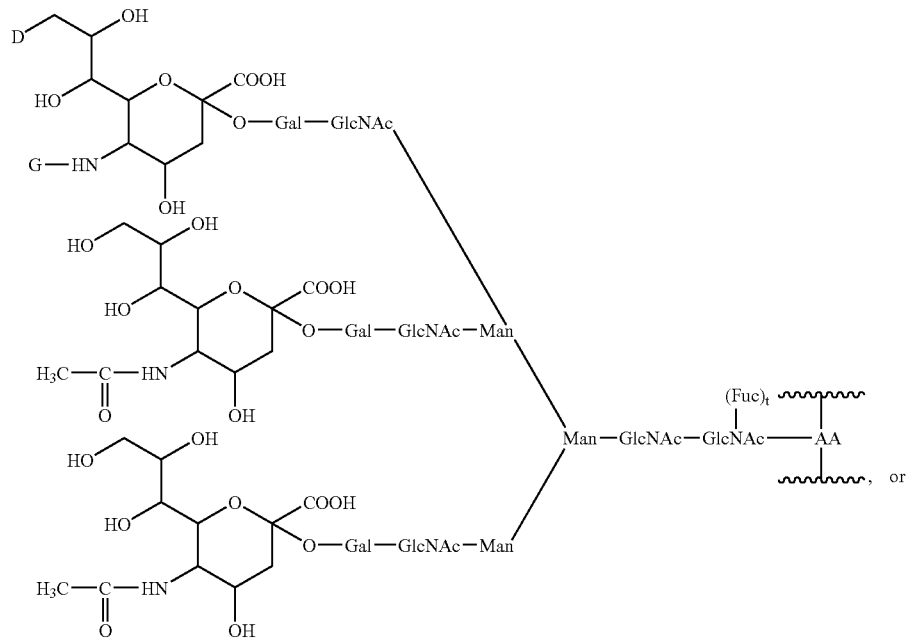

In this embodiment, the modified sialic acid moiety may occur on any one or more of the branches of the either form of the triantennary structure.

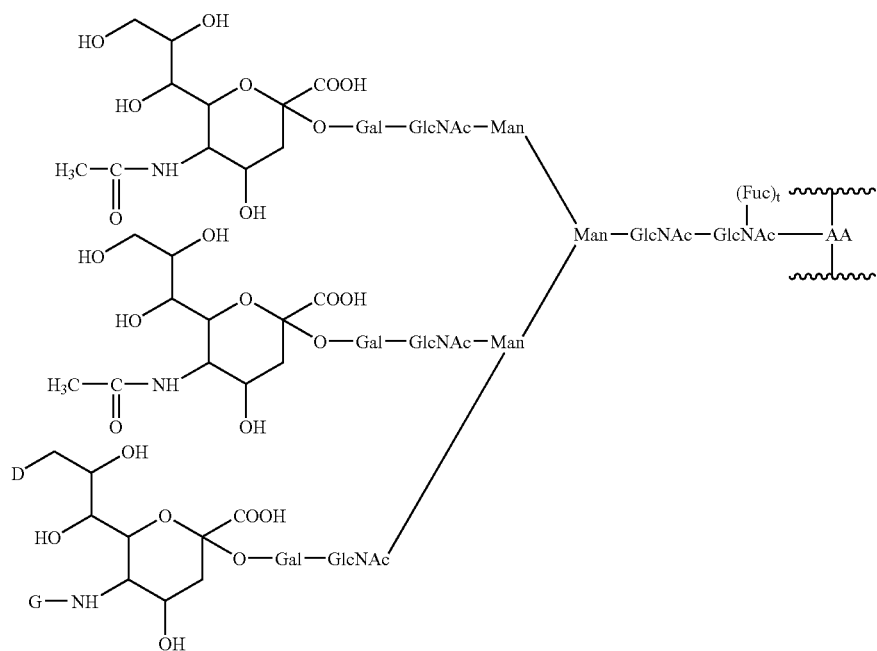

In still another embodiment, the invention provides an erythropoeitin peptide wherein the peptide comprises at least one moiety that has the formula:

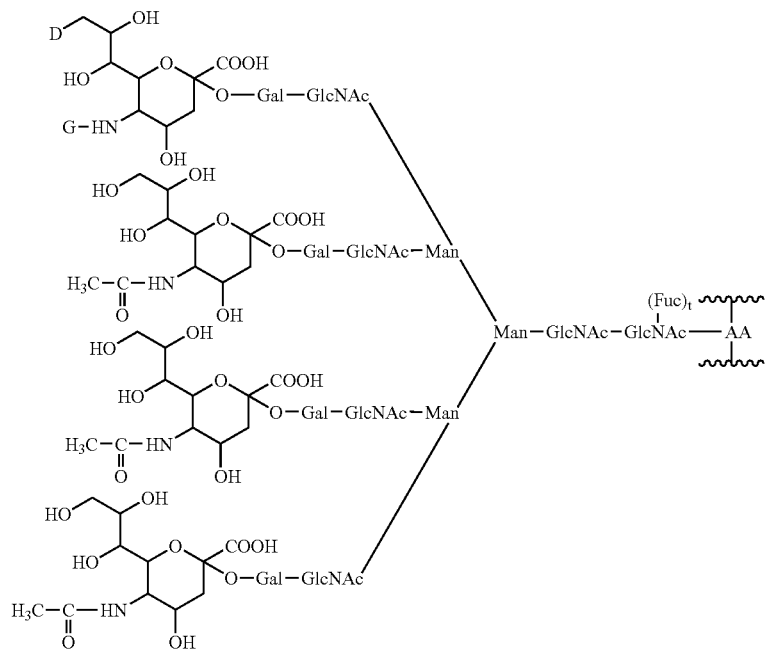

In this embodiment, the modified sialic acid moiety may occur on any one or more of the branches of the tetra antennary structure.

In another aspect the invention provides an erythropoetin peptide that is a bioactive erythropoietin peptide. In one embodiment, the erythropoietin peptide is erythropoietically active. In another embodiment, the erythropoietin peptide is essentially non-erythropoietically active. In another embodiment, the erythropoietin peptide is tissue protective.

In another aspect, the invention provides a method of making a PEG-ylated erythropoietin comprising the moiety:

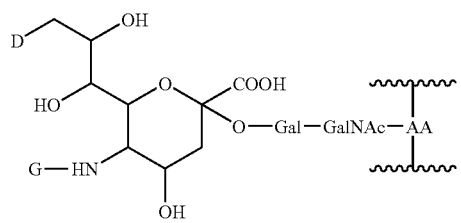

wherein $R^1$ is a moiety comprising straight-chain or branched poly(ethylene glycol) residue; and L is a linker which is a member selected from substituted or unsubstituted alkyl and substituted or unsubstituted heteroalkyl. The method comprises contacting a substrate erythropoietin peptide comprising the glycosyl moiety:

with a PEG-sialic acid donor moiety having the formula:

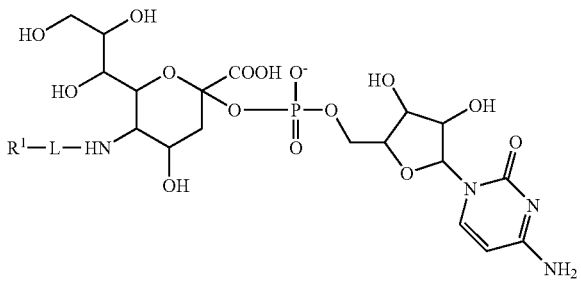

and an enzyme that transfers said PEG-sialic acid onto the Gal of said glycosyl moiety, under conditions appropriate to for the transfer. In one embodiment, the erythropoietin peptide is expressed in a suitable host. In one embodiment the host is mammalian cell, and in another embodiment the host cell is an insect cell.

In another aspect, the invention provides a method of treating a condition in a subject in need thereof, wherein the condition is characterized by compromised red blood cell production in the subject. The method comprises the step of administering to the subject an amount of the erythropoietin peptide of the invention effective to ameliorate the condition in the subject.

In another aspect, the invention provides a method of enhancing red blood cell production in a mammal. The method comprises administering to the mammal an amount of the erythropoietin peptide of the invention effective to enhance red blood cell production in the mammal.

In another aspect, the invention provides a method of treating a tissue injury in a subject in need thereof, said injury characterized by damage resulting from ischemia, trauma, inflammation or contact with toxic substances, said method comprising the step of administering to the subject an amount of an erythropoietin peptide of the invention effective to ameliorate said tissue injury in the subject.

In another aspect, the invention provides a pharmaceutical formulation comprising the erythropoietin peptide of the invention and a pharmaceutically acceptable carrier.

In the o-linked erythropoietin conjugates of the invention, essentially each of the amino acid residues to which the polymer is bound has the same structure. For example, if one peptide includes a Ser linked glycosyl residue, at least about 70%, 80%, 90%, 95%, 97%, 99%, 99.2%, 99.4%, 99.6%, or more preferably 99.8% of the peptides in the population will have the same glycosyl residue covalently bound to the same Ser residue.

Other objects and advantages of the invention will be apparent to those of skill in the art from the detailed description that follows.

DESCRIPTION OF THE DRAWINGS

FIG. 1 illustrates some exemplary modified sugar nucleotides useful in the practice of the invention.

FIG. 2 illustrates further exemplary modified sugar nucleotides useful in the practice of the invention.

FIG. 3 illustrates exemplary modfied sialic acid nucleotides useful in the practice of the invention. A: Structure of 40 kilodalton CMP-Sialic acid-PEG. B: Structure of 30 kilodalton CMP-Sialic acid-PEG.

FIG. 4 presents a schematic representation of exemplary glycopegylated EPO isoforms isolated from Chinese Hamster Ovary cells. A. An eemplary 40 kilodaton O-linked pegylated glycoform. B: One of several 30 kilodatton N-linked pegylated glycoforms. The modified sialic acid moiety comprising the PEG molecule, may occur on any one or more of any of the branches of the N-linked glycosyl residue. Furthermore the illustration is exemplary in that any glycosylated EPO molecule may comprise any mixture of mono-, bi- tri-, or tetra-antennary N-linked glycosyl residues and any one or more of the branches may further comprise a modified sialic acid moiety of the invention.

FIG. 5 illustrates an exemplary CHO-derived EPO peptide in its non-glycopegylated form. As discussed in the legend to FIG. 4 (above) the illustration is exemplary in that any glycosylated EPO molecule may comprise any mixture of mono-, bi-tri-, or tetra-antennary N-linked glycosyl residues.

FIG. 6 shows the results of experiments comparing the pharmacokinetics of two CHO-derived non-glycopegylated EPO forms, and two different CHO-derived glycopegylated EPO forms.

FIG. 7 illustrates an insect-derived glycopegylated EPO peptide according to the invention.

FIG. 8 shows the results of experiments comparing the pharmacokinetics of a CHO-derived non-glycopegylated EPO form, an insect-derived non-glycopegylated EPO form, with their corresponding glycopegylated forms.

FIG. 9 shows the relative activites of two forms of non-glycopegylated EPO (A and B) versus two glycoPEGylated variants (the 30 kilodalto and 40 kilodalton variants of FIGS. 4A and B) and a hyperglycosylated EPO variant in stimulating proliferation of EPO receptor-bearing TF1 cells in culture.

FIG. 10 shows inhibition of binding of isotope-labeled EPO to a recombinant chimeric EPO receptor by various concentrations of two non-pegylated EPO variants (A and B) and two glycoPEGylated variants (the 30 kilodalto and 40 kilodalton variants of FIGS. 4A and B).

DETAILED DESCRIPTION OF THE INVENTION AND THE PREFERRED EMBODIMENTS

Abbreviations

Figure 1:
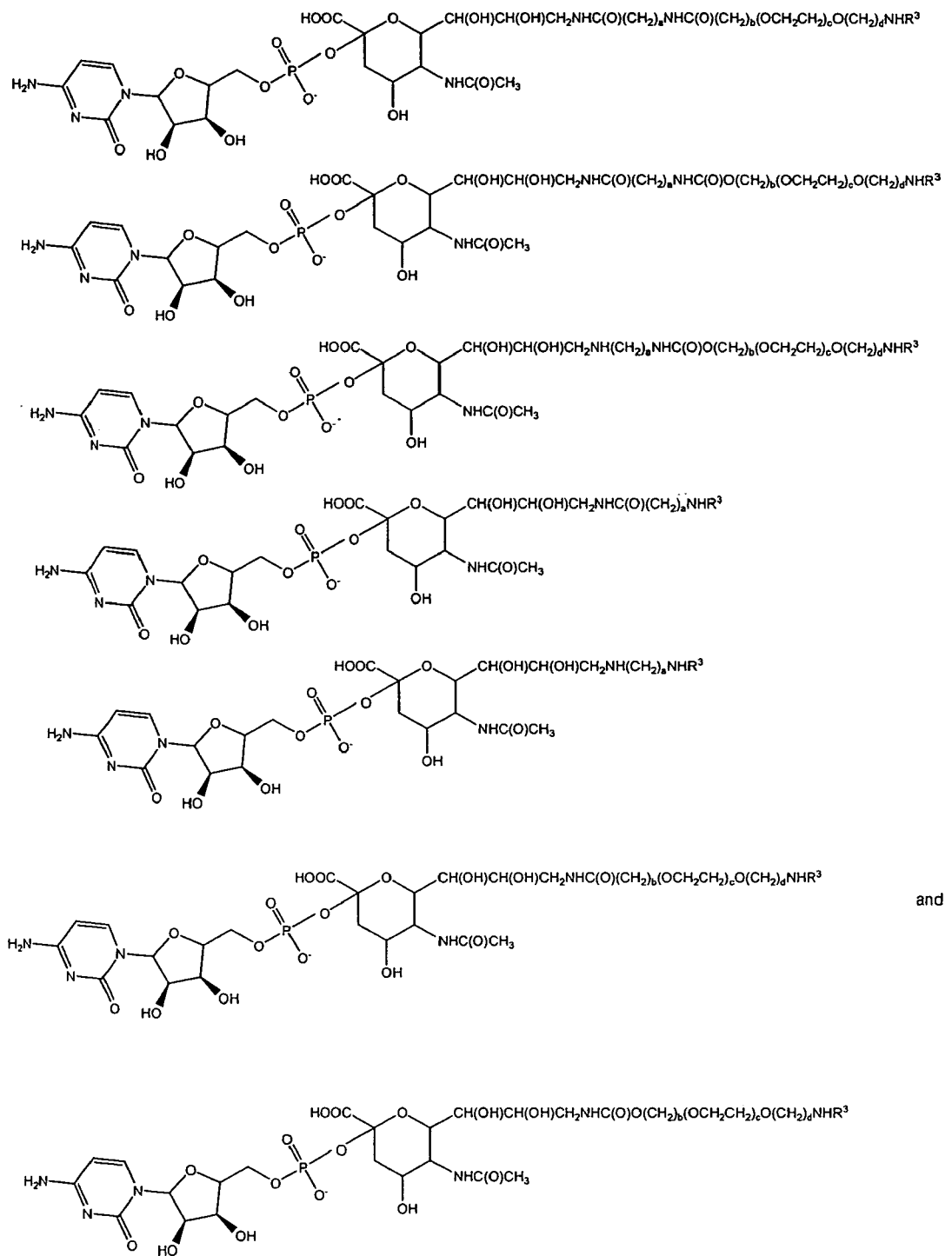
FIG. 1.

PEG, poly(ethyleneglycol); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; and NeuAc, sialyl (N-acetylneuraminyl); M6P, mannose-6-phosphate.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

All oligosaccharides described herein are described with the name or abbreviation for the non-reducing saccharide (i.e., Gal), followed by the configuration of the glycosidic bond ($\alpha$ or $\beta$), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature see, *Essentials of Glycobiology* Varki et al. eds. CSHL Press (1999).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are petides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "peptide conjugate," refers to species of the invention in which a peptide is conjugated with a modified sugar as set forth herein.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, the term "modified sugar," refers to a naturally- or non-naturally-occurring carbohydrate that is enzymatically added onto an amino acid or a glycosyl residue of a peptide in a process of the invention. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, PEG moieties, therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol). Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as $R(-PEG-OH)_m$ in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The "area under the curve" or "AUC", as used herein in the context of administering a peptide drug to a patient, is defined as total area under the curve that describes the concentration of drug in systemic circulation in the patient as a function of time from zero to infinity.

The term "half-life" or "t½", as used herein in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. For some glycosylated peptides, rapid beta phase clearance may be mediated via receptors on macrophages, or endothelial cells that recognize terminal galactose, N-acetylgalactosamine, N-acetylglucosamine, mannose, or fucose. Slower beta phase clearance may occur via renal glomerular filtration for molecules with an effective radius<2 nm (approximately 68 kD) and/or specific or non-specific uptake and metabolism in tissues. GlycoPEGylation may cap terminal sugars (e.g., galactose or N-acetylgalactosamine) and thereby block rapid alpha phase clearance via receptors that recognize these sugars. It may also confer a larger effective radius and thereby decrease the volume of distribution and tissue uptake, thereby prolonging the late beta phase. Thus, the precise impact of glycoPEGylation on alpha phase and beta phase half-lives will vary depending upon the size, state of glycosylation, and other parameters, as is well known in the art. Further explanation of "half-life" is found in Pharmaceutical Biotechnology (1997, DFA Crommelin and RD Sindelar, eds., Harwood Publishers, Amsterdam, pp 101-120).

The term "glycoconjugation," as used herein, refers to the enzymatically mediated conjugation of a modified sugar species to an amino acid or glycosyl residue of a polypeptide, e.g., an Erythropoietin peptide of the present invention. A subgenus of "glycoconjugation" is "glycol-PEGylation," in which the modifying group of the modified sugar is poly (ethylene glycol), and alkyl derivative (e.g., m-PEG) or reactive derivative (e.g., H2N-PEG, HOOC-PEG) thereof.

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g, multivalent agents. Therapeutic moiety also includes proteins and constructs that include proteins. Exemplary proteins include, but are not limited to, Granulocyte Colony Stimulating Factor (GCSF), Granulocyte Macrophage Colony Stimulating Factor (GMCSF), Interferon (e.g., Interferon-α, -β, -γ), Interleukin (e.g., Interleukin II), serum proteins (e.g., Factors VII, VIIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering," means oral administration, administration as a suppository, topical contact, intravenous, intraperitoneal, intramuscular, intralesional, intranasal or subcutaneous administration, or the implantation of a slow-release device e.g., a mini-osmotic pump, to the subject. Adminsitration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount" or "an amount effective to"or a "therapeutically effective amount" or any gramatically equivalent term means the amount that, when administered to an animal for treating a disease, is sufficient to effect treatment for that disease.

The term "tissue protective" refers to the defense of a tissue against the effects of cellular damage that are typically associated with the experience by a tissue or organ of ischemia/hypoxia, trauma, toxicity and/or inflammation. Cellular damage may lead to apoptosis and/or necrosis (i.e., toxic cell death). Thus, a "tissue protective" effect gaurds a tissue from experiencing the degree of apoptosis and/or toxic cell death normally associated with a given traumatic, inflammatory, toxic or ischemic injury. For example, EPO reduces the area of infarct after middle cerebral artery occlusion in a rodent model (Siren, A. L. et al. (2001). *Proc. Natl. Acad. Sci. U.S.A.* 98, 4044-4049). Thus, under such conditions EPO provides a "tissue protective" effect by effectively reducing the necrosis and/or apoptosis normally associated with the ischemic injury (e.g., ischemic stroke). "Tissue protective" also refers to the defense of a tissue against the effects of cellular damage and the ensuing cell death associated with degenerative diseases such as retinopathy, or neurodegenerative disease.

The term "isolated" refers to a material that is substantially or essentially free from components, which are used to produce the material. For peptide conjugates of the invention, the term "isolated" refers to material that is substantially or essentially free from components which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—$S(O)_2$—$CH_3$, —CH=CH—O—$CH_3$, —$Si(CH_3)_3$, —$CH_2$—CH=N—$OCH_3$, and —CH=CH—$N(CH_3)$—$CH_3$. Up to two heteroatoms may be consecutive, such as, for example, —$CH_2$—NH—$OCH_3$ and —$CH_2$—O—$Si(CH_3)_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2$R'— represents both —$C(O)_2$R'— and —R'$C(O)_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R" R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R" R'")=NR"", —NR—C(NR'R")=NR'", —S(O)R', —$S(O)_2$R', —$S(O)_2$NR'R", —$NRSO_2$R', —CN and —$NO_2$, in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R" R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R" R'")=NR"", —NR—C(NR'R")=NR'", —S(O)R', —$S(O)_2$R', —$S(O)_2$NR'R", —$NRSO_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" is meant to include oxygen (O), nitrogen (N), sulfur (S) and silicon (Si).

Introduction

Erythropoietin (EPO) is a glycoprotein which serves as the principal regulator of red blood cell synthesis. Erythropoietin is produced in the kidney and acts by stimulating precursor cells in the bone marrow causing them to divide and differentiate into mature red blood cells. EPO may exist as a either a 165 or 166 amino acid glycoprotein. The 166 amino acid variant is distinguished from the 165 amino acid variant by the presence of an additional arginine residue at the C-terminal end of the protein.

Recombinant EPO has been available for some time as an effective therapeutic agent in the treatment of various forms of anemia, including anemias associated with chronic renal failure, zidovidine treated HIV infected patients, and cancer patients on chemotherapy. The glycoprotein is administered parenterally, either as an intravenous (IV) or subcutaneous (SC) injection.

To improve the effectiveness of recombinant Erythropoetin used for therapeutic purposes, the present invention provides conjugates of glycosylated and unglycosylated erythropoietin peptides. The conjugates may be additionally modified by further conjugation with diverse species such as therapeutic moieties, diagnostic moieties, targeting moieties and the like.

The conjugates of the invention are formed by the enzymatic attachment of a modified sugar to the glycosylated or unglycosylated peptide. Glycosylation sites provide loci for conjugating modifying groups to the peptide, e.g., by glycoconjugation. An exemplary modifying group is a water-soluble polymer, such as poly(ethylene glycol), e.g., methoxy-poly(ethylene glycol). Modification of the EPO peptides can improve the stability and retention time of the recombinant EPO in a patient's circulation, or reduce the antigenicity of recombinant EPO.

The methods of the invention make it possible to assemble peptides and glycopeptides that have a substantially homogeneous derivatization pattern. The enzymes used in the invention are generally selective for a particular amino acid residue, combination of amino acid residues, or particular glycosyl residues of the peptide. The methods are also practical for large-scale production of modified peptides and glycopeptides. Thus, the methods of the invention provide a practical means for large-scale preparation of glycopeptides having preselected uniform derivatization patterns.

The present invention also provides conjugates of glycosylated and unglycosylated peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent.

The Conjugates

In a first aspect, the present invention provides a conjugate between a selected modifying group and an EPO peptide.

The link between the peptide and the modifying group includes a glycosyl linking group interposed between the peptide and the selected moiety. As discussed herein, the selected moiety is essentially any species that can be attached to a saccharide unit, resulting in a "modified sugar" that is recognized by an appropriate transferase enzyme, which appends the modified sugar onto the peptide. The saccharide component of the modified sugar, when interposed between the peptide and a selected moiety, becomes a "glycosyl linking group," e.g., an "intact glycosyl linking group." The glycosyl linking group is formed from any mono- or oligosaccharide that, after modification with the modifying group, is a substrate for an enzyme that adds the modified sugar to an amino acid or glycosyl residue of a peptide.

The glycosyl linking group can be, or can include, a saccharide moiety that is degradatively modified before or during the addition of the modifying group. For example, the glycosyl linking group can be derived from a saccharide residue that is produced by oxidative degradation of an intact saccharide to the corresponding aldehyde, e.g., via the action of metaperiodate, and subsequently converted to a Schiff base with an appropriate amine, which is then reduced to the corresponding amine.

The conjugates of the invention will typically correspond to the general structure:

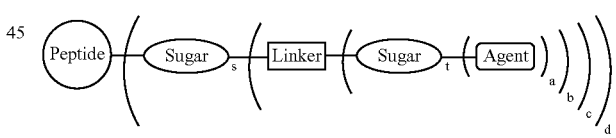

in which the symbols a, b, c, d and s represent a positive, non-zero integer; and t is either 0 or a positive integer. The "agent" is a therapeutic agent, a bioactive agent, a detectable label, water-soluble moiety (e.g., PEG, m-PEG, PPG, and m-PPG) or the like. The "agent" can be a peptide, e.g., enzyme, antibody, antigen, etc. The linker can be any of a wide array of linking groups, infra. Alternatively, the linker may be a single bond or a "zero order linker."

In an exemplary embodiment, the selected modifying group is a water-soluble polymer, e.g., m-PEG. The water-soluble polymer is covalently attached to the peptide via a glycosyl linking group. The glycosyl linking group is covalently attached to an amino acid residue or a glycosyl residue of the peptide. The invention also provides conjugates in which an amino acid residue and a glycosyl residue are modified with a glycosyl linking group.

An exemplary water-soluble polymer is poly(ethylene glycol), e.g., methoxy-poly(ethylene glycol). The poly(ethylene glycol) used in the present invention is not restricted to any particular form or molecular weight range. For unbranched poly(ethylene glycol) molecules the molecular weight is preferably between 500 and 100,000. A molecular weight of 2000-60,000 is preferably used and preferably of from about 5,000 to about 30,000.

In another embodiment the poly(ethylene glycol) is a branched PEG having more than one PEG moiety attached. Examples of branched PEGs are described in U.S. Pat. No. 5,932,462; U.S. Pat. No. 5,342,940; U.S. Pat. No. 5,643,575; U.S. Pat. No. 5,919,455; U.S. Pat. No. 6,113,906; U.S. Pat. No. 5,183,660; WO 02/09766; Kodera Y., *Bioconjugate Chemistry* 5: 283-288 (1994); and Yamasaki et al., *Agric. Biol. Chem.*, 52: 2125-2127, 1998. In a preferred embodiment the molecular weight of each poly(ethylene glycol) of the branched PEG is equal to or greater than about 40,000 daltons.

In addition to providing conjugates that are formed through an enzymatically added glycosyl linking group, the present invention provides conjugates that are highly homogenous in their substitution patterns. Using the methods of the invention, it is possible to form peptide conjugates in which essentially all of the modified sugar moieties across a population of conjugates of the invention are attached to multiple copies of a structurally identical amino acid or glycosyl residue. Thus, in a second aspect, the invention provides a peptide conjugate having a population of water-soluble polymer moieties, which are covalently bound to the peptide through an intact glycosyl linking group. In a preferred conjugate of the invention, essentially each member of the population is bound via the glycosyl linking group to a glycosyl residue of the peptide, and each glycosyl residue of the peptide to which the glycosyl linking group is attached has the same structure.

Also provided is a peptide conjugate having a population of water-soluble polymer moieties covalently bound thereto through a glycosyl linking group. In a preferred embodiment, essentially every member of the population of water soluble polymer moieties is bound to an amino acid residue of the peptide via a glycosyl linking group, and each amino acid residue having a glycosyl linking group attached thereto has the same structure.

The present invention also provides conjugates analogous to those described above in which the peptide is conjugated to a therapeutic moiety, diagnostic moiety, targeting moiety, toxin moiety or the like via an intact glycosyl linking group. Each of the above-recited moieties can be a small molecule, natural polymer (e.g., polypeptide) or synthetic polymer.

Essentially any erythropoietin peptide having any sequence is of use as a component of the conjugates of the present invention. In an exemplary embodiment, the peptide has the sequence:

```
H₂N-APPRLI^CDSR VLERYLLEAK EAE^NITTG^CA    (SEQ ID NO:1)
EH^CSLNE^NIT VPDTKVNFYA WKRMEVGQQA
VEVWQGLALL SEAVLRGQAL LV^NSSQPWEP
LQLHVDKAVS GLRSLTTLLR ALGAQKEAIS
PPDAA^SAAPL RTITADTFRK LFRVYSNFLR
GKLKLYTGEA ^CRTGD-COOH.
```

In another exemplary embodiment the peptide has the sequence:

```
H₂N-APPRLI^CDSR VLERYLLEAK EAE^NITTG^CA    (SEQ ID NO:2)
EH^CSLNE^NIT VPDTKVNFYA WKRMEVGQQA
VEVWQGLALL SEAVLRGQAL LV^NSSQPWEP
LQLHVDKAVS GLRSLTTLLR ALGAQKEAIS
PPDAA^SAAPL RTITADTFRK LFRVYSNFLR
GKLKLYTGEA ^CRTGDR-COOH.
```

In the sequences set forth above, there are two disulfide bonds, one at C7-C161 and another at C29-C33. The cysteine residues are shown above in bold italics.

Preferably, neither terminus is derivatized.

The peptides of the invention include at least one N-linked or O-linked glycosylation site, which is glycosylated with a glycosyl residue that includes a PEG moiety. The PEG is covalently attached to the peptide via an intact glycosyl linking group. The glycosyl linking group is covalently attached to either an amino acid residue or a glycosyl residue of the peptide. Alternatively, the glycosyl linking group is attached to one or more glycosyl units of a glycopeptide. The invention also provides conjugates in which the glycosyl linking group is attached to both an amino acid residue and a glycosyl residue.

The PEG moiety is attached to an intact glycosyl linker directly, or via a non-glycosyl linker, e.g., substituted or unsubstituted alkyl, substituted or unsubstituted heteroalkyl.

In a preferred embodiment, the erythropoietin peptide comprises the moiety shown in Formula I

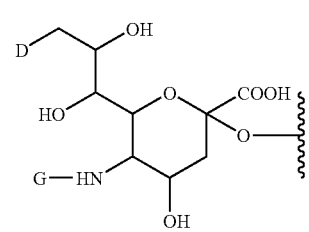

Formula I

In Formula I, D is a member selected from —OH and $R^1$-L-HN—; G is a member selected from $R^1$-L- and —C(O)($C_1$-$C_6$)alkyl; $R^1$ is a moiety comprising a member selected a moiety comprising a straight-chain or branched poly(ethylene glycol) residue; and L is a linker which is a member selected from a bond, substituted or unsubstituted alkyl and substituted or unsubstituted heteroalkyl, such that when D is OH, G is $R^1$-L-, and when G is —C(O)($C_1$-$C_6$)alkyl, D is $R^1$-L-NH—.

The Compositions

As discussed above, the invention provides saccharides bearing a modifying group, activated analogues of these species and conjugates formed between species such as peptides and lipids and a modified saccharide of the invention.

Modified Sugars

The present invention provides modified sugars, modified sugar nucleotides and conjugates of the modified sugars. In modified sugar compounds of the invention, the sugar moiety is preferably a saccharide, a deoxy-saccharide, an amino-saccharide, or an N-acyl saccharide. The term "saccharide" and its equivalents, "saccharyl," "sugar," and "glycosyl" refer to monomers, dimers, oligomers and polymers. The sugar moiety is also functionalized with a modifying group. The modifying group is conjugated to the sugar moiety, typically, through conjugation with an amine, sulfhydryl or hydroxyl, e.g., primary hydroxyl, moiety on the sugar. In an exemplary embodiment, the modifying group is attached through an amine moiety on the sugar, e.g., through an amide, a urethane or a urea that is formed through the reaction of the amine with a reactive derivative of the modifying group.

Any sugar can be utilized as the sugar core of the conjugates of the invention. Exemplary sugar cores that are useful in forming the compositions of the invention include, but are not limited to, glucose, galactose, mannose, fucose, and sialic acid. Other useful sugars include amino sugars such as glucosamine, galactosamine, mannosamine, the 5-amine analogue of sialic acid and the like. The sugar core can be a structure found in nature or it can be modified to provide a site for conjugating the modifying group. For example, in one embodiment, the invention provides a sialic acid derivative in which the 9-hydroxy moiety is replaced with an amine. The amine is readily derivatized with an activated analogue of a selected modifying group.

In the discussion that follows the invention is illustrated by reference to the use of selected derivatives of sialic acid. Those of skill in the art will recognize that the focus of the discussion is for clarity of illustration and that the structures and compositions set forth are generally applicable across the genus of saccharide groups, modified saccharide groups, activated modified saccharide groups and conjugates of modified saccharide groups.

In an exemplary embodiment, the invention provides a modified sugar amine that has the formula:

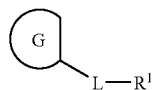

in which G is a glycosyl moiety, L is a bond or a linker and $R^1$ is the modifying group. Exemplary bonds are those that are formed between a reactive group on the glycosyl moiety, e.g., $NH_2$, SH, or OH, and a group of complementary reactivity on the modifying group. Thus, exemplary bonds include, but are not limited to $NHR^1$, $OR^1$, $SR^1$ and the like. For example, when $R^1$ includes a carboxylic acid moiety, this moiety may be activated and coupled with an $NH_2$ moiety on the glycosyl residue affording a bond having the structure $NHC(O)R^1$. Similarly, the OH and SH groups can be converted to the corresponding ether or thioether derivatives, respectively.

Exemplary linkers include alkyl and heteroalkyl moieties. The linkers include linking groups, for example acyl-based linking groups, e.g., —C(O)NH—, —OC(O)NH—, and the like. The linking groups are bonds formed between components of the species of the invention, e.g., between the glycosyl moiety and the linker (L), or between the linker and the modifying group ($R^1$). Other linking groups are ethers, thioethers and amines. For example, in one embodiment, the linker is an amino acid residue, such as a glycine residue. The carboxylic acid moiety of the glycine is converted to the corresponding amide by reaction with an amine on the glycosyl residue, and the amine of the glycine is converted to the corresponding amide or urethane by reaction with an activated carboxylic acid or carbonate of the modifying group.

Another exemplary linker is a PEG moiety or a PEG moiety that is functionalized with an amino acid residue. The PEG is to the glycosyl group through the amino acid residue at one PEG terminus and bound to $R^1$ through the other PEG terminus. Alternatively, the amino acid residue is bound to $R^1$ and the PEG terminus not bound to the amino acid is bound to the glycosyl group.

An exemplary species for L-$R^1$ has the formula: —NH{C(O)$(CH_2)_a$NH}$_s${C(O)$(CH_2)_b(OCH_2CH_2)_cO(CH_2)_d$NH}$_t R^1$, in which the indeces s and t are independently 0 or 1. The indeces a, b and d are independently integers from 0 to 20, and c is an integer from 1 to 2500. Other similar linkers are based on species in which the —NH moiety is replaced by, for example, —S, —O and —$CH_2$.

More particularly, the invention provides compounds in which L-$R^1$ is: NHC(O)$(CH_2)_a$NHC(O)$(CH_2)_b(OCH_2CH_2)_c$O$(CH_2)_d$NHR$^1$, NHC(O)$(CH_2)_b(OCH_2CH_2)_cO(CH_2)_d$NHR$^1$, NHC(O)O$(CH_2)_b(OCH_2CH_2)_cO(CH_2)_d$NHR$^1$, NH$(CH_2)_a$NHC(O)$(CH_2)_b(OCH_2CH_2)_cO(CH_2)_d$NHR$^1$, NHC(O)$(CH_2)_a$NHR$^1$, NH$(CH_2)_a$NHR$^1$, and NHR$^1$. In these formulae, the indeces a, b and d are independently selected from the integers from 0 to 20, preferably from 1 to 5. The index c is an integer from 1 to 2500.

In an illustrative embodiment, G is sialic acid and selected compounds of the invention have the formulae:

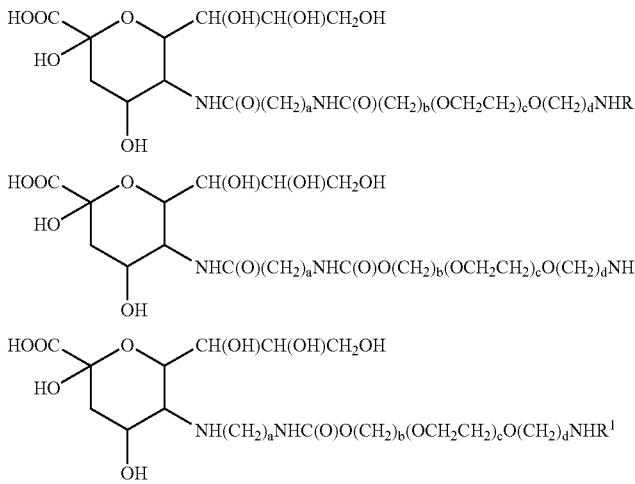

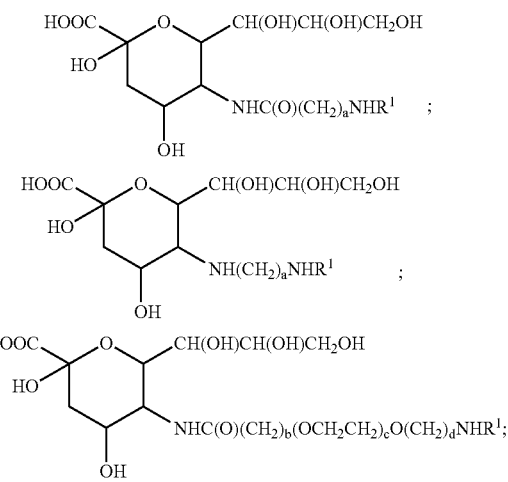

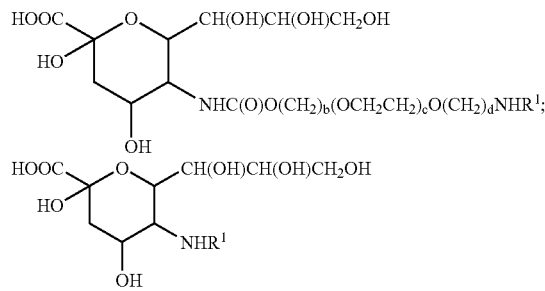

As those of skill in the art will appreciate, the sialic acid moiety in the exemplary compounds above can be replaced with any other amino-saccharide including, but not limited to, glucosamine, galactosamine, mannosamine, their N-acetyl derivatives, and the like.

In another illustrative embodiment, a primary hydroxyl moiety of the sugar is functionalized with the modifying group. For example, the 9-hydroxyl of sialic acid can be converted to the corresponding amine and functionalized to provide a compound according to the invention. Formulae according to this embodiment include:

In a further exemplary embodiment, the invention provides modified sugars in which the 6-hydroxyl position is converted to the corresponding amine moiety, which bears a linker-modifying group cassette such as those set forth above. Exemplary saccharyl groups that can be used as the core of these modified sugars include Gal, GalNAc, Glc, GlcNAc, Fuc, Xyl, Man, and the like. A representative modified sugar according to this embodiment has the formula:

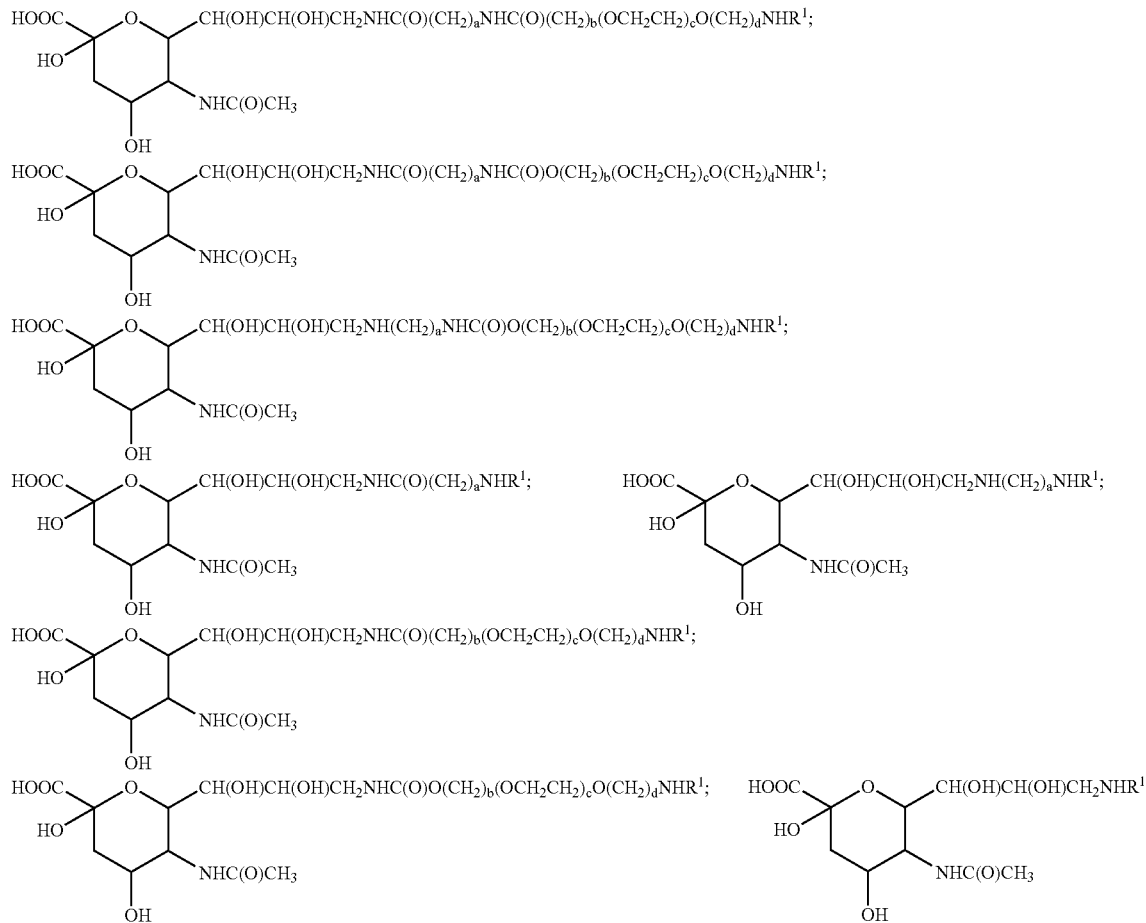

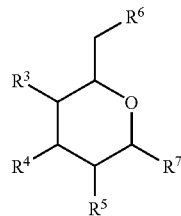

thereof. In a preferred embodiment, the modified sugar nucleotide is selected from a UDP-glycoside, CMP-glycoside, or a GDP-glycoside. Even more preferably, the sugar nucleotide portion of the modified sugar nucleotide is selected from UDP-galactose, UDP-galactosamine, UDP-glucose, UDP-glucosamine, GDP-mannose, GDP-fucose, CMP-sialic acid, or CMP-NeuAc. In an exemplary embodiment, the nucleotide phosphate is attached to C-1.

Thus, in an illustrative embodiment in which the glycosyl moiety is sialic acid, the invention provides compounds having the formulae:

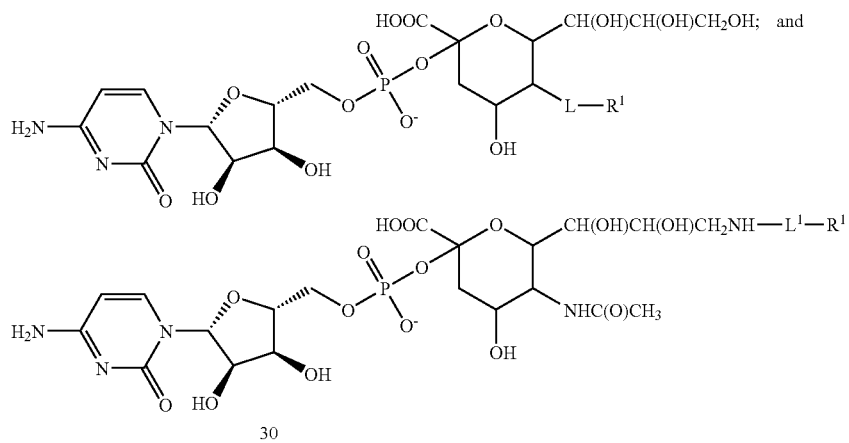

in which $R^3$-$R^5$ and $R^7$ are members independently selected from H, OH, C(O)CH$_3$, NH, and NH C(O)CH$_3$. $R^6$ is $OR^1$, $NHR^1$ or L-$R^1$, which is as described above.

Selected conjugates of the invention are based on mannose, galactose or glucose, or on species having the stereochemistry of mannose, galactose or glucose. The general formulae of these conjugates are:

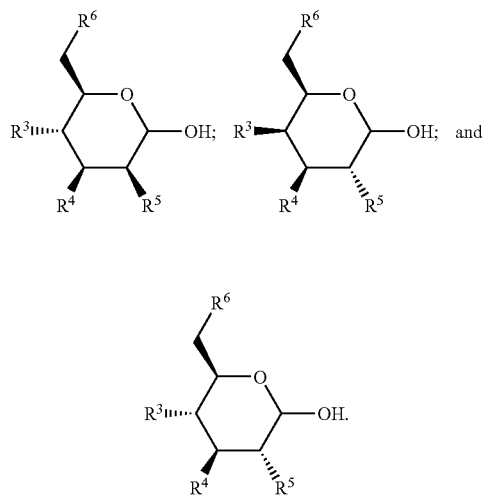

Figure 2:
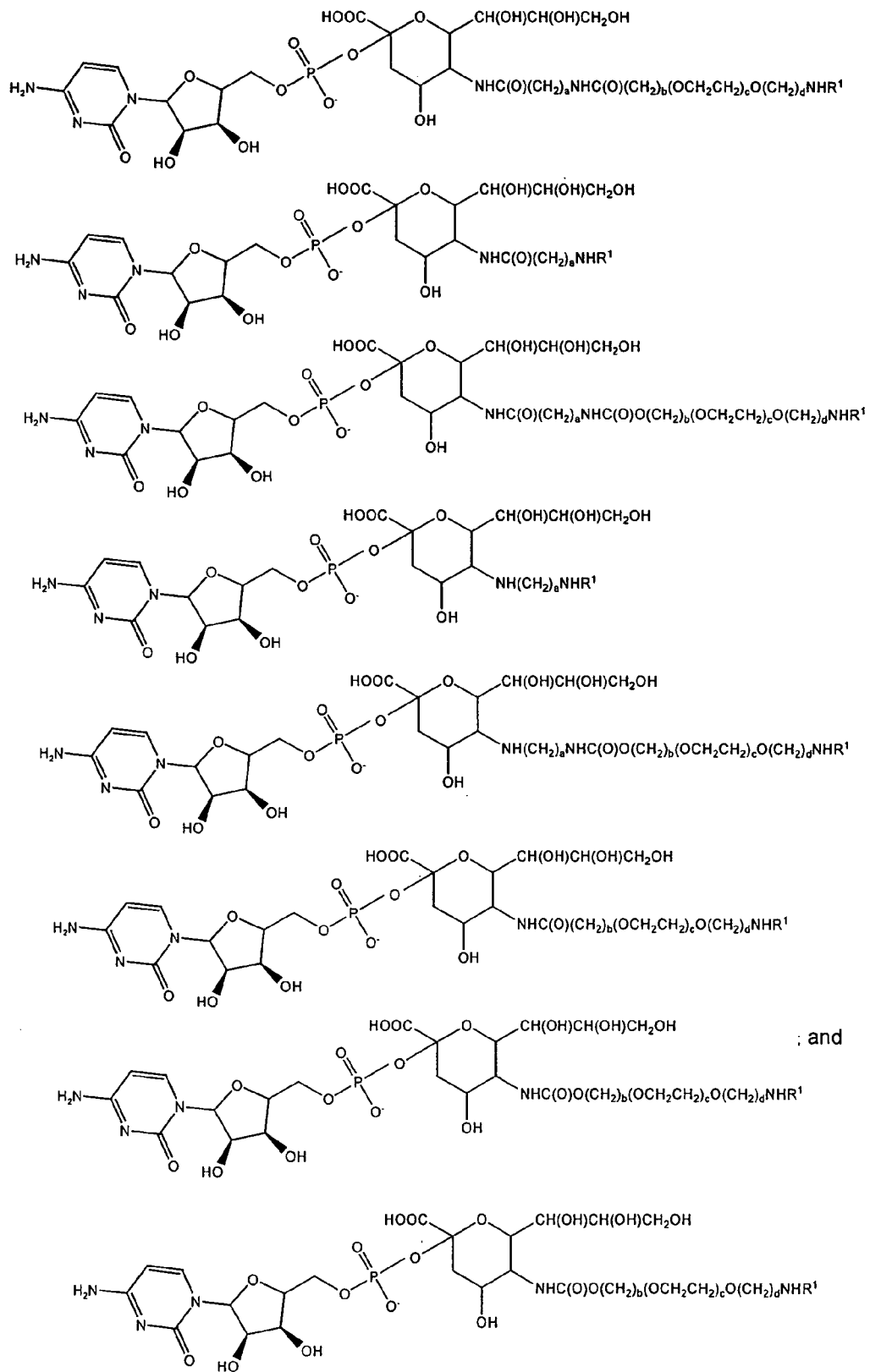
FIG. 2.

In another exemplary embodiment, the invention provides compounds as set forth above that are activated as the corresponding nucleotide sugars. Exemplary sugar nucleotides that are used in the present invention in their modified form include nucleotide mono-, di- or triphosphates or analogs in which L-$R^1$ is as discussed above, and $L^1$-$R^1$ represents a linker bound to the modifying group. As with L, exemplary linker species according to $L^1$ include a bond, alkyl or heteroalkyl moieties. Exemplary modified sugar nucleotide compounds according to these embodiments are set forth in FIG. 1 and FIG. 2.

In another exemplary embodiment, the invention provides a conjugate formed between a modified sugar of the invention and a substrate, e.g., a peptide, lipid, aglycone, etc., more particularly between a modified sugar and a glycosyl residue of a glycopeptide or a glycolipid. In this embodiment, the sugar moiety of the modified sugar becomes a glycosyl linking group interposed between the substrate and the modifying group. An exemplary glycosyl linking group is an intact glycosyl linking group, in which the glycosyl moiety or moieites forming the linking group are not degraded by chemical (e.g., sodium metaperiodate) or enzymatic processes (e.g., oxidase). Selected conjugates of the invention include a modifying group that is attached to the amine moiety of an aminosaccharide, e.g., mannosamine, glucosamine, galactosamine, sialic acid etc. Exemplary modifying group-intact glycosyl linking group cassette according to this motif is based on a sialic acid structure, such as that having the formulae:

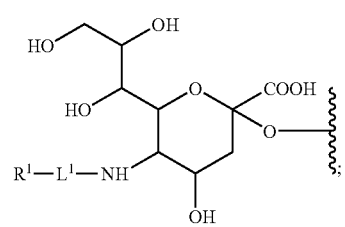

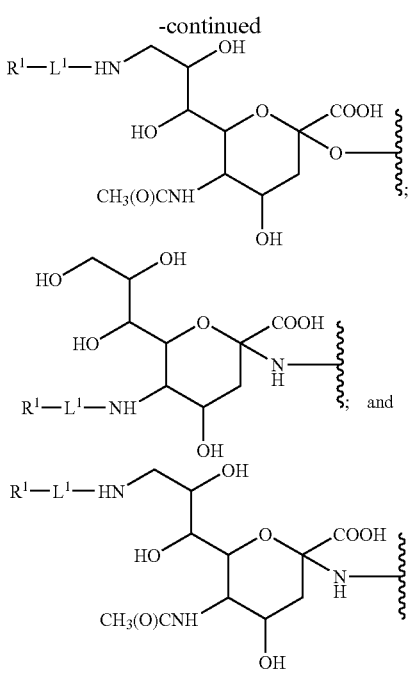

In the formulae above, $R^1$, $L^1$ and $L^2$ are as described above.

In still a further exemplary embodiment, the conjugate is formed between a substrate and the 1-position of a saccharyl moiety that in which the modifying group is attached through a linker at the 6-carbon position of the saccharyl moiety. Thus, illustrative conjugates according to this embodiment have the formulae:

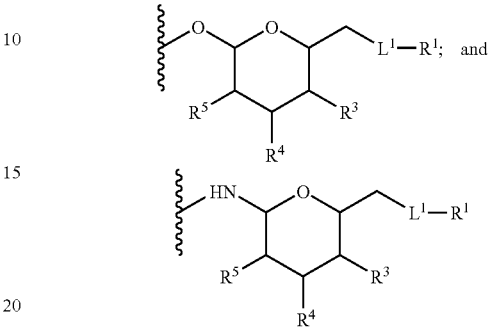

in which the radicals are as discussed above. Those of skill will appreciate that the modified saccharyl moieties set forth above can also be conjugated to a substrate at the 2, 3, 4, or 5 carbon atoms.

Illustrative compounds according to this embodiment include compounds having the formulae:

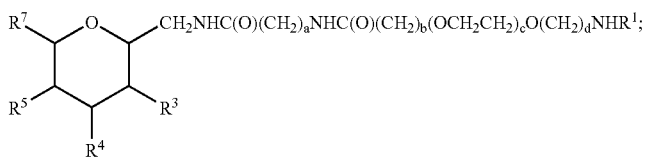

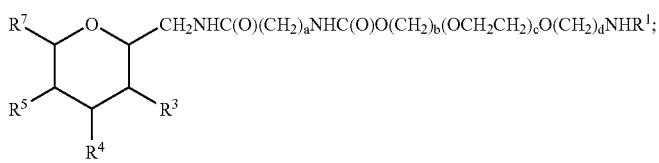

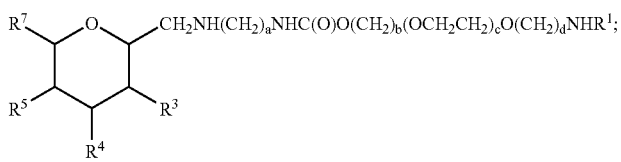

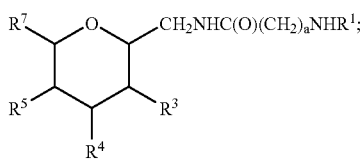

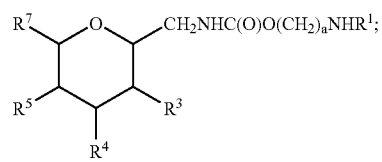

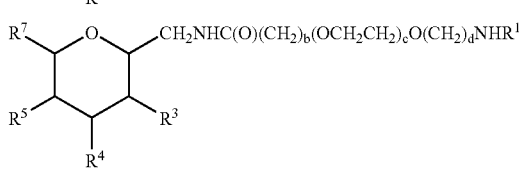

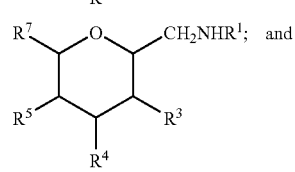

-continued

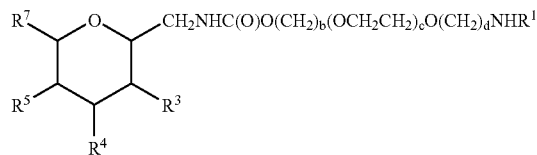

in which the R groups and the indeces are as described above.

The invention also provides sugar nucleotides modified with L-R$^1$ at the 6-carbon position. Exemplary species according to this embodiment include:

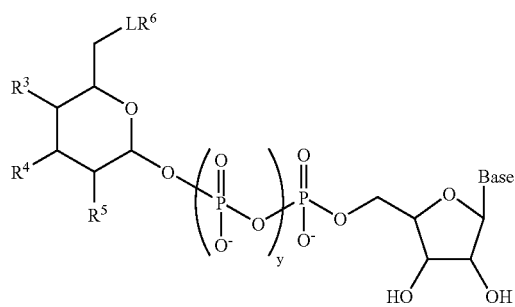

in which the R groups, and L, represent moieties as discussed above. The index "y" is 0, 1 or 2.

A further exemplary nucleotide sugar of the invention, based on a species having the stereochemistry of GDP mannose. An exemplary species according to this embodiment has the structure:

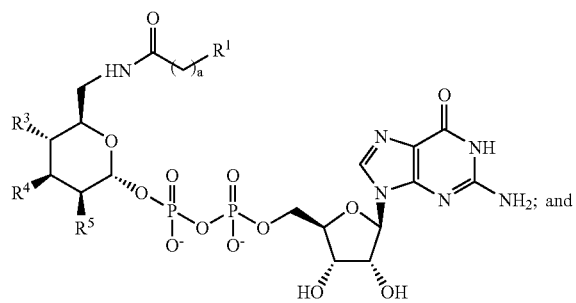

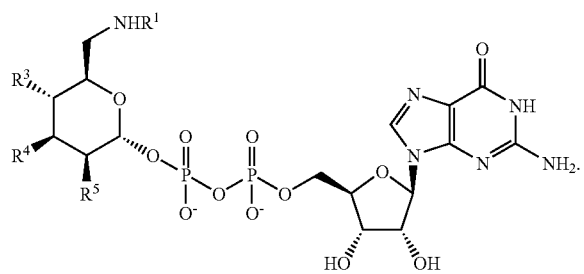

In a still further exemplary embodiment, the invention provides a conjugate, based on the stereochemistry of UDP galactose. An exemplary compound according to this embodiment has the structure:

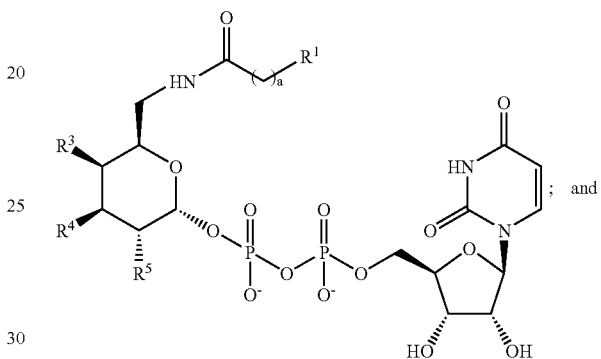

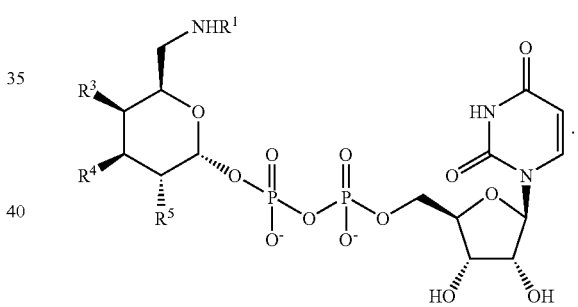

In another exemplary embodiment, the nucleotide sugar is based on the stereochemistry of glucose. Exemplary species according to this embodiment have the formulae:

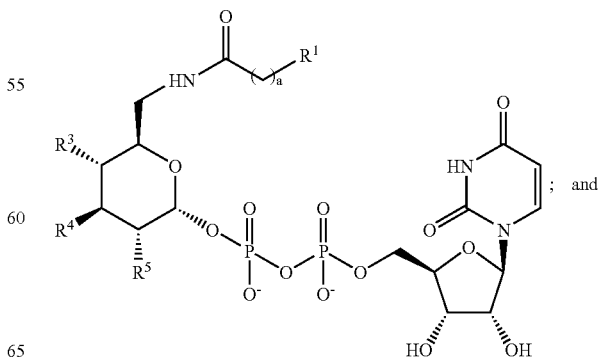

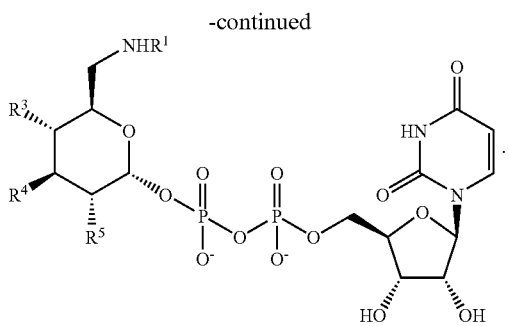

The modifying group, $R^1$, is any of a number of species including, but not limited to, water-soluble polymers, water-insoluble polymers, therapeutic agents, diagnostic agents and the like. The nature of exemplary modifying groups is discussed in greater detail hereinbelow.

Modifying Groups

Water-Soluble Polymers

Many water-soluble polymers are known to those of skill in the art and are useful in practicing the present invention. The term water-soluble polymer encompasses species such as saccharides (e.g., dextran, amylose, hyaluronic acid, poly (sialic acid), heparans, heparins, etc.); poly (amino acids), e.g., poly(aspartic acid) and poly(glutamic acid); nucleic acids; synthetic polymers (e.g., poly(acrylic acid), poly (ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Preferred water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002). Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine).

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly (ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly (ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

The art-recognized methods of polymer activation set forth above are of use in the context of the present invention in the formation of the branched polymers set forth herein and also for the conjugation of these branched polymers to other species, e.g., sugars, sugar nucleotides and the like.

Exemplary poly(ethylene glycol) molecules of use in the invention include, but are not limited to, those having the formula:

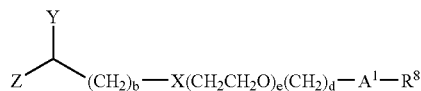

in which $R^8$ is H, OH, $NH_2$, substituted or unsubstituted alkyl, substituted or unsubstituted aryl, substituted or unsubstituted heteroaryl, substituted or unsubstituted heterocycloalkyl, substituted or unsubstituted heteroalkyl, e.g., acetal, OHC—, $H_2N$—$(CH_2)_q$—, HS—$(CH_2)_q$, or —$(CH_2)_qC(Y)Z^1$. The index "e" represents an integer from 1 to 2500. The indeces b, d, and q independently represent integers from 0 to 20. The symbols Z and $Z^1$ independently represent OH, $NH_2$, leaving groups, e.g., imidazole, p-nitrophenyl, HOBT, tetrazole, halide, S—$R^9$, the alcohol portion of activated esters; —$(CH_2)_pC(Y^1)V$, or —$(CH_2)_pU(CH_2)_sC(Y^1)_v$. The symbol Y represents H(2), =O, =S, =N—$R^{10}$. The symbols X, Y, $Y^1$, $A^1$, and U independently represent the moieties O, S, N—$R^{11}$. The symbol V represents OH, $NH_2$, halogen, S—$R^{12}$, the alcohol component of activated esters, the amine component of activated amides, sugar-nucleotides, and proteins. The indeces p, q, s and v are members independently selected from the integers from 0 to 20. The symbols $R^9$, $R^{10}$, $R^{11}$ and $R^{12}$ independently represent H, substituted or unsubstituted alkyl, substituted or unsubstituted heteroalkyl, substituted or unsubstituted aryl, substituted or unsubstituted heterocycloalkyl and substituted or unsubstituted heteroaryl.

In other exemplary embodiments, the poly(ethylene glycol) molecule is selected from the following:

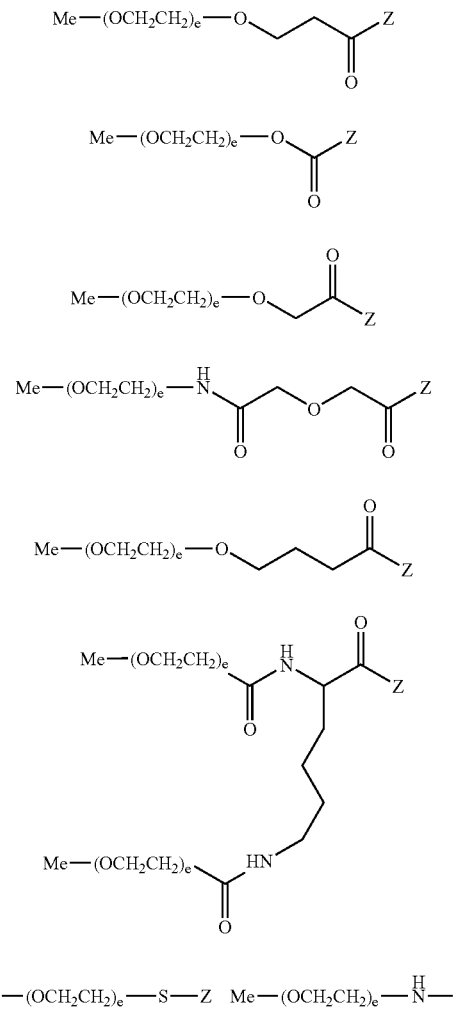

The poly(ethylene glycol) useful in forming the conjugate of the invention is either linear or branched. Branched poly(ethylene glycol) molecules suitable for use in the invention include, but are not limited to, those described by the following formula:

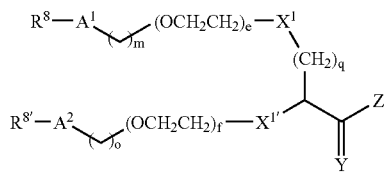

in which $R^8$ and $R^{8'}$ are members independently selected from the groups defined for $R^8$, above. $A^1$ and $A^2$ are members independently selected from the groups defined for $A^1$, above. The indeces e, f, o, and q are as described above. Z and Y are as described above. $X^1$ and $X^{1'}$ are members independently selected from S, SC(O)NH, HNC(O)S, SC(O)O, O, NH, NHC(O), (O)CNH and NRC(O)O, OC(O)NH.

In other exemplary embodiments, the branched PEG is based upon a cysteine, serine or di-lysine core. Thus, further exemplary branched PEGs include:

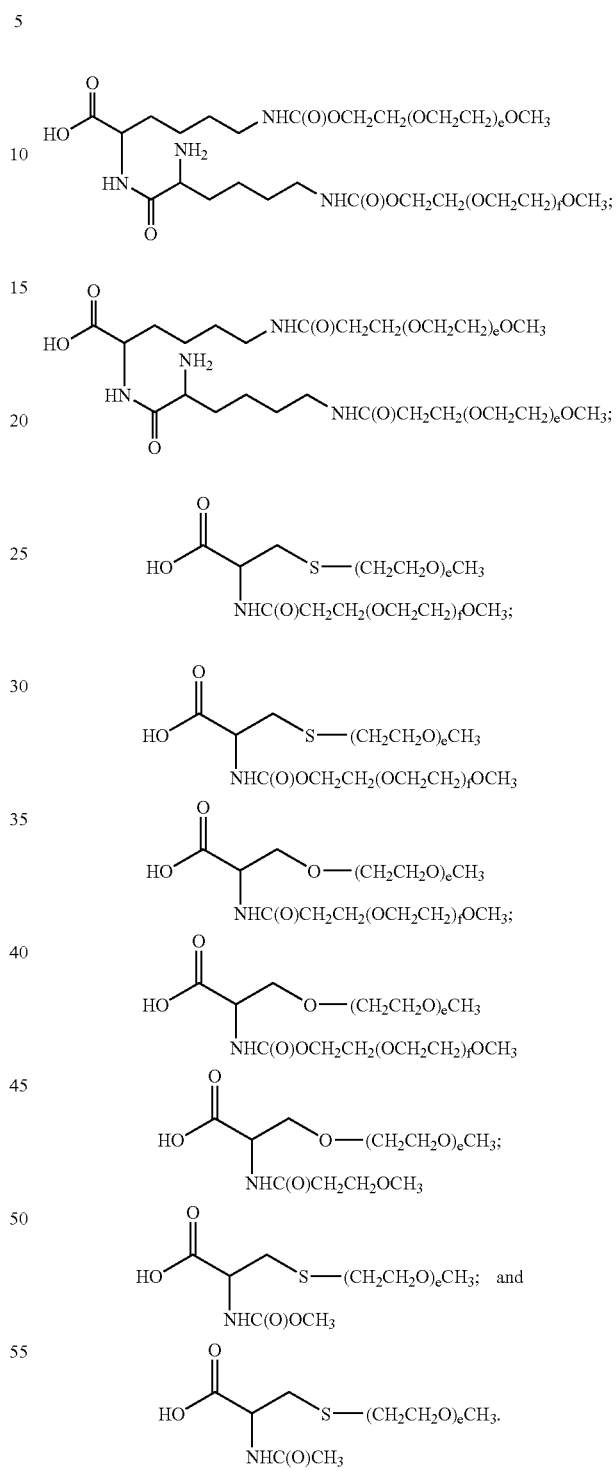

In yet another embodiment, the branched PEG moiety is based upon a tri-lysine peptide. The tri-lysine can be mono-, di-, tri-, or tetra-PEG-ylated. Exemplary species according to this embodiment have the formulae:

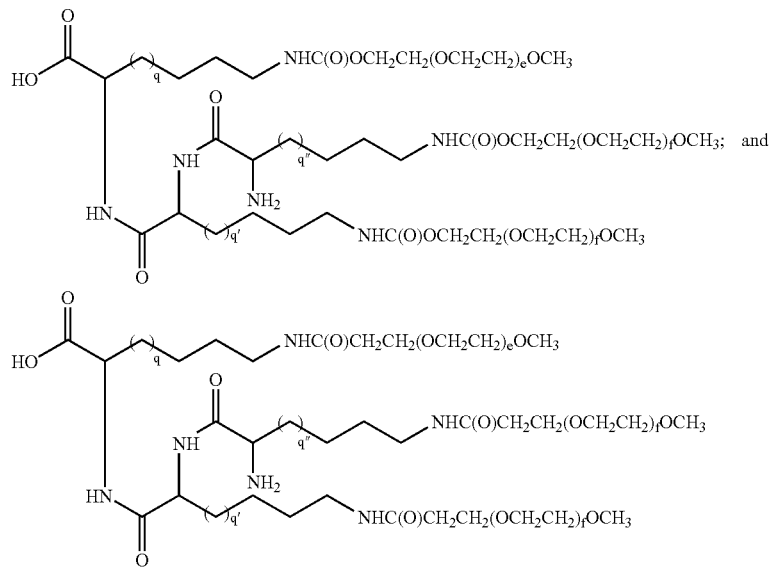

in which e, f and f, are independently selected integers from 1 to 2500; and q, q' and q" are independently selected integers from 1 to 20.

In exemplary embodiments of the invention, the PEG is m-PEG (5 kD, 10 kD, or 20 kD). An exemplary branched PEG species is a serine- or cysteine-(m-PEG)$_2$ in which the m-PEG is a 20 kD m-PEG.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits is within the scope of the invention.

Specific embodiments according to the invention include:

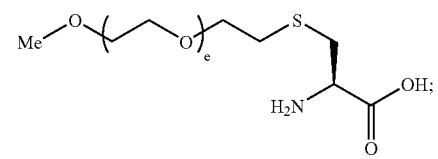

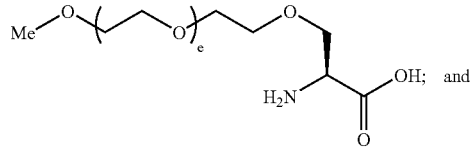

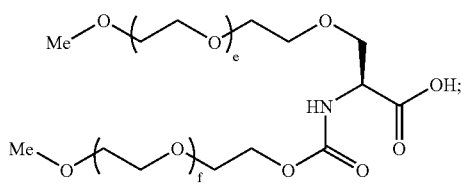

and carbonates and active esters of these species, such as:

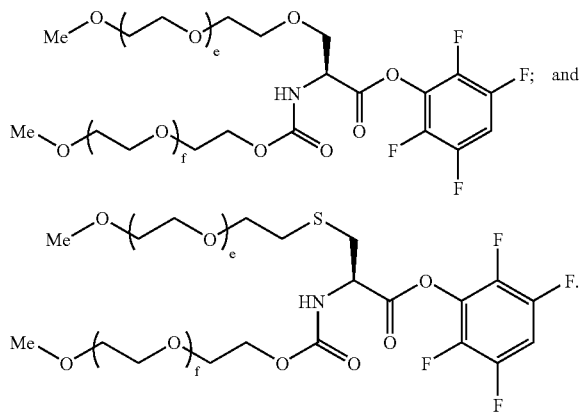

Other activating, or leaving groups, appropriate for activating linear and branched PEGs of use in preparing the compounds set forth herein include, but are not limited to the species:

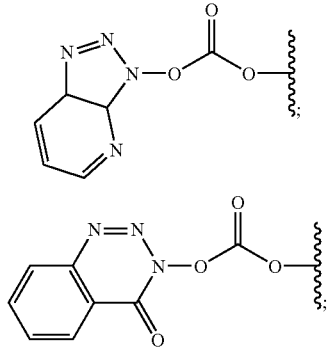

-continued

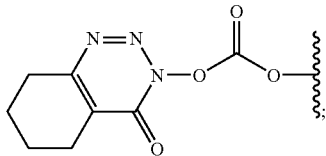

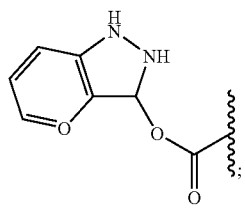

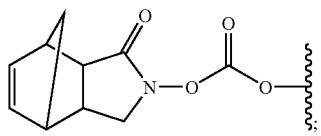

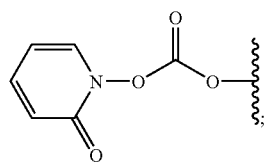

-continued

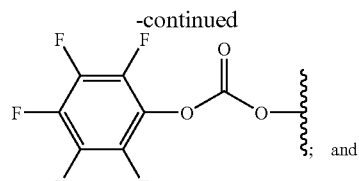; and

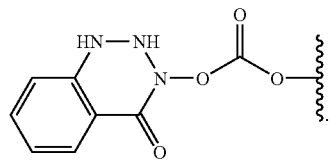.

PEG molecules that are activated with these and other species and methods of making the activated PEGs are set forth in WO 04/083259.

Those of skill in the art will appreciate that one or more of the m-PEG arms of the branched polymer can be replaced by a PEG moiety with a different terminus, e.g., OH, COOH, NH$_2$, C$_2$-C$_{10}$-alkyl, etc. Moreover, the structures above are readily modified by inserting alkyl linkers (or removing carbon atoms) between the α-carbon atom and the functional group of the side chain. Thus, "homo" derivatives and higher homologues, as well as lower homologues are within the scope of cores for branched PEGs of use in the present invention.

The branched PEG species set forth herein are readily prepared by methods such as that set forth in the scheme below:

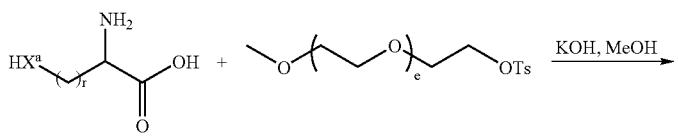

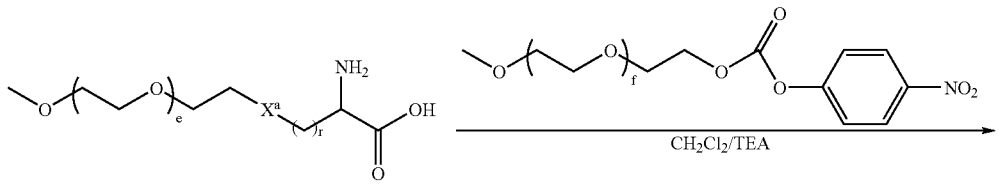

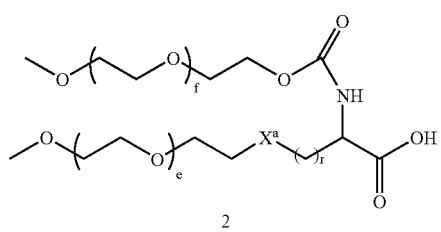

in which $X^a$ is O or S and r is an integer from 1 to 5. The indeces e and f are independently selected integers from 1 to 2500.

Thus, according to this scheme, a natural or unnatural amino acid is contacted with an activated m-PEG derivative, in this case the tosylate, forming 1 by alkylating the side-chain heteroatom $X^a$. The mono-functionalize m-PEG amino acid is submitted to N-acylation conditions with a reactive m-PEG derivative, thereby assembling branched m-PEG 2. As one of skill will appreciate, the tosylate leaving group can be replaced with any suitable leaving group, e.g., halogen, mesylate, triflate, etc. Similarly, the reactive carbonate utilized to acylate the amine can be replaced with an active ester, e.g., N-hydroxysuccinimide, etc., or the acid can be activated in situ using a dehydrating agent such as dicyclohexylcarbodiimide, carbonyldiimidazole, etc.

In an exemplary embodiment, the modifying group is a PEG moiety, however, any modifying group, e.g., water-soluble polymer, water-insoluble polymer, therapeutic moiety, etc., can be incorporated in a glycosyl moiety through an appropriate linkage. The modified sugar is formed by enzymatic means, chemical means or a combination thereof, thereby producing a modified sugar. In an exemplary embodiment, the sugars are substituted with an active amine at any position that allows for the attachment of the modifying moiety, yet still allows the sugar to function as a substrate for an enzyme capable of coupling the modified sugar to the peptide. In an exemplary embodiment, when galactosamine is the modified sugar, the amine moiety is attached to the carbon atom at the 6-position.

The present invention also provides nucleotide sugars in which the sugar moiety is modified. An exemplary modified sugar nucleotide bears a sugar group that is modified through an amine moiety on the sugar. Modified sugar nucleotides, e.g., saccharyl-amine derivatives of a sugar nucleotide, are also of use in the methods of the invention. For example, a saccharyl amine (without the modifying group) can be enzymatically conjugated to a peptide (or other species) and the free saccharyl amine moiety subsequently conjugated to a desired modifying group. Alternatively, the modified sugar nucleotide can function as a substrate for an enzyme that transfers the modified sugar to a saccharyl acceptor on a substrate, e.g., a peptide, glycopeptide, lipid, aglycone, glycolipid, etc.

In one embodiment in which the saccharide core is galactose or glucose, $R^5$ is NHC(O)Y.

In an exemplary embodiment, the modified sugar is based upon a 6-amino-N-acetyl-glycosyl moiety. As shown below for N-acetylgalactosamine, the 6-amino-sugar moiety is readily prepared by standard methods.

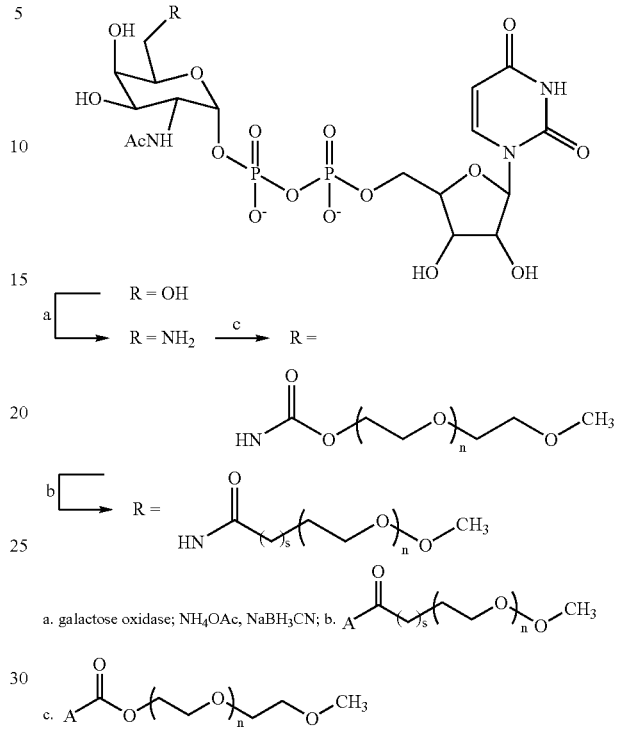

In the scheme above, the index n represents an integer from 1 to 2500, preferably from 10 to 1500, and more preferably from 10 to 1200. The symbol "A" represents an activating group, e.g., a halo, a component of an activated ester (e.g., a N-hydroxysuccinimide ester), a component of a carbonate (e.g., p-nitrophenyl carbonate) and the like. Those of skill in the art will appreciate that other PEG-amide nucleotide sugars are readily prepared by this and analogous methods.

In other exemplary embodiments, the amide moiety is replaced by a group such as a urethane or a urea.

In still further embodiments, $R^1$ is a branched PEG, for example, one of those species set forth above. Illustrative compounds according to this embodiment include:

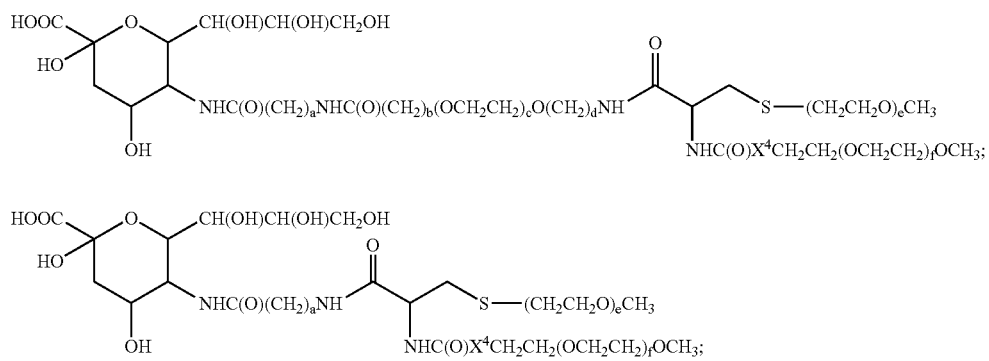

-continued

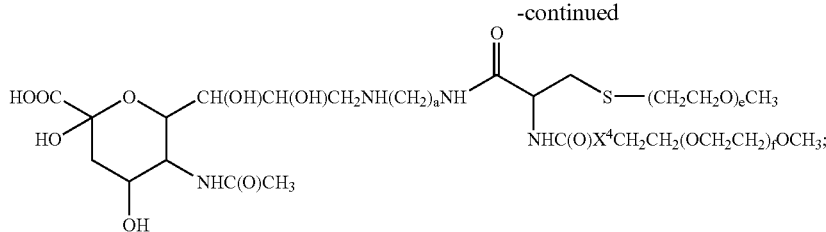

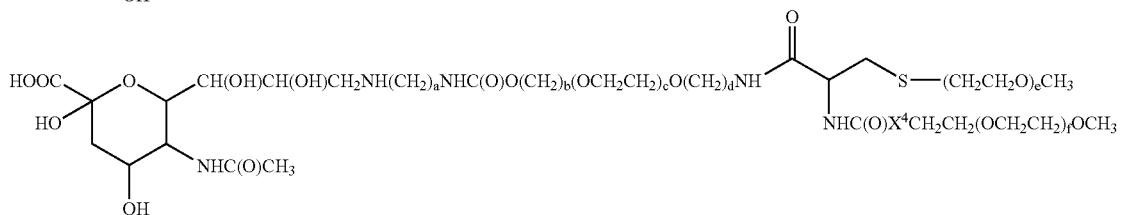

in which $X^4$ is a bond or O.

Moreover, as discussed above, the present invention provides nucleotide sugars that are modified with a water-soluble polymer, which is either straight-chain or branched. For example, compounds having the formula shown below are within the scope of the present invention:

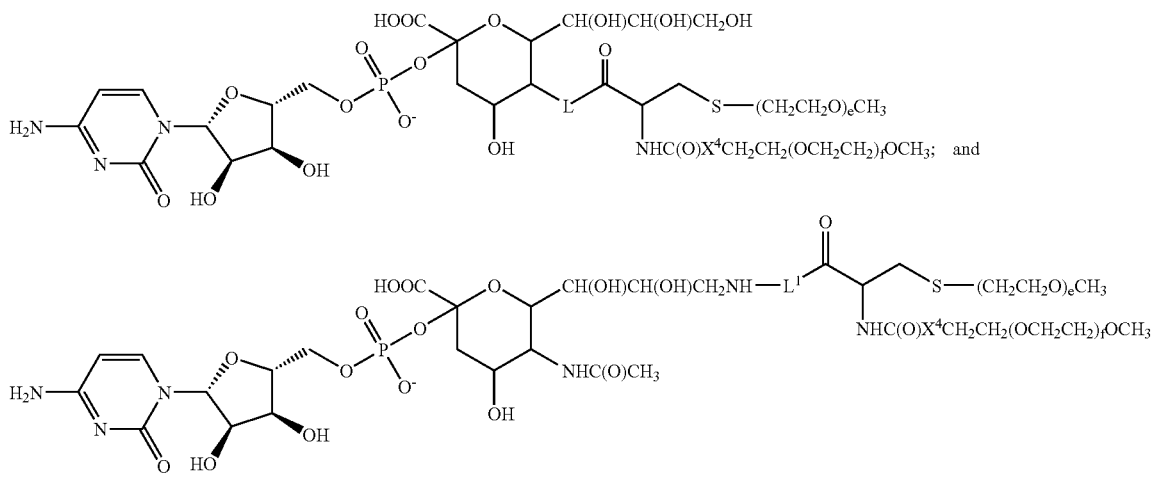

in which $X^4$ is O or a bond.

Similarly, the invention provides nucleotide sugars of those modified sugar species in which the carbon at the 6-position is modified:

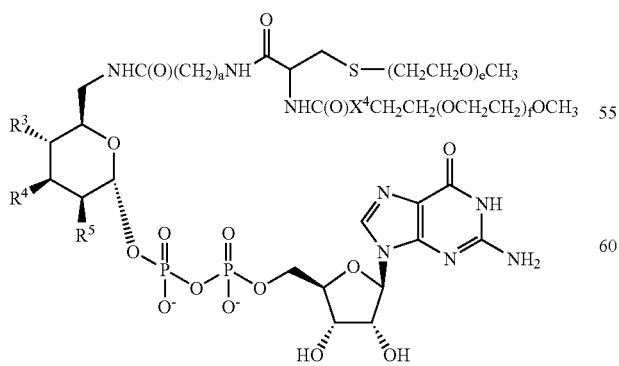

in which $X^4$ is a bond or O.

Also provided are conjugates of peptides and glycopeptides, lipids and glycolipids that include the compositions of the invention. For example, the invention provides conjugates having the following formulae:

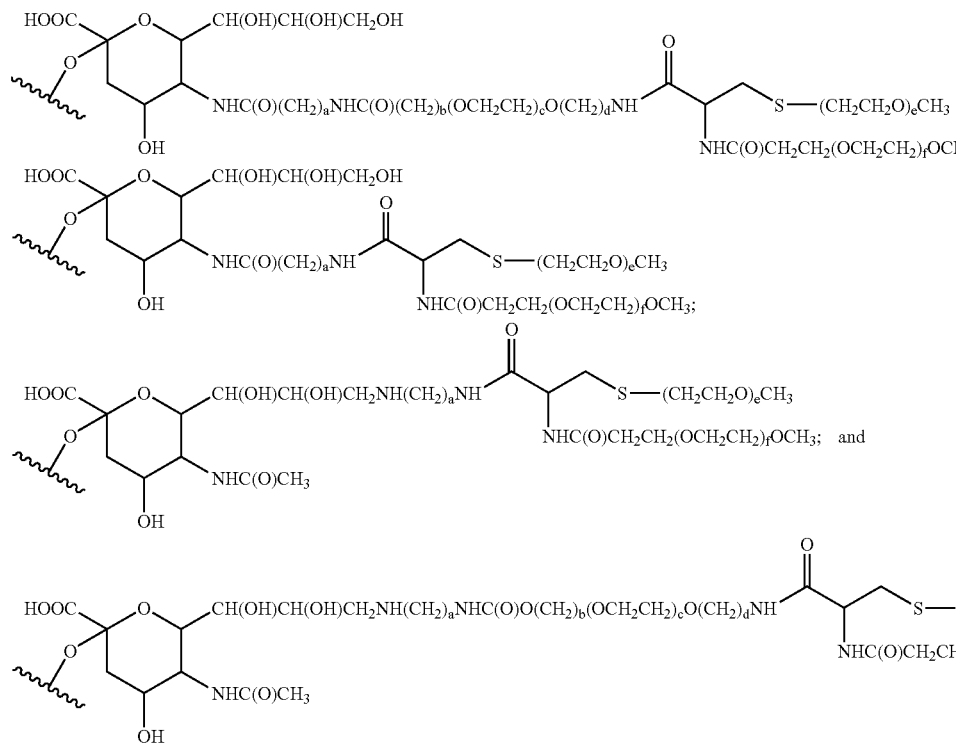

Water-Insoluble Polymers

In another embodiment, analogous to those discussed above, the modified sugars include a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic peptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly (isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, pluronics and polyvinylphenol and copolymers thereof.

Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid" polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly($\alpha$-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J. Biomed. Mater. Res.* 21: 1301-1316 (1987); and Cohn et al., *J. Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly (amino acids), poly(anhydrides), poly(orthoesters), poly (carbonates), poly(phosphazines), poly(phosphoesters), poly (thioesters), polysaccharides and mixtures thereof. More preferably still, the biosresorbable polymer includes a poly (hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other polymers based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a di-functional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene) oxide. Such poly(alkylene) oxides can include, for example, poly(ethylene) oxide, poly (propylene) oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. No. 5,410,016, which issued on Apr. 25, 1995 and 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly (ethylene glycol); whereas, the hydrolytically labile extensions can be a poly($\alpha$-hydroxy acid), such as polyglycolic acid or polylactic acid. See, Sawhney et al., *Macromolecules* 26: 581-587 (1993).

In another preferred embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811, which issued on Jun. 11, 1985. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, are of use in the present invention.

The structural formats discussed above in the context of the water-soluble polymers, both straight-chain and branched are generally applicable with respect to the water-insoluble polymers as well. Thus, for example, the cysteine, serine, dilysine, and trilysine branching cores can be functionalized with two water-insoluble polymer moieties. The methods used to produce these species are generally closely analogous to those used to produce the water-soluble polymers.

The Methods

In addition to the conjugates discussed above, the present invention provides methods for preparing these and other conjugates. Moreover, the invention provides methods of preventing, curing or ameliorating a disease state by administering a conjugate of the invention to a subject at risk of developing the disease or a subject that has the disease.

Thus, the invention provides a method of forming a covalent conjugate between a selected moiety and a peptide, a glycolipid or an aglycone (e.g., ceramide or sphingosine). For clarity of illustration, the invention is illustrated with reference to a conjugate formed between a peptide and the modified glycosyl moiety of an activated modified sugar of the invention. Those of skill will appreciate that the invention equally encompasses methods of forming conjugates of glycolipids, and aglycones with an activated modified sugar of the invention.

In exemplary embodiments, the conjugate is formed between a water-soluble polymer, a therapeutic moiety, targeting moiety or a biomolecule, and a glycosylated or non-glycosylated peptide. The polymer, therapeutic moiety or biomolecule is conjugated to the peptide via a glycosyl linking group, which is interposed between, and covalently linked to both the peptide and the modifying group (e.g., water-soluble polymer). The method includes contacting the peptide with a mixture containing a modified sugar and an enzyme, e.g., a glycosyltransferase, that conjugates the modified sugar to the substrate (e.g., peptide, aglycone, glycolipid). The reaction is conducted under conditions appropriate to form a covalent bond between the modified sugar and the peptide (or other substrate). The sugar moiety of the modified sugar is preferably selected from nucleotide sugars.

The acceptor peptide is typically synthesized de novo, or recombinantly expressed in a prokaryotic cell (e.g., bacterial cell, such as *E. coli*) or in a eukaryotic cell such as a mammalian, yeast, insect, fungal or plant cell. The peptide can be either a full-length protein or a fragment. Moreover, the peptide can be a wild type or mutated peptide. In an exemplary embodiment, the peptide includes a mutation that adds one or more N- or O-linked glycosylation sites to the peptide sequence.

The method of the invention also provides for modification of incompletely glycosylated peptides that are produced recombinantly. Many recombinantly produced glycoproteins are incompletely glycosylated, exposing carbohydrate residues that may have undesirable properties, e.g., immunogenicity, recognition by the RES. Employing a modified sugar in a method of the invention, the peptide can be simultaneously further glycosylated and derivatized with, e.g., a water-soluble polymer, therapeutic agent, or the like. The sugar moiety of the modified sugar can be the residue that would properly be conjugated to the acceptor in a fully glycosylated peptide, or another sugar moiety with desirable properties.

Those of skill will appreciate that the invention can be practiced using substantially any peptide or glycopeptide from any source. Exemplary peptides with which the invention can be practiced are set forth in WO 03/031464, and the references set forth therein.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-acetylgalactosamine, galactose, mannose, GlcNAc, glucose, fucose or xylose) to the hydroxy side chain of a hydroxyamino acid, preferably serine or threonine, although unusual or non-natural amino acids, e.g., 5-hydroxyproline or 5-hydroxylysine may also be used.

Moreover, in addition to peptides, the methods of the present invention can be practiced with other biological structures (e.g., glycolipids, lipids, sphingoids, ceramides, whole cells, and the like, containing a glycosylation site).

Addition of glycosylation sites to a peptide or other structure is conveniently accomplished by altering the amino acid sequence such that it contains one or more glycosylation sites. The addition may also be made by the incorporation of one or more species presenting an —OH group, preferably serine or threonine residues, within the sequence of the peptide (for O-linked glycosylation sites). The addition may be made by mutation or by full chemical synthesis of the peptide. The peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91: 10747-10751 (1994); Stemmer, *Nature* 370: 389-391 (1994); and U.S. Pat. Nos. 5,605,793, 5,837,458, 5,830,721 and 5,811,238.

Exemplary peptides with which the present invention can be practiced, methods of adding or removing glycosylation sites, and adding or removing glycosyl structures or substructures are described in detail in WO03/031464 and related U.S. and PCT applications.

The present invention also provides means of adding (or removing) one or more selected glycosyl residues to a peptide, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. Chemical deglycosylation is preferably brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N-linked glycosylation, and sites for O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC CRIT. REV. BIOCHEM., pp. 259-306 (1981).

In one embodiment, the invention provides a method for linking two or more peptides through a linking group. The linking group is of any useful structure and may be selected from straight- and branched-chain structures. Preferably, each terminus of the linker, which is attached to a peptide, includes a modified sugar (i.e., a nascent intact glycosyl linking group).

In an exemplary method of the invention, two peptides are linked together via a linker moiety that includes a polymeric (e.g., PEG linker). The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second peptides to the first and second glycosyl units, respectively. In practice, the (glycosyl)$^1$-PEG-(glycosyl)$^2$ linker is contacted with the first peptide and a first transferase for which the first glycosyl unit is a substrate, thereby forming (peptide)$^1$-(glycosyl)$^1$-PEG-(glycosyl)$^2$. Transferase and/or unreacted peptide is then optionally removed from the reaction mixture. The second peptide and a second transferase for which the second glycosyl unit is a substrate are added to the (peptide)$^1$-(glycosyl)$^1$-PEG-(glycosyl)$^2$ conjugate, forming (peptide)$^1$-(glycosyl)$^1$-PEG-(glycosyl)$^2$-(peptide)$^2$; at least one of the glycosyl residues is either directly or indirectly O-linked. Those of skill in the art will appreciate that the method outlined above is also applicable to forming conjugates between more than two peptides by, for example, the use of a branched PEG, dendrimer, poly(amino acid), polysaccharide or the like.

Preparation of Modified Sugars

In general, the sugar moiety or sugar moiety-linker cassette and the PEG or PEG-linker cassette groups are linked together through the use of reactive groups, which are typically transformed by the linking process into a new organic functional group or unreactive species. The sugar reactive functional group(s), is located at any position on the sugar moiety. Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a sugar nucleus or modifying group include, but are not limited to:
  (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
  (b) hydroxyl groups, which can be converted to, e.g., esters, ethers, aldehydes, etc.
  (c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;
  (d) dienophile groups, which are capable of participating in Diels-Alder reactions such as, for example, maleimido groups;
  (e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
  (f) sulfonyl halide groups for subsequent reaction with amines, for example, to form sulfonamides;
  (g) thiol groups, which can be, for example, converted to disulfides or reacted with acyl halides;
  (h) amine or sulfhydryl groups, which can be, for example, acylated, alkylated or oxidized;
  (i) alkenes, which can undergo, for example, cycloadditions, acylation, Michael addition, etc; and
  (j) epoxides, which can react with, for example, amines and hydroxyl compounds.

The reactive functional groups can be chosen such that they do not participate in, or interfere with, the reactions necessary to assemble the reactive sugar nucleus or modifying group.

Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., Curr. Med. Chem. 6: 93 (1999); and Schafer et al., J. Org. Chem. 65: 24 (2000)).

In an exemplary embodiment, the peptide that is modified by a method of the invention is a glycopeptide that is produced in mammalian cells (e.g., CHO cells) or in a transgenic animal and thus, contains N- and/or O-linked oligosaccharide chains, which are incompletely sialylated. The oligosaccharide chains of the glycopeptide lacking a sialic acid and containing a terminal galactose residue can be PEGylated, PPGylated or otherwise modified with a modified sialic acid.

In Scheme 1, the amino glycoside 1, is treated with the active ester of a protected amino acid (e.g., glycine) derivative, converting the sugar amine residue into the corresponding protected amino acid amide adduct. The adduct is treated with an aldolase to form α-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG attachment by reacting compound 3 with an activated PEG or PPG derivative (e.g., PEG-C(O)NHS, PEG-OC(O)O-p-nitrophenyl), producing species such as 4 or 5, respectively.

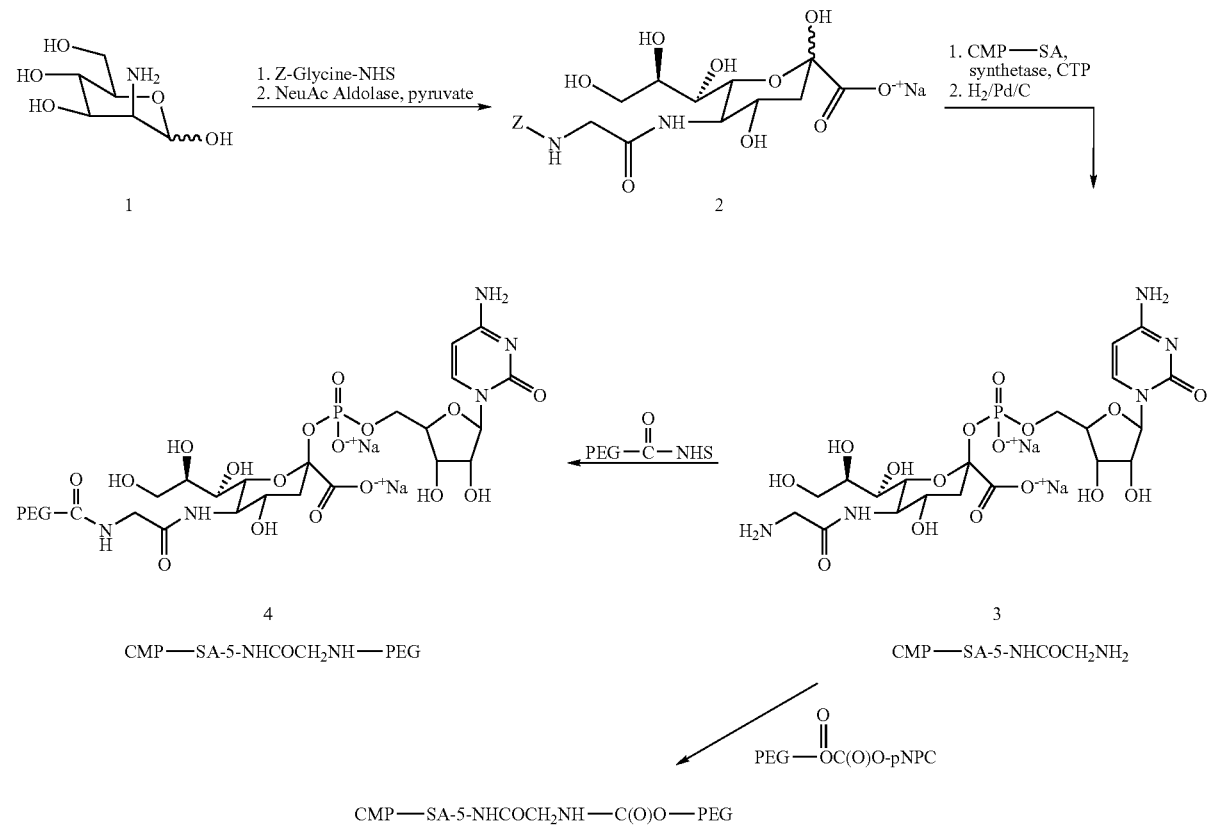

Scheme 1

Table 1 sets forth representative examples of sugar monophosphates that are derivatized with a PEG moiety. Certain of the compounds of Table 1 are prepared by the method of Scheme 1. Other derivatives are prepared by art-recognized methods. See, for example, Keppler et al., Glycobiology 11: 11R (2001); and Charter et al., Glycobiology 10: 1049 (2000)). Other amine reactive PEG and PPG analogues are commercially available, or they can be prepared by methods readily accessible to those of skill in the art.

TABLE 1
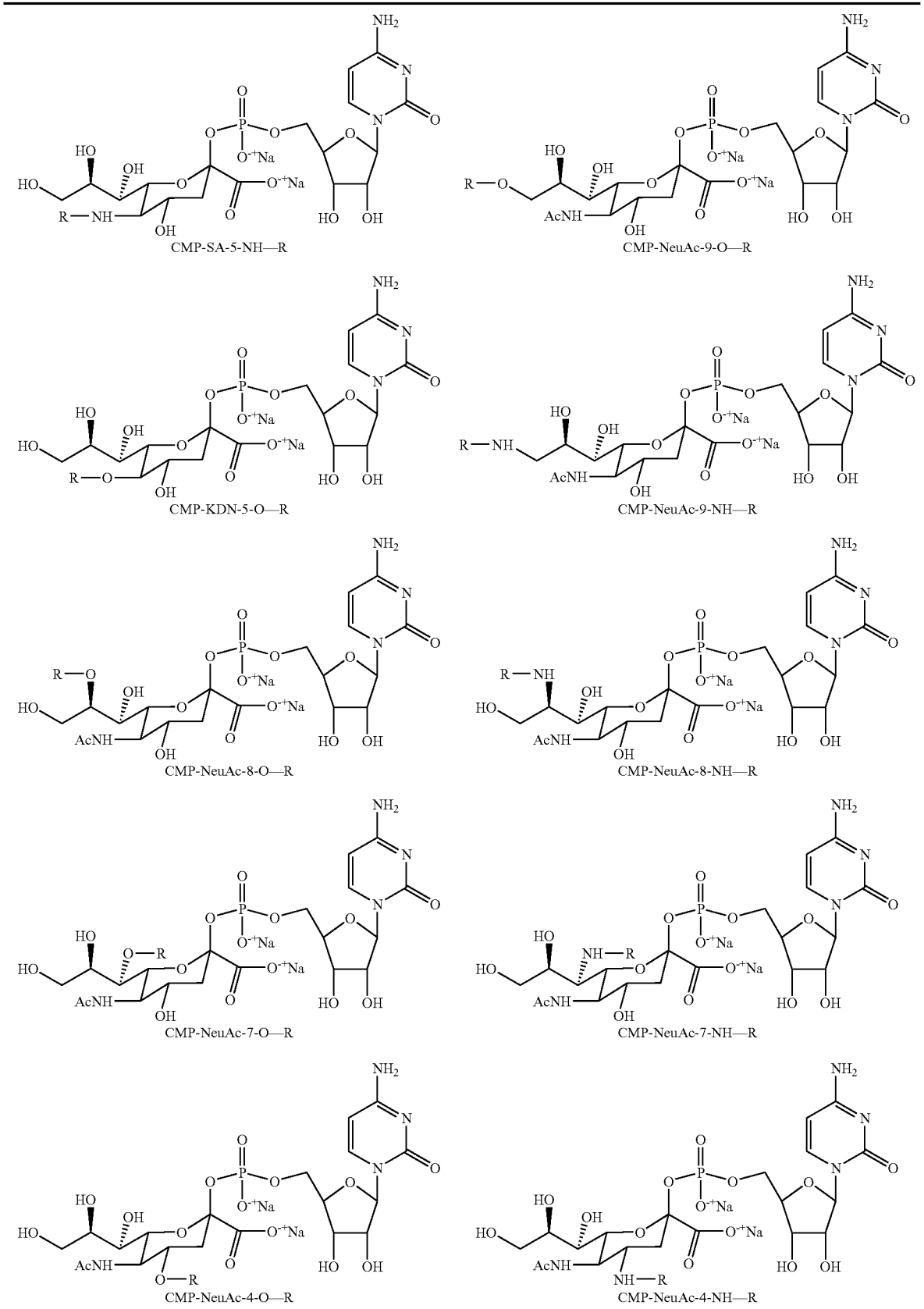

The modified sugar phosphates of use in practicing the present invention can be substituted in other positions as well as those set forth above. Presently preferred substitutions of sialic acid are set forth in Formula II:

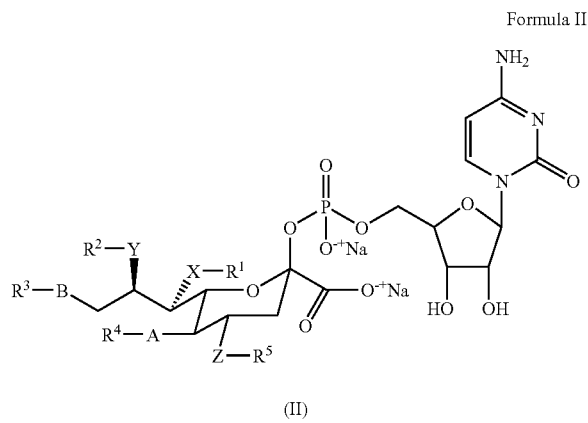

Formula II (II)

in which X is a linking group, which is preferably selected from —O—, —N(H)—, —S, CH$_2$—, and —N(R)$_2$, in which each R is a member independently selected from R$^1$-R$^5$. The symbols Y, Z, A and B each represent a group that is selected from the group set forth above for the identity of X. X, Y, Z, A and B are each independently selected and, therefore, they can be the same or different. The symbols R$^1$, R$^2$, R$^3$, R$^4$ and R$^5$ represent H, a PEG moiety, therapeutic moiety, biomolecule or other moiety. Alternatively, these symbols represent a linker that is bound to a PEG moiety, therapeutic moiety, biomolecule or other moiety.

Exemplary moieties attached to the conjugates disclosed herein include, but are not limited to, PEG derivatives (e.g., acyl-PEG, acyl-alkyl-PEG, alkyl-acyl-PEG carbamoyl-PEG, aryl-PEG), PPG derivatives (e.g., acyl-PPG, acyl-alkyl-PPG, alkyl-acyl-PPG carbamoyl-PPG, aryl-PPG), therapeutic moieties, diagnostic moieties, mannose-6-phosphate, heparin, heparan, SLe$_x$, mannose, mannose-6-phosphate, Sialyl Lewis X, FGF, VFGF, proteins, chondroitin, keratan, dermatan, albumin, integrins, antennary oligosaccharides, peptides and the like. Methods of conjugating the various modifying groups to a saccharide moiety are readily accessible to those of skill in the art (POLY (ETHYLENE GLYCOL CHEMISTRY: BIOTECHNICAL AND BIOMEDICAL APPLICATIONS, J. Milton Harris, Ed., Plenum Pub. Corp., 1992; POLY (ETHYLENE GLYCOL) CHEMICAL AND BIOLOGICAL APPLICATIONS, J. Milton Harris, Ed., ACS Symposium Series No. 680, American Chemical Society, 1997; Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991).

Linker Groups (Cross-Linking Groups)

Preparation of the modified sugar for use in the methods of the present invention includes attachment of a PEG moiety to a sugar residue and preferably, forming a stable adduct, which is a substrate for a glycosyltransferase. Thus, it is often preferred to use a linker, e.g., one formed by reaction of the PEG and sugar moiety with a cross-linking agent to conjugate the PEG and the sugar. Exemplary bifunctional compounds which can be used for attaching modifying groups to carbohydrate moieties include, but are not limited to, bifunctional poly(ethyleneglycols), polyamides, polyethers, polyesters and the like. General approaches for linking carbohydrates to other molecules are known in the literature. See, for example, Lee et al., *Biochemistry* 28: 1856 (1989); Bhatia et al., *Anal. Biochem.* 178: 408 (1989); Janda et al., *J. Am. Chem. Soc.* 112: 8886 (1990) and Bednarski et al., WO 92/18135. In the discussion that follows, the reactive groups are treated as benign on the sugar moiety of the nascent modified sugar. The focus of the discussion is for clarity of illustration. Those of skill in the art will appreciate that the discussion is relevant to reactive groups on the modifying group as well.

An exemplary strategy involves incorporation of a protected sulfhydryl onto the sugar using the heterobifunctional crosslinker SPDP (n-succinimidyl-3-(2-pyridyldithio)propionate and then deprotecting the sulfhydryl for formation of a disulfide bond with another sulfhydryl on the modifying group.

If SPDP detrimentally affects the ability of the modified sugar to act as a glycosyltransferase substrate, one of an array of other crosslinkers such as 2-iminothiolane or N-succinimidyl S-acetylthioacetate (SATA) is used to form a disulfide bond. 2-iminothiolane reacts with primary amines, instantly incorporating an unprotected sulfhydryl onto the amine-containing molecule. SATA also reacts with primary amines, but incorporates a protected sulfhydryl, which is later deacetaylated using hydroxylamine to produce a free sulfhydryl. In each case, the incorporated sulfhydryl is free to react with other sulfhydryls or protected sulfhydryl, like SPDP, forming the required disulfide bond.

The above-described strategy is exemplary, and not limiting, of linkers of use in the invention. Other crosslinkers are available that can be used in different strategies for crosslinking the modifying group to the peptide. For example, TPCH (S-(2-thiopyridyl)-L-cysteine hydrazide and TPMPH ((S-(2-thiopyridyl) mercapto-propionohydrazide) react with carbohydrate moieties that have been previously oxidized by mild periodate treatment, thus forming a hydrazone bond between the hydrazide portion of the crosslinker and the periodate generated aldehydes. TPCH and TPMPH introduce a 2-pyridylthione protected sulfhydryl group onto the sugar, which can be deprotected with DTT and then subsequently used for conjugation, such as forming disulfide bonds between components.

If disulfide bonding is found unsuitable for producing stable modified sugars, other crosslinkers may be used that incorporate more stable bonds between components. The heterobifunctional crosslinkers GMBS (N-gama-malimidobutyryloxy)succinimide) and SMCC (succinimidyl 4-(N-maleimido-methyl)cyclohexane) react with primary amines, thus introducing a maleimide group onto the component. The maleimide group can subsequently react with sulfhydryls on the other component, which can be introduced by previously mentioned crosslinkers, thus forming a stable thioether bond between the components. If steric hindrance between components interferes with either component's activity or the ability of the modified sugar to act as a glycosyltransferase substrate, crosslinkers can be used which introduce long spacer arms between components and include derivatives of some of the previously mentioned crosslinkers (i.e., SPDP). Thus, there is an abundance of suitable crosslinkers, which are useful; each of which is selected depending on the effects it has on optimal peptide conjugate and modified sugar production.

A variety of reagents are used to modify the components of the modified sugar with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981;

Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

i. Preferred Specific Sites in Crosslinking Reagents

1. Amino-Reactive Groups

In one preferred embodiment, the sites on the cross-linker are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of a modified sugar component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the modified sugar components. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained.

Isocyanates (and isothiocyanates) react with the primary amines of the modified sugar components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of modified sugar components, but also with sulfhydryl and imidazole groups.

p-Nitrophenyl esters of mono- and dicarboxylic acids are also useful amino-reactive groups. Although the reagent specificity is not very high, α- and ε-amino groups appear to react most rapidly.

Aldehydes such as glutaraldehyde react with primary amines of modified sugar. Although unstable Schiff bases are formed upon reaction of the amino groups with the aldehydes of the aldehydes, glutaraldehyde is capable of modifying the modified sugar with stable crosslinks. At pH 6-8, the pH of typical crosslinking conditions, the cyclic polymers undergo a dehydration to form α-β unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the modified sugar components, but reaction with the amino groups is the most important, resulting in a stable sulfonamide linkage.

2. Sulfhydryl-Reactive Groups

In another preferred embodiment, the sites are sulfhydryl-reactive groups. Useful, non-limiting examples of sulfhydryl-reactive groups include maleimides, alkyl halides, pyridyl disulfides, and thiophthalimides.

Maleimides react preferentially with the sulfhydryl group of the modified sugar components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form disulfides.

3. Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage teach how to modify a carboxyl group with carbodiimde (Yamada et al., *Biochemistry* 20: 4836-4842, 1981).

ii. Preferred Nonspecific Sites in Crosslinking Reagents

In addition to the use of site-specific reactive moieties, the present invention contemplates the use of non-specific reactive groups to link the sugar to the modifying group.

Exemplary non-specific cross-linkers include photoactivatable groups, completely inert in the dark, which are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

iii. Homobifunctional Reagents

1. Homobifunctional Crosslinkers Reactive with Primary Amines

Synthesis, properties, and applications of amine-reactive cross-linkers are commercially described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy) ethylsulfone (BSOCOES), bis-2-(sulfosuccinimidooxy-carbonyloxy)ethylsulfone (sulfo-BSOCOES), ethylene glycol-bis(succinimidylsuccinate) (EGS), ethylene glycolbis (sulfosuccinimidylsuccinate) (sulfo-EGS), dithiobis (succinimidyl-propionate) (DSP), and dithiobis (sulfosuccinimidylpropionate) (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3, 3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride.

Preferred, non-limiting examples of additional amino-reactive homobifunctional reagents include erythritolbiscarbonate which reacts with amines to give biscarbamates.

2. Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene) bismaleimide, N,N'-(1,2-phenylene)bismaleimide, azophenyldimaleimide, and bis(N-maleimidomethyl) ether.

Preferred, non-limiting examples of homobifunctional pyridyl disulfides include 1,4-di-3'-(2'-pyridyldithio)propionamidobutane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α,α'-dibromo-p-xylenesulfonic acid, N,N'-bis(b-bromoethyl)benzylamine, N,N'-di(bromoacetyl)phenylthydrazine, and 1,2-di (bromoacetyl)amino-3-phenylpropane.

3. Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-β-(4-azidosalicylamido)ethyldisulfide (BASED), di-N-(2-nitro-4-azidophenyl)-cystamine-S,S-dioxide (DNCO), and 4,4'-dithiobisphenylazide.

iv. HeteroBifunctional Reagents

1. Amino-Reactive HeteroBifunctional Reagents with a Pyridyl Disulfide Moiety

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio) propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio) toluene (SMPT), and sulfosuccinimidyl 6-α-methyl-α-(2-pyridyldithio)toluamidohexanoate (sulfo-LC-SMPT).

2. Amino-Reactive HeteroBifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

3. Amino-Reactive HeteroBifunctional Reagents with an Alkyl Halide Moiety

Synthesis, properties, and applications of such reagents are described in the literature Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino)hexanoylamino)hexanoate (SIAXX), succinimidyl-6-(((4-(iodoacetyl)-amino)-methyl)-cyclohexane-1-carbonyl)aminohexanoate (SIACX), and succinimidyl-4-((iodoacetyl)-amino)methylcyclohexane-1-carboxylate (SIAC).

A preferred example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety towards primary amine groups is controlled by the reaction temperature (McKenzie et al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

Other cross-linking agents are known to those of skill in the art. See, for example, Pomato et al., U.S. Pat. No. 5,965,106. It is within the abilities of one of skill in the art to choose an appropriate cross-linking agent for a particular application.

v. Cleavable Linker Groups

In yet a further embodiment, the linker group is provided with a group that can be cleaved to release the modifying group from the sugar residue. Many cleaveable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups is commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

Conjugation of Modified Sugars to Peptides

The PEG modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), U.S. Pat. Nos. 5,352,670, 5,374,541, 5,545,553, and commonly owned U.S. Pat. Nos. 6,399,336, and 6,440,703 which are incorporated herein by reference.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In an additional preferred embodiment, more than two enzymes are used to assemble the modified glycoprotein of the invention. The enzymes are used to alter a saccharide structure on the peptide at any point either before or after the addition of the modified sugar to the peptide.

In another embodiment, the method makes use of one or more exo- or endoglycosidase. The glycosidase is typically a mutant, which is engineered to form glycosyl bonds rather than rupture them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 30° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g, enzyme concentration, donor concentration, acceptor concentration, temperature, solvent volume), which are optimized for a selected system.

The present invention also provides for the industrial-scale production of modified peptides. As used herein, an industrial scale generally produces at least one gram of finsihed, purified conjugate.

In the discussion that follows, the invention is exemplified by the conjugation of modified sialic acid moieties to a glycosylated peptide. The exemplary modified sialic acid is labeled with PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other PEG moieties, therapeutic moieties, and biomolecules.

An enzymatic approach can be used for the selective introduction of PEGylated or PPGylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

An acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the peptide, e.g., a GlcNAc. The method includes incubating the peptide to be modified with a reaction mixture that contains a suitable amount of a galactosyltransferase (e.g., Galβ1,3 or Galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions.

In the discussion that follows, the method of the invention is exemplified by the use of modified sugars having a PEG moiety attached thereto. The focus of the discussion is for clarity of illustration. Those of skill will appreciate that the discussion is equally relevant to those embodiments in which the modified sugar bears a therapeutic moiety, biomolecule or the like.

In an exemplary embodiment of the invention in which a carbohydrate residue is "trimmed" prior to the addition of the modified sugar high mannose is trimmed back to the first generation biantennary structure. A modified sugar bearing a PEG moiety is conjugated to one or more of the sugar residues exposed by the "trimming back." In one example, a PEG moiety is added via a GlcNAc moiety conjugated to the PEG moiety. The modified GlcNAc is attached to one or both of the terminal mannose residues of the biantennary structure. Alternatively, an unmodified GlcNAc can be added to one or both of the termini of the branched species.

In another exemplary embodiment, a PEG moiety is added to one or both of the terminal mannose residues of the biantennary structure via a modified sugar having a galactose residue, which is conjugated to a GlcNAc residue added onto the terminal mannose residues. Alternatively, an unmodified Gal can be added to one or both terminal GlcNAc residues.

In yet a further example, a PEG moiety is added onto a Gal residue using a modified sialic acid.

In another exemplary embodiment, a high mannose structure is "trimmed back" to the mannose from which the biantennary structure branches. In one example, a PEG moiety is added via a GlcNAc modified with the polymer. Alternatively, an unmodified GlcNAc is added to the mannose, followed by a Gal with an attached PEG moiety. In yet another embodiment, unmodified GlcNAc and Gal residues are sequentially added to the mannose, followed by a sialic acid moiety modified with a PEG moiety.

In a further exemplary embodiment, high mannose is "trimmed back" to the GlcNAc to which the first mannose is attached. The GlcNAc is conjugated to a Gal residue bearing a PEG moiety. Alternatively, an unmodified Gal is added to the GlcNAc, followed by the addition of a sialic acid modified with a water-soluble sugar. In yet a further example, the terminal GlcNAc is conjugated with Gal and the GlcNAc is subsequently fucosylated with a modified fucose bearing a PEG moiety.

High mannose may also be trimmed back to the first GlcNAc attached to the Asn of the peptide. In one example, the GlcNAc of the GlcNAc-(Fuc)$_a$ residue is conjugated wit ha GlcNAc bearing a water soluble polymer. In another example, the GlcNAc of the GlcNAc-(Fuc)$_a$ residue is modified with Gal, which bears a water soluble polymer. In a still further embodiment, the GlcNAc is modified with Gal, followed by conjugation to the Gal of a sialic acid modified with a PEG moiety.

Other exemplary embodiments are set forth in commonly owned U.S. Patent application Publications: 20040132640; 20040063911; 20040137557; U.S. patent application Ser. Nos. 10/369,979; 10/410,913; 10/360,770; 10/410,945 and PCT/US02/32263 each of which is incorporated herein by reference.

The Examples set forth above provide an illustration of the power of the methods set forth herein. Using the methods described herein, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, an existing sialic acid is removed from a glycopeptide using a sialidase, thereby unmasking all or most of the underlying galactosyl residues. Alternatively, a peptide or glycopeptide is labeled with galactose residues, or an oligosaccharide residue that terminates in a galactose unit. Following the exposure of or addition of the galactose residues, an appropriate sialyltransferase is used to add a modified sialic acid. The approach is summarized in Scheme 2.

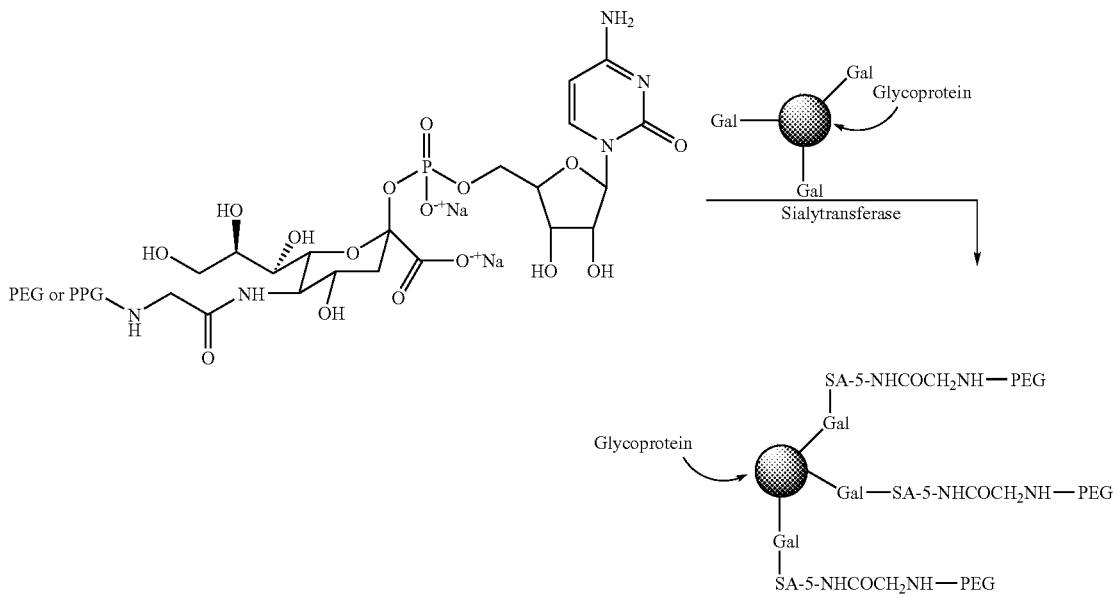

Scheme 2

In yet a further approach, summarized in Scheme 3, a masked reactive functionality is present on the sialic acid. The masked reactive group is preferably unaffected by the conditions used to attach the modified sialic acid to the erythropoietin. After the covalent attachment of the modified sialic acid to the peptide, the mask is removed and the peptide is conjugated with an agent such as PEG. The agent is conjugated to the peptide in a specific manner by its reaction with the unmasked reactive group on the modified sugar residue.

Scheme 3

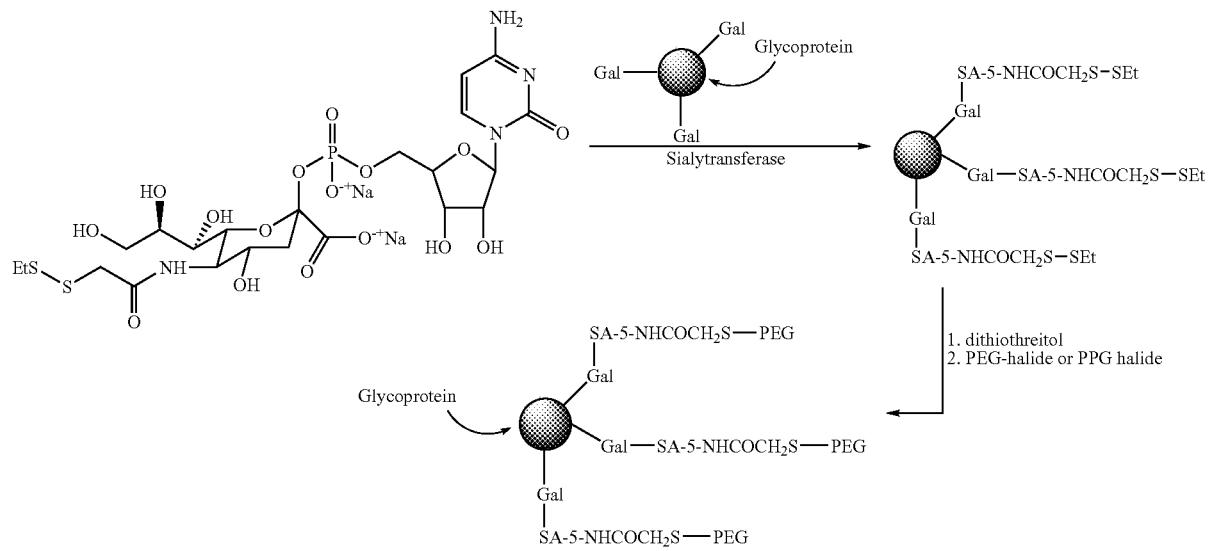

Any modified sugar can be used with its appropriate glycosyltransferase, depending on the terminal sugars of the oligosaccharide side chains of the glycopeptide (Table 2). As discussed above, the terminal sugar of the glycopeptide required for introduction of the PEGylated structure can be introduced naturally during expression or it can be produced post expression using the appropriate glycosidase(s), glycosyltransferase(s) or mix of glycosidase(s) and glycosyltransferase(s).

TABLE 2

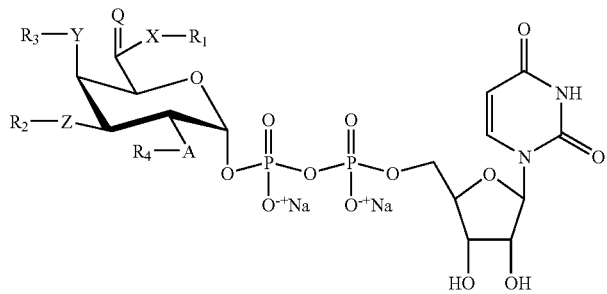

UDP-galactose-derivatives

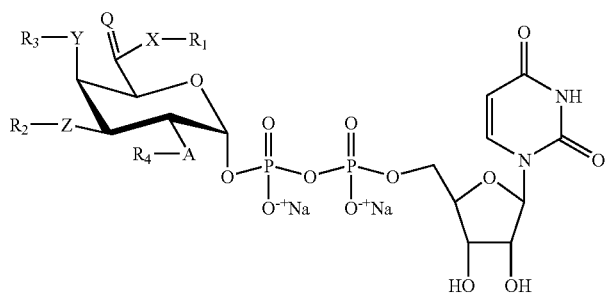

UDP-galactosamine-derivatives (when A = NH, $R_4$ may be acetyl)

TABLE 2-continued

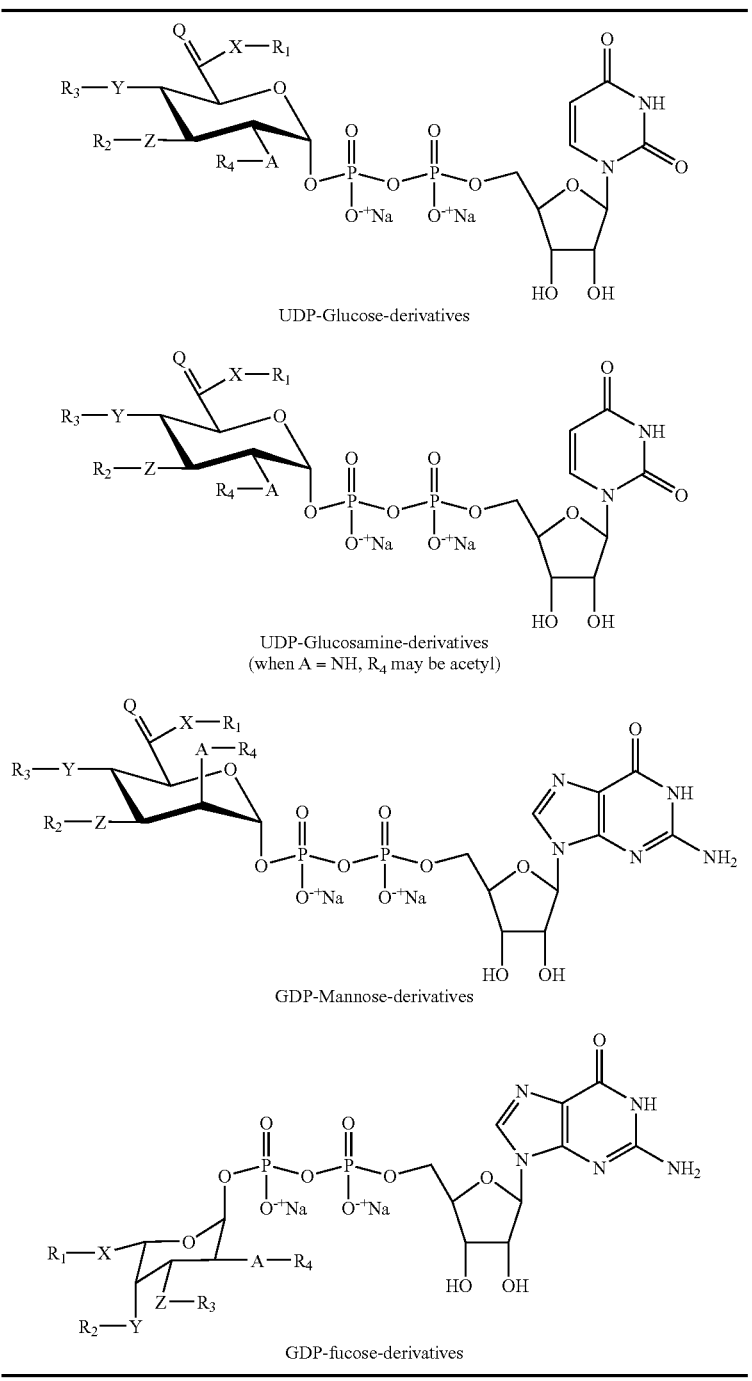

UDP-Glucose-derivatives

UDP-Glucosamine-derivatives
(when A = NH, R$_4$ may be acetyl)

GDP-Mannose-derivatives

GDP-fucose-derivatives

X = O, NH, S, CH$_2$, N—(R$_{1-5}$)$_2$.
Y = X; Z = X; A = X; B = X.
Q = H$_2$, O, S, NH, N—R.
R, R$_{1-4}$ = H, Linker-M, M.
M = PEG, e.g., m-PEG In a further exemplary embodiment, UDP-galactose-PEG is reacted with bovine milk β1,4-galactosyltransferase, thereby transferring the modified galactose to the appropriate terminal N-acetylglucosamine structure. The terminal GlcNAc residues on the glycopeptide may be produced during expression, as may occur in such expression systems as mammalian, insect, plant or fungus, but also can be produced by treating the glycopeptide with a sialidase and/or glycosidase and/or glycosyltransferase, as required.

In another exemplary embodiment, a GlcNAc transferase, such as GNT1-5, is utilized to transfer PEGylated-GlcN to a terminal mannose residue on a glycopeptide. In a still further exemplary embodiment, an the N- and/or O-linked glycan structures are enzymatically removed from a glycopeptide to expose an amino acid or a terminal glycosyl residue that is subsequently conjugated with the modified sugar. For example, an endoglycanase is used to remove the N-linked structures of a glycopeptide to expose a terminal GlcNAc as a GlcNAc-linked-Asn on the glycopeptide. UDP-Gal-PEG and the appropriate galactosyltransferase is used to introduce the PEG-galactose functionality onto the exposed GlcNAc.

In an alternative embodiment, the modified sugar is added directly to the peptide backbone using a glycosyltransferase known to transfer sugar residues to the peptide backbone. This exemplary embodiment is set forth in Scheme 4. Exemplary glycosyltransferases useful in practicing the present invention include, but are not limited to, GalNAc transferases (GalNAc T1-14), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the polypeptide chain.

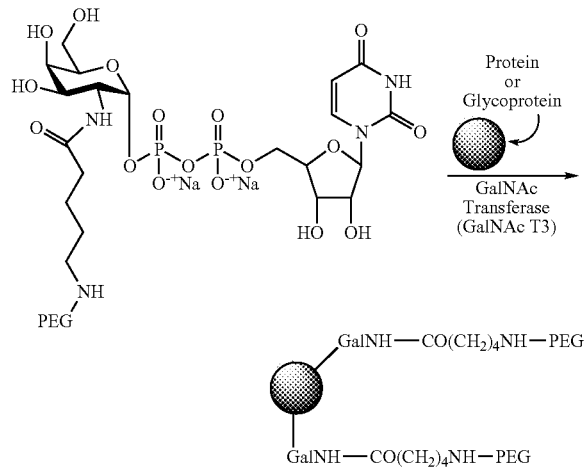

Scheme 4

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the peptide. Further elaboration of the modified sugar-peptide conjugate is within the scope of the invention.

i. Enzymes

Sugar Transfer

In addition to the enzymes discussed above in the context of forming the acyl-linked conjugate, the glycosylation pattern of the conjugate and the starting substrates (e.g., peptides, lipids) can be elaborated, trimmed back or otherwise modified by methods utilizing other enzymes. The methods of remodeling peptides and lipids using enzymes that transfer a sugar donor to an acceptor are discussed in great detail in DeFrees, WO 03/031464 A2, published Apr. 17, 2003. A brief summary of selected enzymes of use in the present method is set forth below.

Glycosyltransferases

Glycosyltransferases catalyze the addition of activated sugars (donor NDP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-NAG$_2$Glc$_3$Man$_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize the modified sugar as a sugar donor. Examples of such enzymes include Leloir pathway glycosyltransferase, such as galactosyltransferase, N-acetylglucosaminyltransferase, N-acetylgalactosaminyltransferase, fucosyltransferase, sialyltransferase, mannosyltransferase, xylosyltransferase, glucurononyltransferase and the like.

For enzymatic saccharide syntheses that involve glycosyltransferase reactions, glycosyltransferase can be cloned, or isolated from any source. Many cloned glycosyltransferases are known, as are their polynucleotide sequences. See, e.g., "The WWW Guide To Cloned Glycosyltransferases," (http://www.vei.co.uk/TGN/gt_guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, and oligosaccharyltransferases. Suitable glycosyltransferases include those obtained from eukaryotes, as well as from prokaryotes.

DNA encoding glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotide probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotide primers being produced from the glycosyltransferases gene sequence. See, U.S. Pat. No. 4,683,195 to Mullis et al. and U.S. Pat. No. 4,683,202 to Mullis.

The glycosyltransferase may be synthesized in host cells transformed with vectors containing DNA encoding the glycosyltransferases enzyme. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

In an exemplary embodiment, the invention utilizes a prokaryotic enzyme. Such glycosyltransferases include enzymes involved in synthesis of lipooligosaccharides (LOS), which are produced by many gram negative bacteria (Preston et al., *Critical Reviews in Microbiology* 23 (3): 139-180 (1996)). Such enzymes include, but are not limited to, the proteins of the rfa operons of species such as *E. coli* and *Salmonella typhimurium*, which include a β1,6 galactosyltransferase and a β1,3 galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an β1,2-glucosyltransferase (rfaJ)(Swiss-Prot Accession No. P27129 (*E. coli*) and Swiss-Prot Accession No. P 19817 (*S. typhimurium*)), and an β 1,2-N-acetylglucosaminyltransferase (rfaK) (EMBL Accession No. U00039 (*E. coli*). Other glycosyltransferases for which amino acid sequences are known include those that are encoded by operons such as rfaB, which have been characterized in organisms such as *Klebsiella pneumoniae, E. coli, Salmonella typhimurium, Salmonella enterica, Yersinia enterocolitica, Mycobacterium leprosum*, and the rh1 operon of *Pseudomonas aeruginosa*.

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens *Neisseria gonnorhoeae* and *N. meningitidis* (Scholten et al., *J. Med. Microbiol.* 41: 236-243 (1994)). The genes from *N. meningitidis* and *N. gonorrhoeae* that encode the glycosyltransferases involved in the biosynthesis of these structures have been identified from *N. meningitidis* immunotypes L3 and L1 (Jennings et al., *Mol. Microbiol.* 18: 729-740 (1995)) and the *N. gonorrhoeae* mutant F62 (Gotshlich, *J. Exp. Med.* 180: 2181-2190 (1994)). In *N. meningitidis*, a locus consisting of three genes, lgtA, lgtB and lg E, encodes the glycosyltransferase enzymes required for addition of the last three of the sugars in the lacto-N-neotetraose chain (Wakarchuk et al., *J. Biol. Chem.* 271: 19166-73 (1996)). Recently the enzymatic activity of the lgtB and lgtA gene product was demonstrated, providing the first direct evidence for their proposed glycosyltransferase function (Wakarchuk et al., *J. Biol. Chem.* 271 (45): 28271-276 (1996)). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an lgtC gene (Jennings et al., (1995), supra.). *Neisseria* glycosyltransferases and associated genes are also described in U.S. Pat. No. 5,545,553 (Gotschlich). Genes for α1,2-fucosyltransferase and α1,3-fucosyltransferase from *Helicobacter pylori* has also been characterized (Martin et al., *J. Biol. Chem.* 272: 21349-21356 (1997)). Also of use in the present invention are the glycosyltransferases of *Campylobacter jejuni* (see, for example, http://afmb.cnrs-mrs.fr/~pedro/CAZY/gtf_42.html).

Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4)GlcNAcβ-group in an oligosaccharide glycoside. Suitable fucosyltransferases for this reaction include the Galβ(1→3,4)GlcNAcβ1-α(1→3,4)fucosyltransferase (FTIII E.C. No. 2.4.1.65), which was first characterized from human milk (see, Palcic, et al., *Carbohydrate Res.* 190: 1-11 (1989); Prieels, et al., *J. Biol. Chem.* 256: 10456-10463 (1981); and Nunez, et al., *Can. J. Chem.* 59: 2086-2095 (1981)) and the Galβ(1→4)GlcNAcβ-αfucosyltransferases (FTIV, FTV, FTVI) which are found in human serum. FTVII (E.C. No. 2.4.1.65), a sialyl α(2→3)Galβ ((1→3)GlcNAcβ fucosyltransferase, has also been characterized. A recombinant form of the Galβ(1→3,4) GlcNAcβ-α (1→3,4)fucosyltransferase has also been characterized (see, Dumas, et al., *Bioorg. Med. Letters* 1: 425-428 (1991) and Kukowska-Latallo, et al., *Genes and Development* 4: 1288-1303 (1990)). Other exemplary fucosyltransferases include, for example, α1,2 fucosyltransferase (E.C. No. 2.4.1.69). Enzymatic fucosylation can be carried out by the methods described in Mollicone, et al., *Eur. J. Biochem.* 191: 169-176 (1990) or U.S. Pat. No. 5,374,655. Cells that are used to produce a fucosyltransferase will also include an enzymatic system for synthesizing GDP-fucose.

Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBank j04989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et al., *Immunogenetics* 41: 101-105 (1995)). Another suitable α1,3 galactosyltransferase is that which is involved in synthesis of the blood group B antigen (EC 2.4.1.37, Yamamoto et al., *J. Biol. Chem.* 265: 1146-1151 (1990) (human)). Yet a further exemplary galactosyltransferase is core Gal-T1.

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. J. Biochem.* 183: 211-217 (1989)), human (Masri et al., *Biochem. Biophys. Res. Commun.* 157: 657-663 (1988)), murine (Nakazawa et al., J. Biochem. 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe*, Chapell et al., *Mol. Biol. Cell* 5: 519-528 (1994)).

Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol. Chem.* 257: 13845 (1982) and Wen et al., *J. Biol. Chem.* 267: 21011 (1992). Another exemplary α2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-β-1,4-GlcNAc α-2,6 sialyltransferase (See, Kurosawa et al. *Eur. J. Biochem.* 219: 375-381 (1994)).

Preferably, for glycosylation of carbohydrates of glycopeptides the sialyltransferase will be able to transfer sialic acid to the sequence Galβ1,4GlcNAc-, the most common penultimate sequence underlying the terminal sialic acid on fully sialylated carbohydrate structures (see, Table 2).

TABLE 2

Sialyltransferases which use the Galβ1,4GlcNAc sequence as an acceptor substrate

| Sialyltransferase | Source | Sequence(s) formed | Ref. |
|---|---|---|---|
| ST6Gal I | Mammalian | NeuAc☐2,6Galβ1,4GlCNAc- | 1 |
| ST3Gal III | Mammalian | NeuAc☐2,3Galβ1,4GlCNAc- | 1 |
| | | NeuAc☐2,3Galβ1,3GlCNAc- | |
| ST3Gal IV | Mammalian | NeuAc☐2,3Galβ1,4GlCNAc- | 1 |
| | | NeuAc☐2,3Galβ1,3GlCNAc- | |
| ST6Gal II | Mammalian | NeuAc☐2,6Galβ1,4GlCNA | |
| ST6Gal II | photobacterium | NeuAc☐2,6Galβ1,4GlCNAc- | 2 |
| ST3Gal V | N. meningitides N. gonorrhoeae | NeuAc☐2,3Galβ1,4GlCNAc- | 3 |

1) Goochee et al., Bio/Technology 9: 1347-1355 (1991)
2) Yamamoto et al., J. Biochem. 120: 104-110 (1996)
3) Gilbert et al., J. Biol. Chem. 271: 28271-28276 (1996)

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc or Galβ1,4GlcNAc glycoside (see, e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3Gal III.

Other exemplary sialyltransferases of use in the present invention include those isolated from *Campylobacter jejuni*, including the α(2,3). See, e.g, WO99/49051.

Sialyltransferases other those listed in Table 2, are also useful in an economic and efficient large-scale process for sialylation of commercially important glycopeptides. As a simple test to find out the utility of these other enzymes, various amounts of each enzyme (1-100 mU/mg protein) are reacted with asialo-α$_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides or glycopeptides, or N-linked oligosaccharides enzymatically released from the peptide backbone can be used in place of asialo-α$_1$ AGP for this evaluation. Sialyltransferases with the ability to sialylate N-linked oligosaccharides of glycopeptides more efficiently than ST6Gal I are useful in a practical large-scale process for peptide sialylation.

GalNAc Transferases

N-acetylgalactosaminyltransferases are of use in practicing the present invention, particularly for binding a GalNAc moiety to an amino acid of the O-linked glycosylation site of the peptide. Suitable N-acetylgalactosaminyltransferases include, but are not limited to, α(1,3) N-acetylgalactosaminyltransferase, β(1,4) N-acetylgalactosaminyltransferases (Nagata et al., *J. Biol. Chem.* 267: 12082-12089 (1992) and Smith et al., *J. Biol. Chem.* 269: 15162 (1994)) and polypeptide N-acetylgalactosaminyltransferase (Homa et al., *J. Biol. Chem.* 268: 12609 (1993)).

Production of proteins such as the enzyme GalNAc T$_{I-XX}$ from cloned genes by genetic engineering is well known. See, eg., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

Cell-Bound Glycosyltransferases

In another embodiment, the enzymes utilized in the method of the invention are cell-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for solubilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, MOLECULAR APPROACHES to SUPRACELLULAR PHENOMENA, 1990).

Methods have been developed to alter the glycosyltransferases expressed by cells. For example, Larsen et al., *Proc. Natl. Acad. Sci. USA* 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose:.β.-D-galactosyl-1,4-N-acetyl-D-glucosaminide α-1,3-galactosyltransferase was transfected into COS-1 cells. The transfected cells were then cultured and assayed for α 1-3 galactosyltransferase activity.

Francisco et al., *Proc. Natl. Acad. Sci. USA* 89: 2713-2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning.

Sulfotransferases

The invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., *J. Biol. Chem.* 270: 18575-18580 (1995); GenBank Accession No. D49915), glycosaminoglycan N-acetylglucosamine N-deacetylase/N-sulphotransferase 1 (Dixon et al., *Genomics* 26: 239-241 (1995); UL18918), and glycosaminoglycan N-acetylglucosamine N-deacetylase/N-sulphotransferase 2 (murine cDNA described in Orellana et al., *J. Biol. Chem.* 269: 2270-2276 (1994) and Eriksson et al., *J. Biol. Chem.* 269: 10438-10443 (1994); human cDNA described in GenBank Accession No. U2304).

Glycosidases

This invention also encompasses the use of wild-type and mutant glycosidases. Mutant β-galactosidase enzymes have been demonstrated to catalyze the formation of disaccharides through the coupling of an α-glycosyl fluoride to a galactosyl acceptor molecule. (Withers, U.S. Pat. No. 6,284,494; issued Sep. 4, 2001). Other glycosidases of use in this invention include, for example, β-glucosidases, β-galactosidases, β-mannosidases, β-acetyl glucosaminidases, β-N-acetyl galactosaminidases, β-xylosidases, β-fucosidases, cellulases, xylanases, galactanases, mannanases, hemicellulases, amylases, glucoamylases, α-glucosidases, α-galactosidases, α-mannosidases, α-N-acetyl glucosaminidases, α-N-acetyl galactose-aminidases, α-xylosidases, α-fucosidases, and neuraminidases/sialidases.

Immobilized Enzymes

The present invention also provides for the use of enzymes that are immobilized on a solid and/or soluble support. In an exemplary embodiment, there is provided a glycosyltransferase that is conjugated to a PEG via an intact glycosyl linker according to the methods of the invention. The PEG-linker-enzyme conjugate is optionally attached to solid support. The use of solid supported enzymes in the methods of the invention simplifies the work up of the reaction mixture and purification of the reaction product, and also enables the facile recovery of the enzyme. The glycosyltransferase conjugate is utilized in the methods of the invention. Other combinations of enzymes and supports will be apparent to those of skill in the art.

Fusion Proteins

In other exemplary embodiments, the methods of the invention utilize fusion proteins that have more than one enzymatic activity that is involved in synthesis of a desired glycopeptide conjugate. The fusion polypeptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar that is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. In other embodiments the fusion protein includes the catalytically active domains of two or more glycosyltransferases. See, for example, 5,641,668. The modified glycopeptides of the present invention can be readily designed and manufactured utilizing various suitable fusion proteins (see, for example, PCT Patent Application PCT/CA98/01180, which was published as WO 99/31224 on Jun. 24, 1999.)

Purification of Erythropoietin Conjugates

The products produced by the above processes can be used without purification. However, it is usually preferred to recover the product. Standard, well-known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins such as glycosyl transferases. Nanofiltration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used. Thus, in a typical application, saccharides prepared by the methods of the present invention will be retained in the membrane and contaminating salts will pass through.

If the modified glycoprotein is produced intracellularly, as a first step, the particulate debris, either host cells or lysed fragments, is removed, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, enzymes, etc., followed by one or more concentration, salting-out, aqueous ion-exchange, or size-exclusion chromatography steps. Additionally, the modified glycoprotein may be purified by affinity chromatography. Finally, HPLC may be employed for final purification steps.

A protease inhibitor, e.g., methylsulfonylfluoride (PMSF) may be included in any of the foregoing steps to inhibit proteolysis and antibiotics may be included to prevent the growth of adventitious contaminants.

Within another embodiment, supernatants from systems which sproduce the modified glycopeptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a polypeptide variant composition. Some or all of the foregoing purification steps, in various combinations, can also be employed to provide a homogeneous modified glycoprotein.

The modified glycopeptide of the invention resulting from a large-scale fermentation may be purified by methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography may be utilized to purify the modified glycoprotein.

Pharmaceutical Compositions

In another aspect, the invention provides a pharmaceutical composition. The pharmaceutical composition includes a pharmaceutically acceptable diluent and a covalent conjugate between a non-naturally-occurring, PEG moiety, therapeutic moiety or biomolecule and a glycosylated or non-glycosylated peptide. The polymer, therapeutic moiety or biomolecule is conjugated to the peptide via an intact glycosyl linking group interposed between and covalently linked to both the peptide and the polymer, therapeutic moiety or biomolecule.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}$I, $^{14}$C, or tritium.

The active ingredient used in the pharmaceutical compositions of the present invention is glycopegylated erythropoietin and its derivatives having the biological properties of causing bone marrow cells to increase production of reticulocytes and red blood cells. The liposomal dispersion of the present invention is useful as a parenteral formulation in treating blood disorders characterized by low or defective red blood cell production such as various forms of anemia, including anemias associated with chronic renal failure, zidovidine treated HIV infected patients, and cancer patients on chemotherapy. It may also have application in the treatment of a variety of disease states, disorders and states of hematologic irregularity such as sickle cell disease, beta-thalassemia, cystic fibrosis, pregnancy and menstrual disorders, early anemia of prematurity, spinal cord injury, space flight, acute blood loss, aging and the like. Preferably, the EPO composition of the present invention is administered parenterally (e.g. IV, IM, SC or IP). Effective dosages are expected to vary considerably depending on the condition being treated and the route of administration but are expected to be in the range of about 0.1 (~7 U) to 100 (~7000 U) µg/kg body weight of the active material. Preferable doses for treatment of anemic conditions are about 50 to about 300 Units/kg three times a week. Because the present invention provides an erythropoietin with an enhanced in vivo residence time, the stated dosages are optionally lowered when a composition of the invention is administered.

The following examples are provided to illustrate the conjugates, and methods and of the present invention, but not to limit the claimed invention.

EXAMPLES

Example 1

Preparation of UDP-GalNAc-6'-CHO

UDP-GalNAc (200 mg, 0.30 mmoles) was dissolved in a 1 mM CuSO$_4$ solution (20 mL) and a 25 mM NaH$_2$PO$_4$ solution (pH 6.0; 20 mL). Galactose oxidase (240 U; 240 µL) and catalase (13000 U; 130 µL) were then added, the reaction system equipped with a balloon filled with oxygen and stirred at room temperature for seven days. The reaction mixture was then filtered (spin cartridge; MWCO 5K) and the filtrate (~40 mL) was stored at 4° C. until required. TLC (silica; EtOH/water (7/2); R$_f$=0.77; visualized with anisaldehyde stain).

Example 2

Preparation of UDP-GalNAc-6'-NH$_2$

Ammonium acetate (15 mg, 0.194 mmoles) and NaBH$_3$CN (1M THF solution; 0.17 mL, 0.17 mmoles) were added to the UDP-GalNAc-6'-CHO solution from above (2 mL or ~20 mg) at 0° C. and allowed to warm to room temperature overnight. The reaction was filtered through a G-10 column with water and the product collected. The appropriate fractions were freeze-dried and stored frozen. TLC (silica; ethanol/water (7/2); R$_f$=0.72; visualized with ninhydrin reagent).

Example 3

Preparation of UDP-GalNAc-6-NHCO(CH$_2$)$_2$—O—PEG-OMe (1 KDa)

The galactosaminyl-1-phosphate-2-NHCO(CH$_2$)$_2$—O—PEG-OMe (1 KDa) (58 mg, 0.045 mmoles) was dissolved in DMF (6 mL) and pyridine (1.2 mL). UMP-morpholidate (60 mg, 0.15 mmoles) was then added and the resulting mixture stirred at 70° C. for 48 h. The solvent was removed by bubbling nitrogen through the reaction mixture and the residue purified by reversed phase chromatography (C-18 silica, step gradient between 10 to 80%, methanol/water). The desired fractions were collected and dried at reduced pressure to yield 50 mg (70%) of a white solid. TLC (silica, propanol/H$_2$O/NH$_4$OH, (30/20/2), R$_f$=0.54). MS (MALDI): Observed, 1485, 1529, 1618, 1706.

Example 4

Preparation of Cysteine-PEG$_2$ (2)

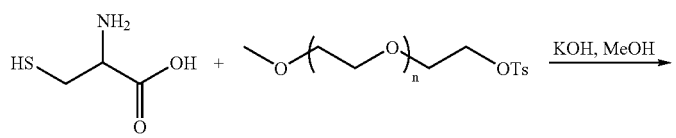

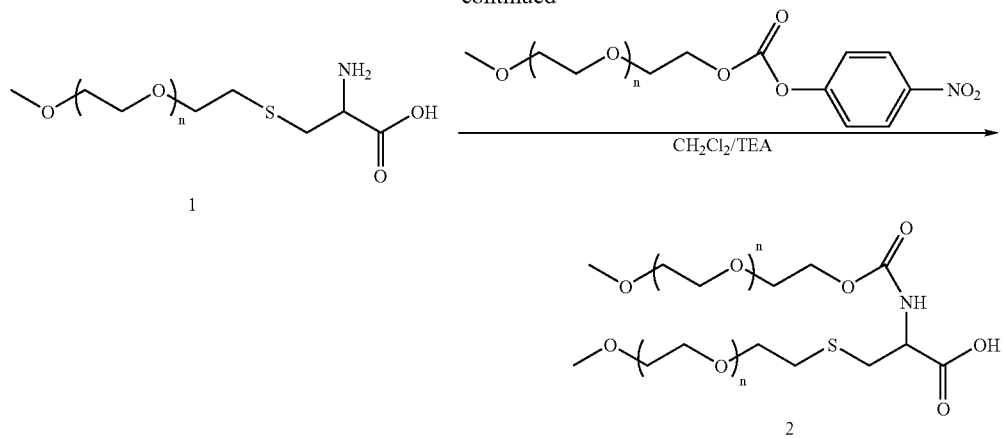

4.1 Synthesis of Compund 1

Potassium hydroxide (84.2 mg, 1.5 mmol, as a powder) was added to a solution of L-cysteine (93.7 mg, 0.75 mmol) in anhydrous methanol (20 L) under argon. The mixture was stirred at room temperature for 30 min, and then mPEG-O-tosylate of molecular mass 20 kilodalton (Ts; 1.0 g, 0.05 mmol) was added in several portions over 2 hours. The mixture was stirred at room temperature for 5 days, and concentrated by rotary evaporation. The residue was diluted with water (30 mL), and stirred at room temperature for 2 hours to destroy any excess 20 kilodalton mPEG-O-tosylate. The solution was then neutralized with acetic acid, the pH adjusted to pH 5.0 and loaded onto a reversed phase chromatography (C-18 silica) column. The column was eluted with a gradient of methanol/water (the product elutes at about 70% methanol), product elution monitored by evaporative light scattering, and the appropriate fractions collected and diluted with water (500 mL). This solution was chromatographed (ion exchange, XK 50 Q, BIG Beads, 300 ml, hydroxide form; gradient of water to water/acetic acid-0.75N) and the pH of the appropriate fractions lowered to 6.0 with acetic acid. This solution was then captured on a reversed phase column (C-18 silica) and eluted with a gradient of methanol/water as described above. The product fractions were pooled, concentrated, redissolved in water and freeze-dried to afford 453 mg (44%) of a white solid (1). Structural data for the compound were as follows: $^1$H-NMR (500 MHz; $D_2O$) δ 2.83 (t, 2H, O—C—C$\underline{H}_2$—S), 3.05 (q, 1H, S—C$\underline{H}H$—CHN), 3.18 (q, 1H, (q, 1H, S—C$\underline{H}H$—CHN), 3.38 (s, 3H, C$\underline{H}_3$O), 3.7 (t, OC$\underline{H}_2$C$\underline{H}_2$O), 3.95 (q, 1H, C$\underline{H}$N). The purity of the product was confirmed by SDS PAGE.

4.2 Synthesis of Compound 2 (Cysteine-PEG₂)

Triethylamine (~0.5 mL) was added dropwise to a solution of compound 1 (440 mg, 22 μmol) dissolved in anhydrous $CH_2Cl_2$ (30 mL) until the solution was basic. A solution of 20 kilodalton mPEG-O-p-nitrophenyl carbonate (660 mg, 33 μmol) and N-hydroxysuccinimide (3.6 mg, 30.8 μmol) in $CH_2Cl_2$ (20 mL) was added in several portions over 1 hour at room temperature. The reaction mixture was stirred at room temperature for 24 hours. The solvent was then removed by rotary evaporation, the residue was dissolved in water (100 mL), and the pH adjusted to 9.5 with 1.0 N NaOH. The basic solution was stirred at room temperature for 2 hours and was then neutralized with acetic acid to a pH 7.0. The solution was then loaded onto a reversed phase chromatography (C-18 silica) column. The column was eluted with a gradient of methanol/water (the product elutes at about 70% methanol), product elution monitored by evaporative light scattering, and the appropriate fractions collected and diluted with water (500 mL). This solution was chromatographed (ion exchange, XK 50 Q, BIG Beads, 300 mL, hydroxide form; gradient of water to water/acetic acid-0.75N) and the pH of the appropriate fractions lowered to 6.0 with acetic acid. This solution was then captured on a reversed phase column (C-18 silica) and eluted with a gradient of methanol/water as described above. The product fractions were pooled, concentrated, redissolved in water and freeze-dried to afford 575 mg (70%) of a white solid (2). Structural data for the compound were as follows: $^1$H-NMR (500 MHz; $D_2O$) δ 2.83 (t, 2H, O—C—C$\underline{H}_2$—S), 2.95 (t, 2H, O—C—C$\underline{H}_2$—S), 3.12 (q, 1H, S—C $\underline{HH}$—CHN), 3.39 (s, 3H C$\underline{H}_3$O), 3.71 (t, OC$\underline{H}_2$C$\underline{H}_2$O). The purity of the product was confirmed by SDS PAGE.

Example 5

Preparation of UDP-GalNAc-6-NHCO(CH₂)₂—O—PEG-OMe (1 KDa)

Galactosaminyl-1-phosphate-2-NHCO(CH₂)₂—O-PEG-OMe (1 kilodalton) (58 mg, 0.045 mmoles) was dissolved in DMF (6 mL) and pyridine (1.2 mL). UMP-morpholidate (60 mg, 0.15 mmoles) was then added and the resulting mixture stirred at 70° C. for 48 h. The solvent was removed by bubbling nitrogen through the reaction mixture and the residue purified by reversed phase chromatography (C-18 silica, step gradient between 10 to 80%, methanol/water). The desired fractions were collected and dried at reduced pressure to yield 50 mg (70%) of a white solid. TLC (silica, propanol/$H_2O$/$NH_4OH$, (30/20/2), $R_f$=0.54). MS (MALDI): Observed, 1485, 1529, 1618, 1706.

Example 6

GnT1 and GalT1 Reaction in One Pot

6.1 Reaction in One Pot

The one pot GlcNAc transferase-1 and galactose transferase-1 reaction was carried out by incubating EPO (1 mg/mL) in 100 mM Tris HCl pH 7.5 or MES pH 6.5 containing 150 mM NaCl, 5 mM UDP-GlcNAc, 5 mM UDP-Gal, 5 mM $MnCl_2$, 0.02% sodium azide, 30 mU/mL of purified GlcNAc transferase-1 and 200 mU/mL of purified galactose transferase-1 at 32° C. for 16 h.

6.2 Purification of EPO on Superdex75

A Superdex 75 column was equilibrated in 100 mM MES buffer pH 6.5 containing 150 mM NaCl at a flow rate of 5 mL/min. The EPO, product from step 6.1 (above) was loaded on to the column and eluted with the equilibration buffer. The eluate was monitored for absorbance at 280 nm and conductivity. SDS-PAGE was used to determine which pooled peak fractions contains the EPO and used in further experiments.

6.3 ST3Gal-III Reaction

The ST3GalIII reaction was carried out by incubating 1 mg/mL EPO-Gal (from step 6.2, above) in 100 mM Tris HCl pH 7.5 or MES pH 6.5 containing 150 mM NaCl, 0.5 mM CMP-N-acetyl-neuraminic acid-20 kilodalton-PEG, 0.02% sodium azide, and 200 mU/mL of purified ST3Gal-III at 32° C. for 16 hours.

Example 7

GnT1, GalT1 and ST3Gal-III (Using CMP-NAN-20 KPEG) Reaction in One Pot

EPO (1 mg/mL) was incubated with 30 mU/mL of GlcNAc transferase-1, 200 mU/mL of Galactose transferase-1 and 500 mU/mL of ST3GalIII with sugar nucleotides and CMP-N-acetyl-neuraminic acid-20 Kd PEG in 100 mM MES buffer pH 6.5 and analyzed using SDS-PAGE. Similar to the results obtained in the two-step enzyme remodeling reactions, three bands of PEGylated EPO are seen in the one-pot, three enzyme preparations.

Example 8

Production of Biantennary PEG-EPO 8.1 Addition of GlcNAc to rEPO

Recombinant EPO, expressed in baculovirus (1 mg/mL) in 0.1 M Tris, 0.15 M NaCl, 5 mM $MnCl_2$ and 0.02% sodium azide at pH 7.2 was incubated with 3 mM USP-GlcNAc, 50 mU/mg GlcNAc transferase-1 and 50 mU/mg GlcNAc transferase-II at 32° C. for 24 hours.

8.2 Addition of Galactose

To the GlcNAc-labeled peptide of step 8.1 (above) was added 3 mM UDP-Gal and 0.2 U/mg Galactose transferase-1. The mixture was incubated for 36 hours at 32° C. The galactosylated product was isolated by gel filtration chromatography on a Superdex 75 column in Tris-buffered saline. The purified product was concentrated to 1 mg/mL.

8.3 Addition of Sialic Acid or Sialic Acid PEG

The galactosylated product from step 8.2 (above) (1 mg/mL) in 0.1 M Tris, 0.1M NaCl at pH 7.2 was incubated at 32° C. for 24 hours with 200 mU/mg ST3GalIII and 0.5 mM CMP-sialic acid or CMP-sialic acid-PEG (where the PEG has a molecular mass of 5 kilodaltons, 10 kilodaltons or 20 kilodaltons).

Example 9

N-linked 30K PEGylation by CST-II

Figure 3A:
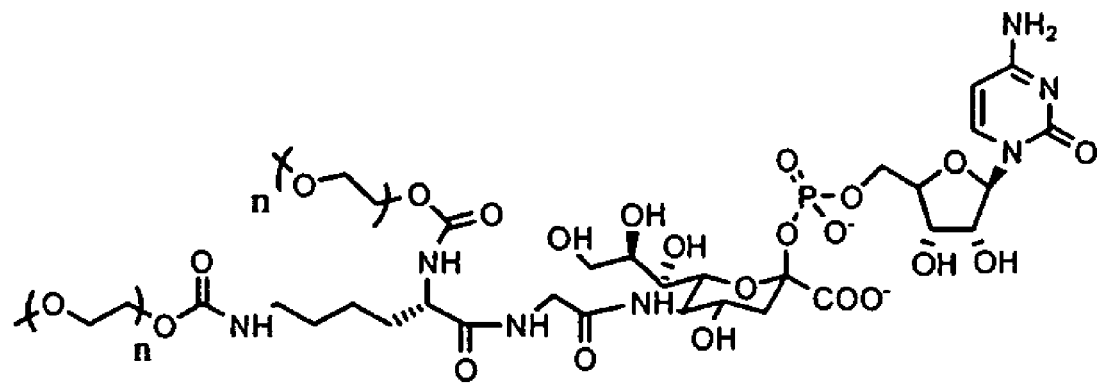
FIG. 3.
Figure 3B:
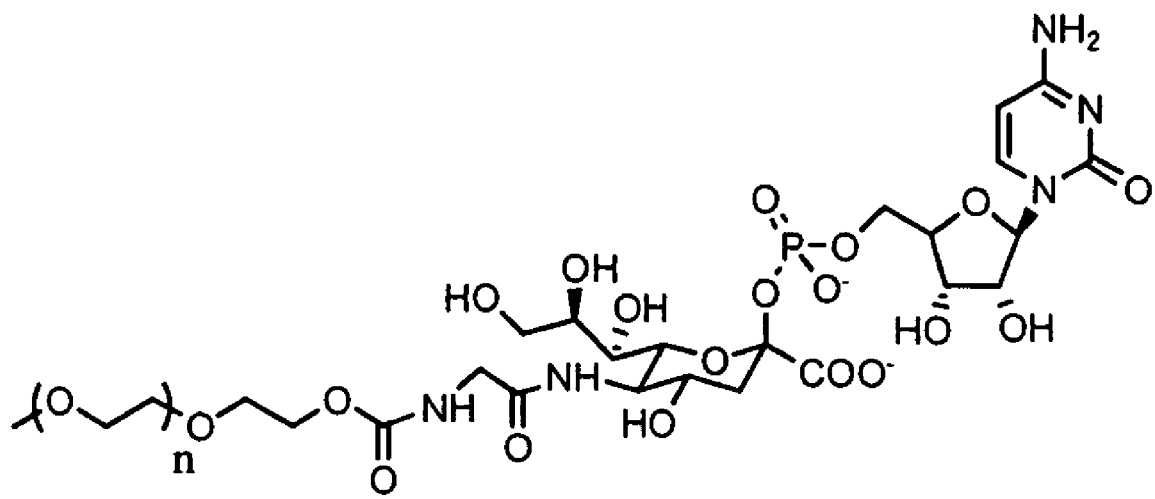

EPO glycosylated as expressed in CHO (Chinese Hamster Ovary) cells (5 mg, 0.166 μmol, 5 ml) was concentrated and buffer exchanged with tris buffer (50 mM Tris, 0.15M NaCl, 0.001 M $CaCl_2$+0.005% $NaN_3$) to a final volume of 5 ml. Then CMP-sialic acid-PEG (30 kilodaltons, 25 mg, 0.833 μmol; see FIG. 3B for structure of 30 Kdalton CMP-sialic acid-PEG), 0.25 mL 100 mM $MnCl_2$ 0.25 ml, and a bifunctional sialyltransferase from *Campylobacter jejuni*, CST-II (1.4 U/mL, 0.5 ml, 0.7 U), were added. The resulting mixture was rocked at 32° C. for 48 hours.

At the conclusion of the reaction, the mixture was concentrated by ultrifitration to 1 mL final volume, and was then buffer exchanged with 25 mM NaOAc+0.005% Tween-80 (pH 6.0) to 2.5 ml. Q-Sepharose IEX chromatography was performed using 25 mM NaOAc+2M NaCl+0.005% Tween-80 (pH 6.0) as eluent. Peak 2 was collected and concentrated to 1.5 ml by ultrifiltration, then subjected to superdex-200 purification (column: Superdex 200, 16/60 GL, Amersham) using 1×PBS (pH 5.5+0.005% Tween80) as eluent. Peak 2 was collected and concentrated to 1.5 ml. This resulting material was sterile filtered and formulated to a final volume of 2.5 mL using 10 mM NaOAc (0.75% NaCl, pH 5.5). Protein concentration 264 μg/ml; 660 μg protein was obtained (BCA determination).

Example 10

The following example illustrates a method for preparing O-linked 40 kilodalton PEG linked EPO using ST3GalIII 10.1 Desialylation In this step EPO grown in Chinese Hamster Ovary cells (CHO cells), was desialylated. The GlcNAc-Gal linkage serves as an acceptor for transfer of the modified sialic acid PEG in step 10.2, below.

EPO solution 10 ml (10 mg, 0.33 μmol) glycosylated as expressed in CHO (Chinese Hamster Ovary) cells, was buffer exchanged with Tris buffer (20 mM Tris, 50 mM NaCl, 5 mM $CaCl_2$, 0.02% $NaN_3$, pH 7.2) to give a final volume of 10 ml. Then 750 mU 2,3,6,8-neuramidase, from *Arthrobacter Ureafaciens*, was added to the solution. The resulting mixture was rocked at 32° C. for 48 hours. The product of this step was used directly in the next step of the protocol (see below).

10.2 O-linked 40K PEGylation

In this step O-sialyltranferase is used to transfer a modified sialic acid-PEG moiety to the desialylated EPO from step 10.1, above.

CMP-sialic acid-PEG (40 kilodalton, 33 mg, 0.825 μmol; see FIG. 3A for the structure of 40 kilodalton CMP-SA-PEG), O-sialyltransferase (1.4 U/ml, 300 mU), and 0.25 mL of 100 mM $MnCl_2$ were added to half of the above mixture. This mixture was rocked at 32° C. for 48 hours. After the 48 hour period, the reaction mixture was concentrated by ultrifiltration (MWCO 5K) to 2.8 ml, then buffer exchanged with 25 mM NaOAc+0.001% Tween-80, pH 6.0) to a final volume of 3 ml. The final product was ion exchange purified on SP (5 mL) three times (three injections, 1 ml each). PEGylated EPO (Peak 2) was collected and concentrated by ultrifiltration to a final volume of 2 ml for SEC purification. Purification on superdex 200 provided resolution of the desired protein: EPO-GlcNAc-Gal-SA-PEG (40K) for the final step of the reaction.

10.3 Complete Terminal Sialylation of CHO-EPO-GalNAc-Gal-SA-PEG(40K)

In this step of the process sialic acid was added to the termini of glycosyl structures not bearing a modified sialic acid residue.

Figure 4A:
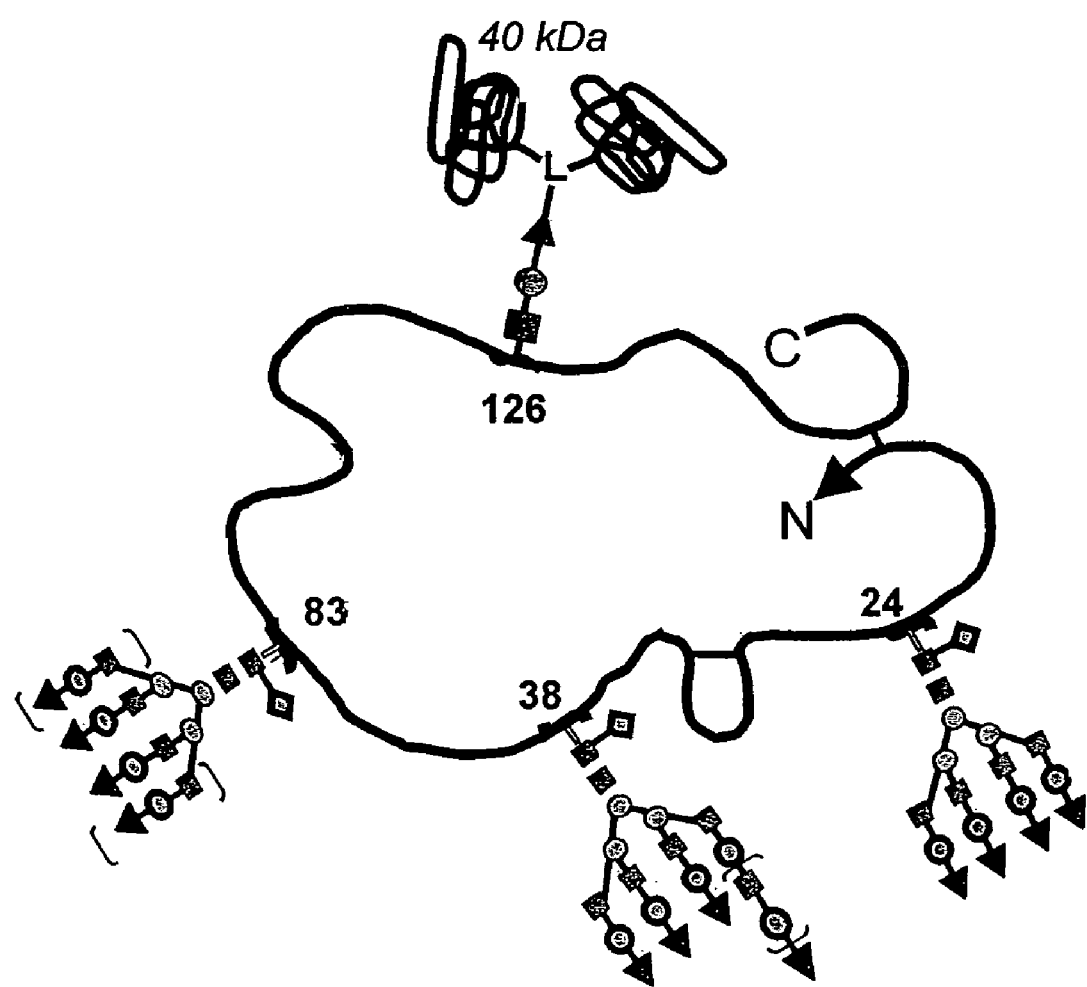
FIG. 4.

Combined PEGylated EPO (approximately 2 mg from the reaction in step, b above) was concentrated by ultrafiltration (MWCO 5K) and then buffer exchanged with tris buffer (0.05M Tris, 0.15 M NaCl, 0.001 M $CaCl_2$+0.005% $NaN_3$) to a final volume of 2 mL. Then CMP-N-acetyl neuraminic acid (CMP-NANA; 1.5 mg, 2.4 μmol), ST3GalIII (8.9 U/mL, 10 μl, 0.089 U) and 50 μl of 100 mM $MnCl_2$ were added. The resulting mixture was rocked at 32° C. for 24 h, then concentrated to 1 ml final volume. This solution was directly subjected to Superdex 200 purification using 1×PBS (pH 5.5+ 0.005% Tween 80) as eluent. Peak 1 was collected and diluted to 10 ml. Protein concentration 52.8 ug/ml (BCA). A total of 528 µg protein was obtained. A schematic representation of the final peptide product is shown in FIG. 4A.

Example 11

Figure 5:
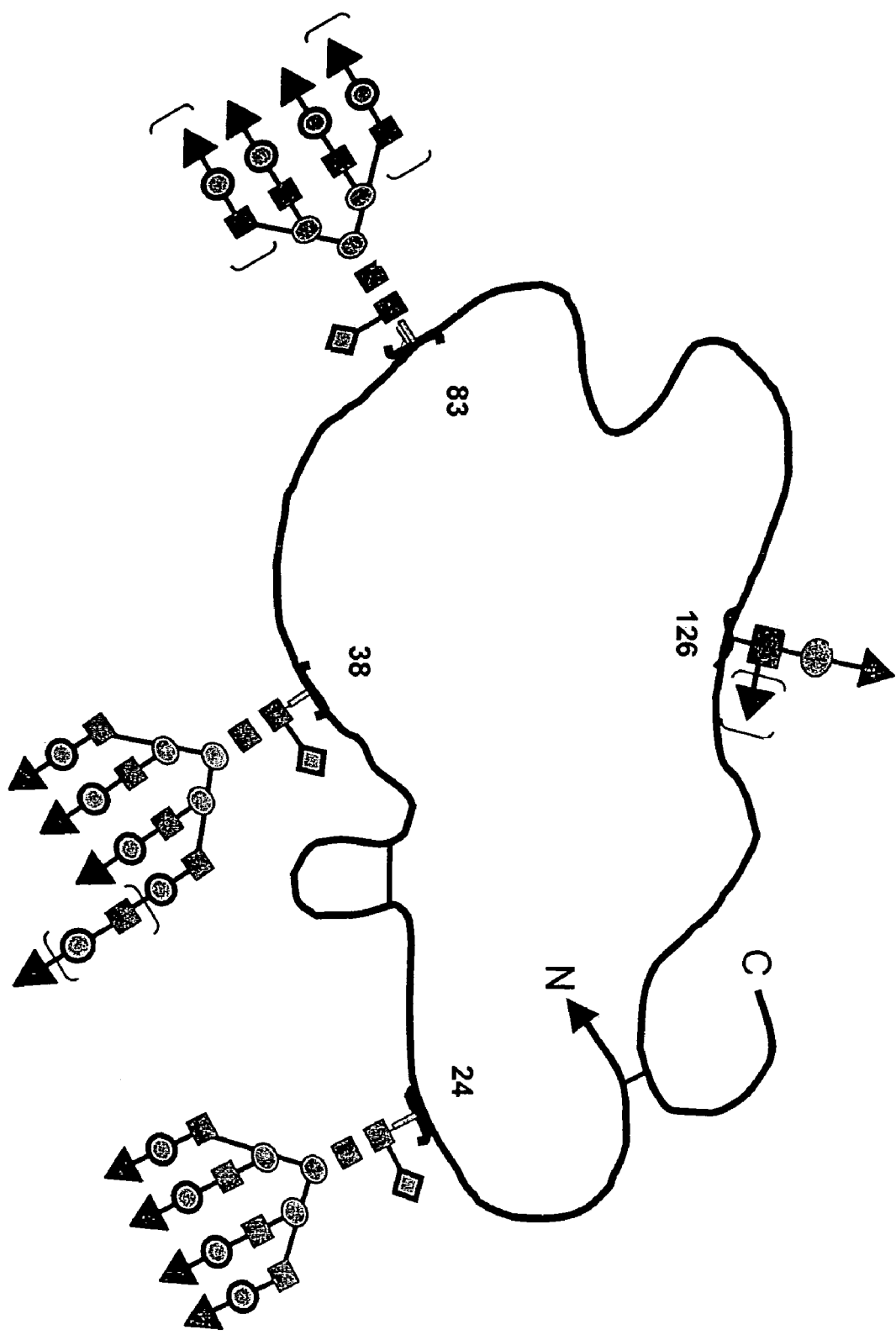
FIG. 5.

In this example the pharmacokinetic profiles of intravenously-administered CHO-derived EPO (a schematic representation is shown in FIG. 5) and glycopegylated variants of the CHO-derived EPO were compared using an ELISA assay.

Figure 4B:
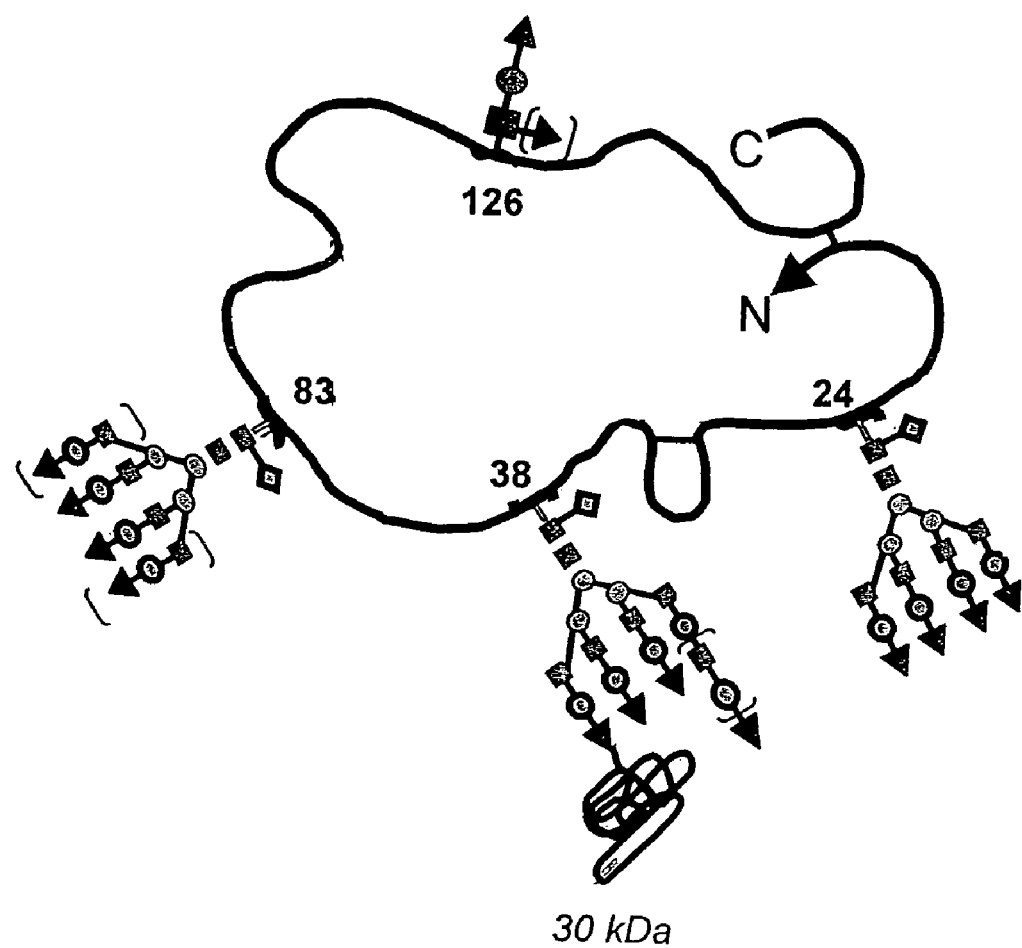

The pharmacokinetics of two non-PEGylated batches of CHO-derived Erythropoietin, a 30K PEGylated CHO-derived Erythropoietin (FIG. 4B) produced by methods of the invention, and 40K PEGylated CHO-derived Erythropoietin (FIG. 4A) produced by methods of the invention, were compared by ELISA after a single 30 µg/kg intravenous dose into rats.

11.1 Preparing the ELISA Plate.

A capture antibody against human EPO was dispensed into all wells of a 96-well plate at a 100 µL per well. The plate was covered with plate seal tape and incubated for 2 hours at 37° C. The Capture antibody was removed from the plate by washing 2 times with Tris-buffered saline containing 0.2% Tween-20 (TBST). After a third wash, a 3% milk blocking solution (TBST plus 3% milk) was added to the plate, the plate was covered with plate seal tape and incubated overnight at 4° C.

In the morning the blocking solution was removed by washing 3 times with TBST. The rat plasma samples and standard proteins were appropriately diluted with rat plasma and dispensed into the wells at 100 µL/well. The plate was covered with plate seal tape and incubated overnight at 4° C.

The next morning standard proteins were used to generate a standard linear regression for each of the EPO proteins whose pharmacokinetic properties were tested. A reverse phase-HPLC analysis of the standard proteins was completed and the concentrations were determined by calculating the area under the peak(s) corresponding to the protein detected.

11.2 Preparing and Adding the Test Samples.

Each test sample was diluted and the diluted samples were dispensed into an ELISA plate at 100 µL/well. The plate was then covered with plate seal tape and incubated overnight at 4° C.

11.3 Measuring the Europium Counts.

In the morning the rat serum samples were removed and the plates were washed 3 times with TBST. The detection antibody, mouse anti-human EPO which was previously labeled with Europium and purified through a gel filtration column, was applied to the ELISA plates. The plates are incubated at room temperature for 1 hour under 100 rpm agitation.

The detection antibody was removed by washing the plates 6 times with TBST. Enhancement solution was added to the plates at 200 µL/well and the plates were incubated at room temperature for 20 minutes. The fluorescence was read with a Wallac plate reader using a Europium counting program.

11.4 Results 11.4a Generating the Standard Linear Regression

The Europium counts from the standard proteins from each plate were used to generate a standard linear regression curve and equation. The Equation was used to convert the Europium count into the equivalent EPO quantity for each sample well.

11.4b Pharmacokinetic Results

Figure 6:
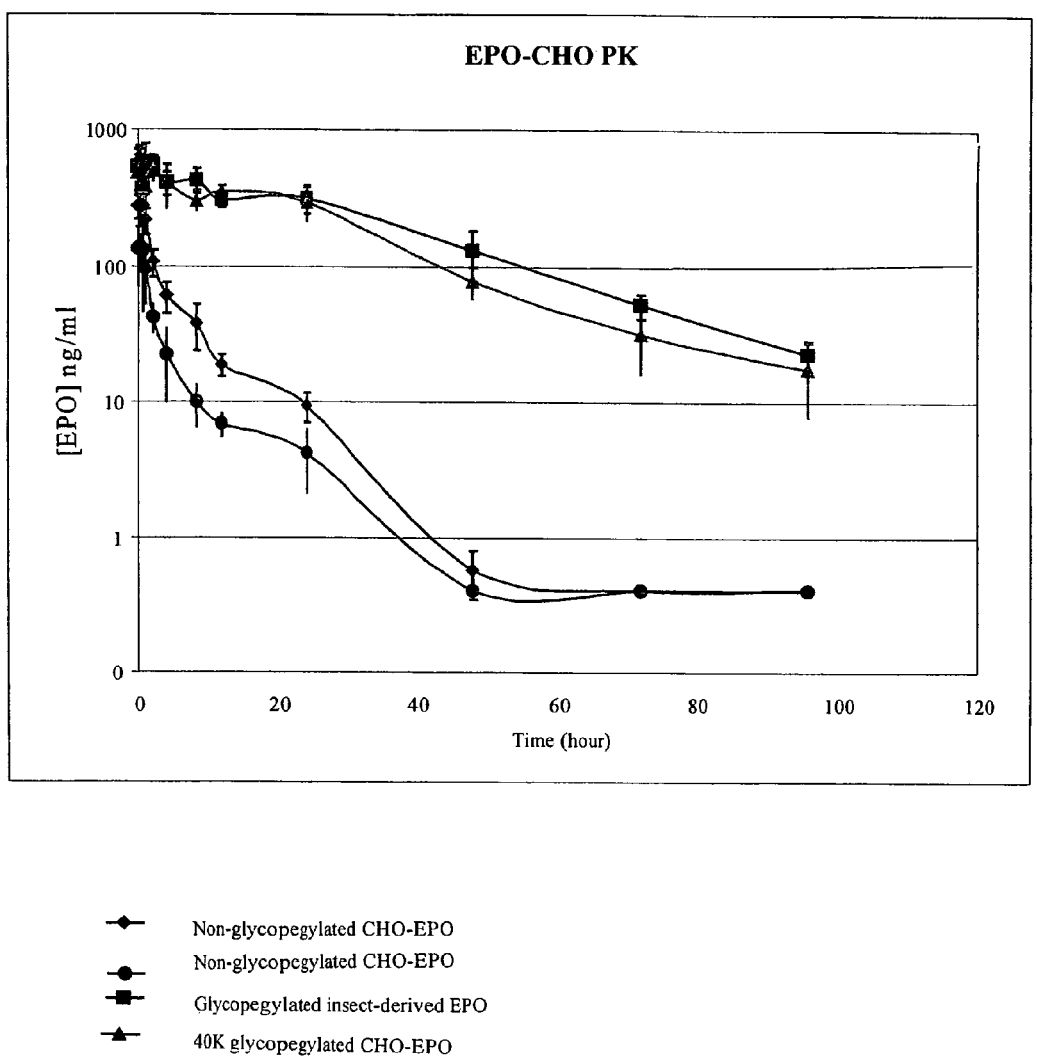
FIG. 6.

The Results are shown in FIG. 6. The limit of detection is approximately 0.4 ng/mL for non-PEGylated EPO, and approximately 0.8 ng/mL for both 30 kilodalton and 40 kilodalton PEGylated EPO.

The 30 kilodalton PEGylated CHO-derived EPO, and 40 kilodalton PEGylated CHO-derived EPO, clearly display far superior intravenous clearance parameters relative to their non-PEGylated counterparts. As can be seen in the Figure, the various EPO isoforms were ranked 40 kilodalton PEGylated CHO-derived EPO~30 kilodalton PEGylated CHO-derived EPO>>>non-PEGylated counterparts.

Example 12

In this example the pharmacokinetic profiles of subcutaneously-administered CHO-derived Erythropoietin (EPO), a hyperglycosylated non-glycopegylated EPO, an insect cell grown glycopegylated EPO, and a CHO cell derived glycopegylated EPO were determined using an ELISA assay.

Figure 7:
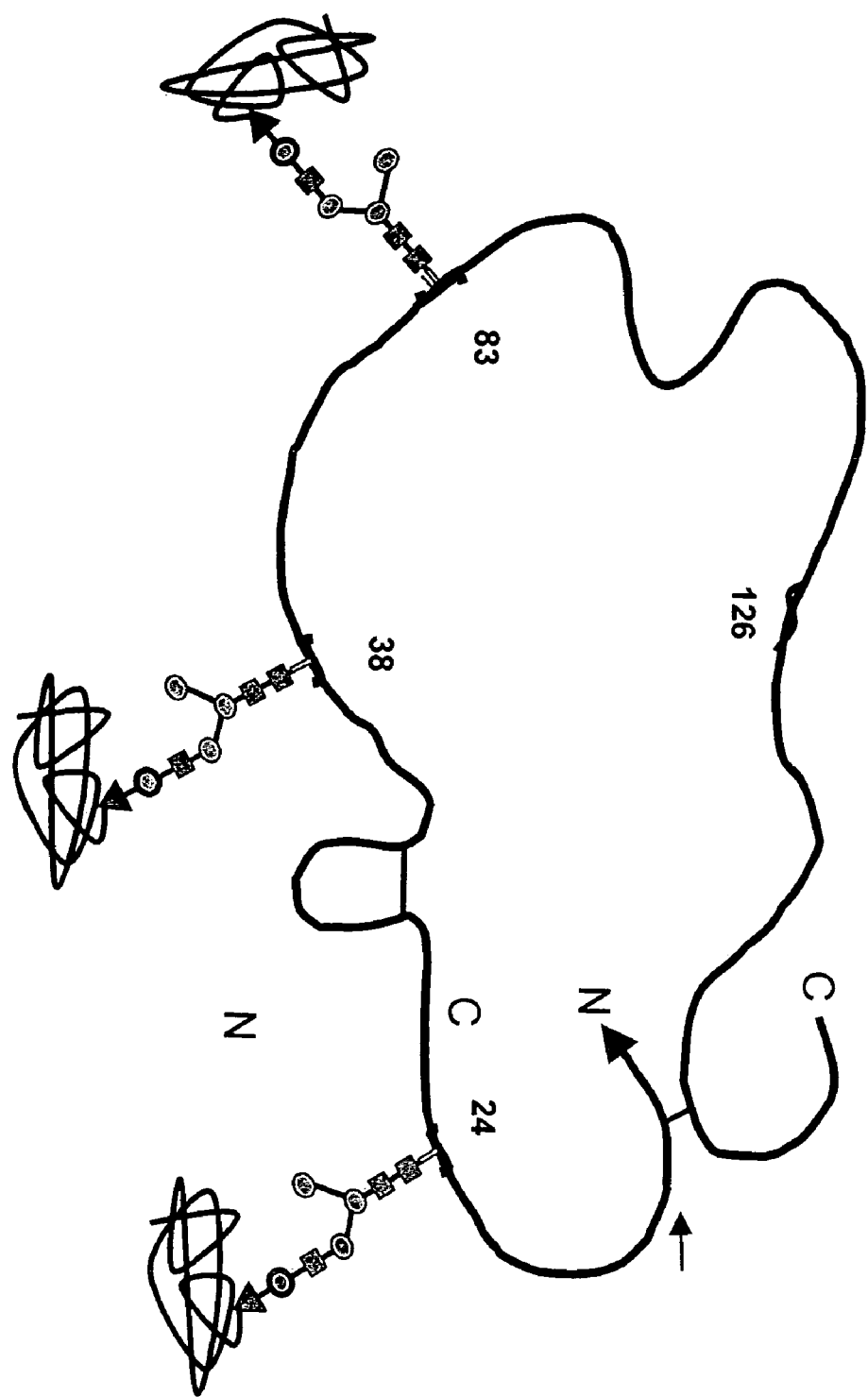
FIG. 7.

Pharmacokinetics of a non-glycopegylated CHO-derived EPO, a non-PEGylated hyperglycosylated CHO derived EPO, a glycoPEGylated insect cell derived EPO; a 10K N-linked PEGylated insect cell-derived Erythropoietin (a schematic representation is shown in FIG. 7), and 40 kilodalton O-linked PEGylated CHO-derived Erythropoietin (see FIG. 4A) were compared by ELISA after rats were given a single 10 µg/kg subcutaneous dose.

The ELISA plates were prepared and blocked as described in Example 10. Standard proteins were also prepared and Europium counts were also determined as described above.

12.1 Preparing and Adding the Rat Samples.

Following the subcutaneous (S.C.) injections the amount of EPO in the circulation was reduced as compared to that seen in equivalent I.V. injections. Plasma concentrations of the S.C. injected EPO proteins were typically detected between 30 minutes to 48 hours after injection.

12.2 Pharmacokinetic Results.

Figure 8:
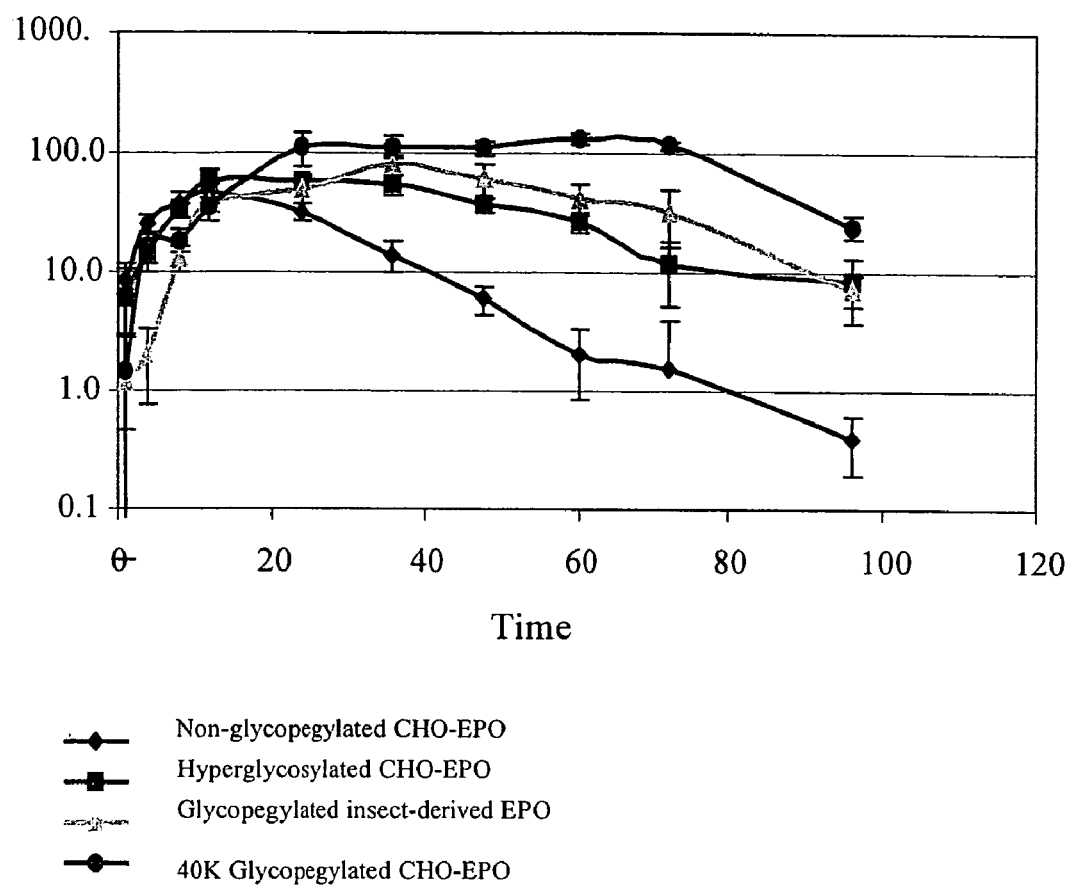
FIG. 8.
Figure 9:
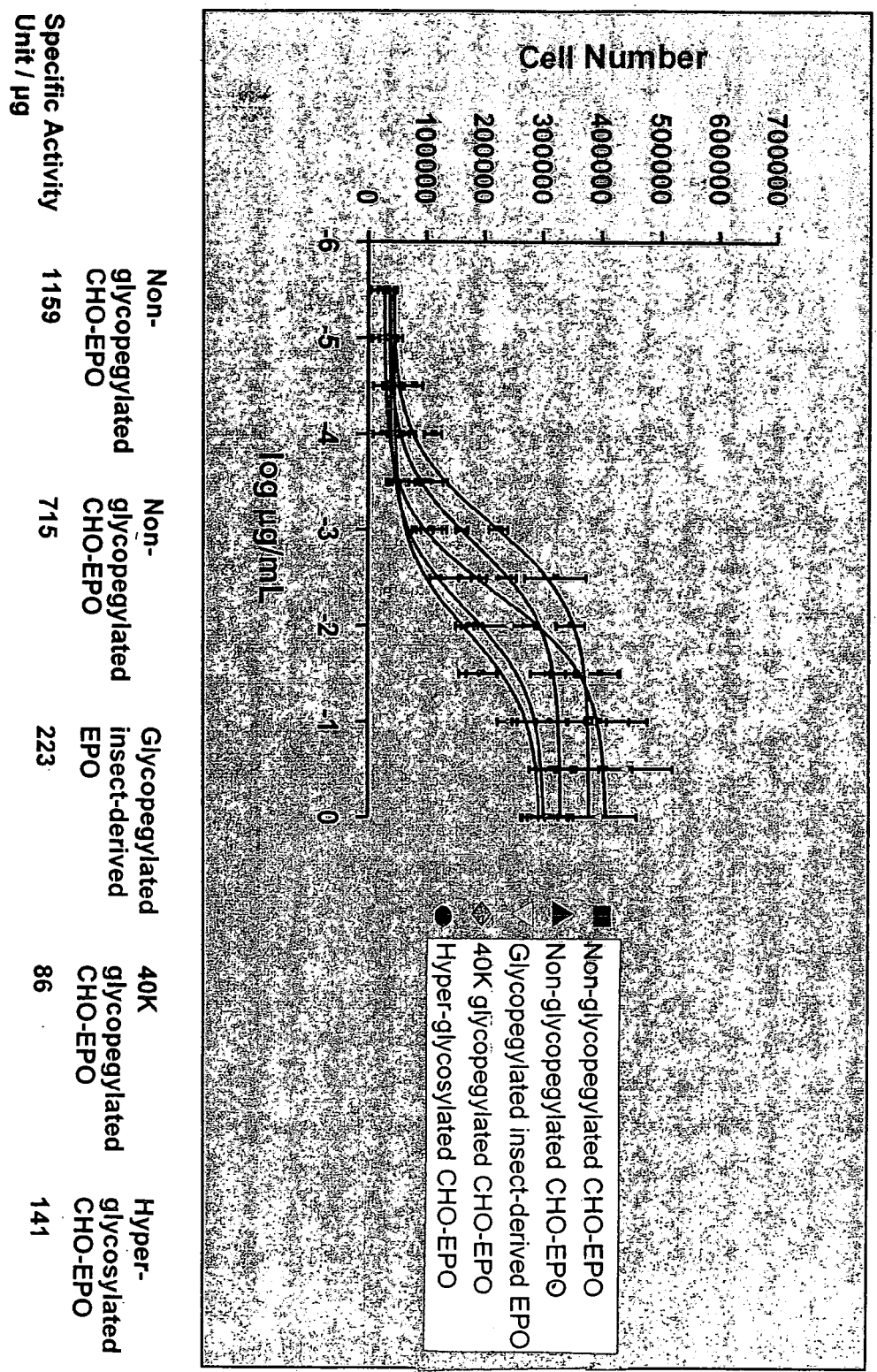
FIG. 9.
Figure 10:
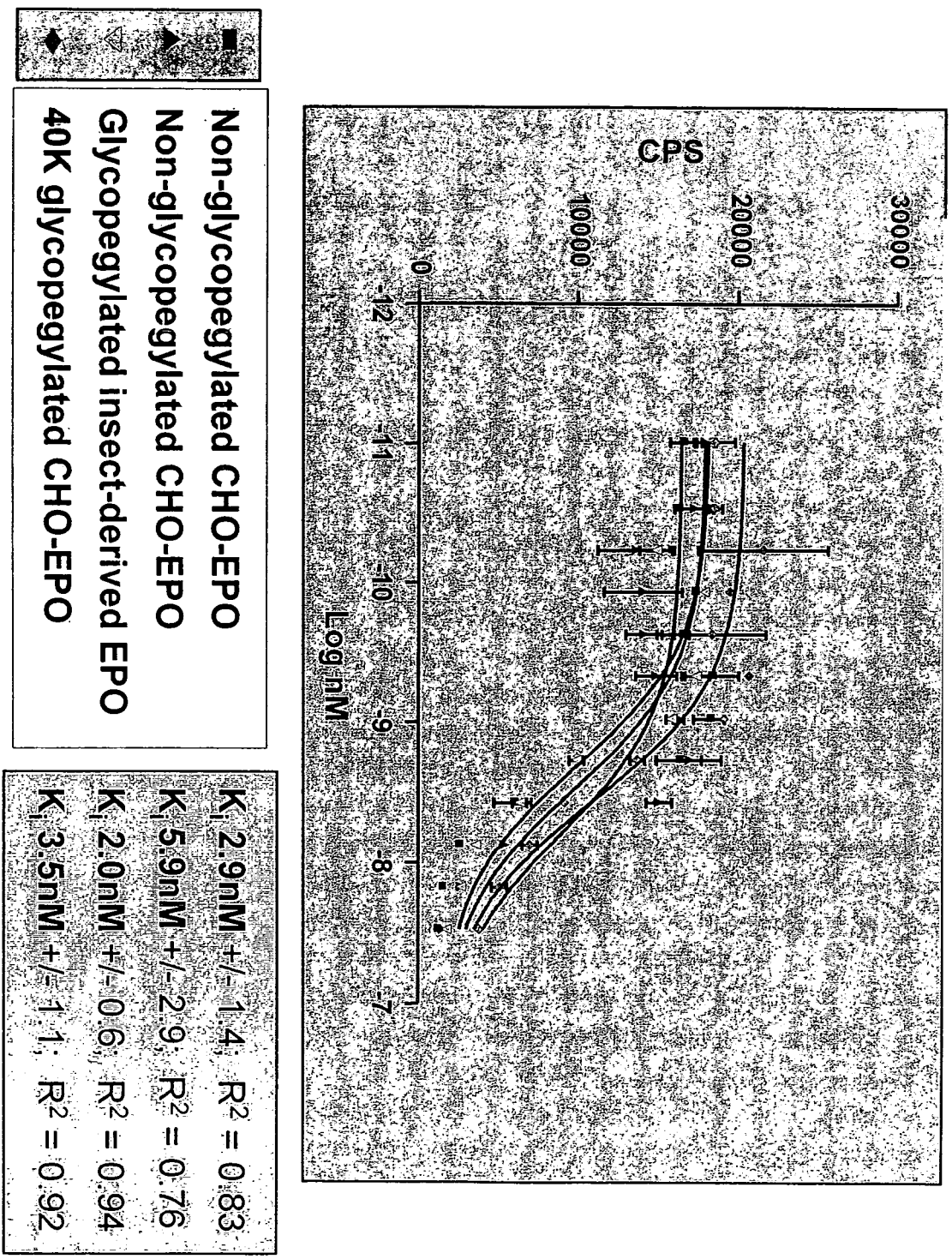
FIG. 10.

Reults of these experiments are shown in FIG. 8. FIG. 8 shows the average quantity of EPO in ng/mL and the standard deviations in the rat serum samples at different time points after injection$_{time=0\ hour}$ for each EPO variant group. The limit of detection is approximately 0.3 ng/mL for non-PEGylated EPO and PEGylated EPO.

In the case of the 10K PEGylated EPO grown in insect cells and the 40 kilodalton PEGylated CHO-EPO, the absorption appears to be gradual, creating a situation where much of these EPO variants remain to be absorbed well beyond the peak serum levels ($C_{max}$).

The 10K PEGylated EPO variant grown in insect cells attains $C_{max}$ a time range of 24-36 hours after injection. Whereas the 40 kilodalton PEGylated CHO-EPO variant attains $C_{max}$ at 40-60 hours post injection. In addition, appreciable levels of the pegylated variants were present at 96 hours after injection with the current injected dose.

The serum rank order $t_{1/2}$ is as follows: 40 kilodalton PEGylated CHO-EPO>10K PEGylated EPO variant grown in insect cells>hyperglycosylated CHO-EPO>>non-pegylated CHO-EPO.

Example 13

The relative activites of two non-pegylated EPO variants (A and B) were compared to two glycoPEGylated varinats (30 kilodalton and 40 kilodalton PEG) and to a hyperglycosylated PEG in stimulating proliferation of EPO receptor-bearing TF1 cells in culture. The activities of the glycopegylated EPO peptides in this assay are similar to the hyperglycosylated EPO variant.

Example 14

Inhibition of binding of isotope-labeled EPO to a recombinant chimeric EPO receptor by various concentrations of unpegylated EPO (A and B) and glycoPEGylated 30 kilodalton and 40 kilodalton PEG variants. Receptor affinities (Ki) are similar for unpegylated EPO and the glycoPEGylated variants.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An erythropoietin peptide conjugate comprising a sialic acid moiety having the formula:

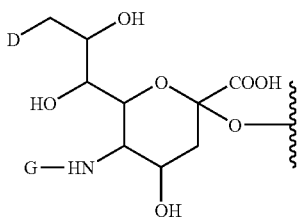

wherein

D is a member selected from —OH and $R^1$-L-HN—;

G is a member selected from $R^1$-L- and —C(O)($C_1$-$C_6$) alkyl;

$R^1$ is a moiety comprising a branched poly(ethylene glycol) residue; and

L is a linker which is a member selected from a bond, substituted or unsubstituted alkyl and substituted or unsubstituted heteroalkyl, such that when D is OH, G is $R^1$-L-, and when G is —C(O)($C_1$-$C_6$)alkyl, D is $R^1$-L-NH—, wherein said branched poly(ethylene glycol) residue has a formula which is a member selected from:

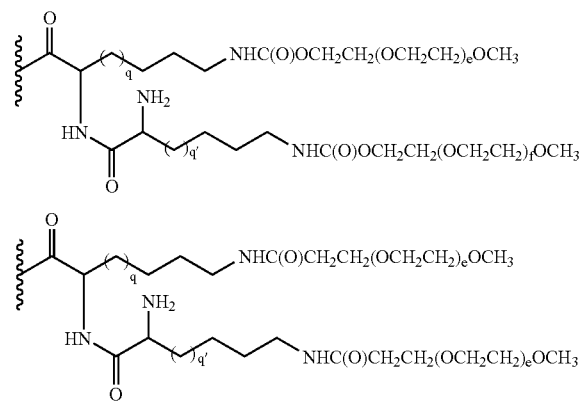

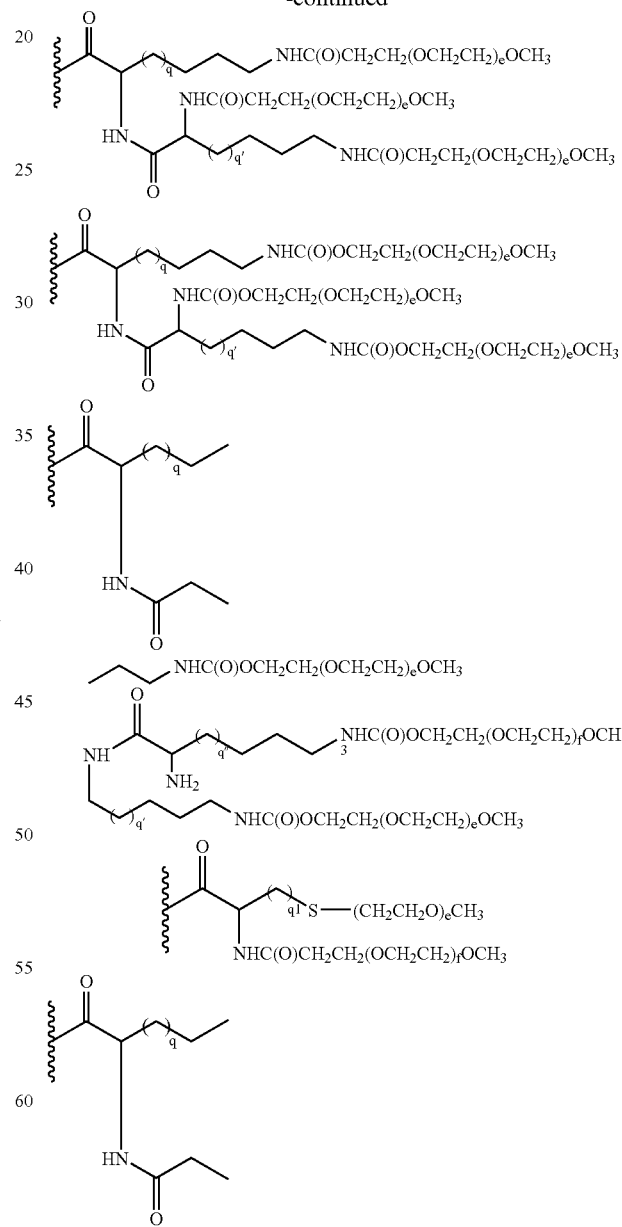

-continued

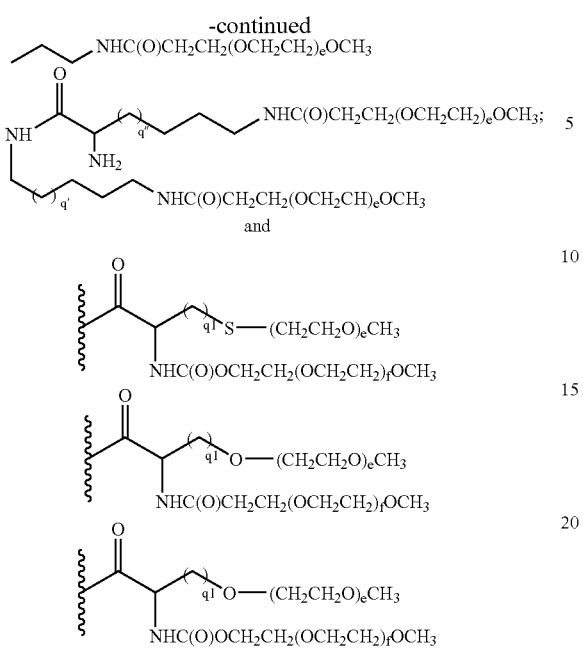

wherein
q1 is an integer from 0 to 20;
q, q' and q" are integers independently selected from from 1 to 20; and
e, f and f' are integers independently selected 1 to 2500.

2. The peptide conjugate according to claim 1, wherein $R^1$-L- has the formula:

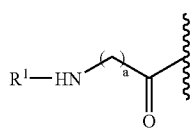

wherein
a is an integer from 0 to 20.

3. The peptide conjugate according to claim 1, wherein said sialic acid moiety has the formula:

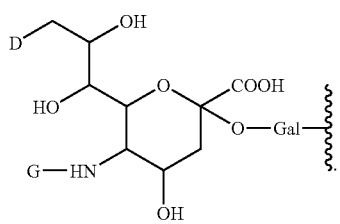

4. The peptide conjugate according to claim 1, wherein said sialic acid moiety has the formula:

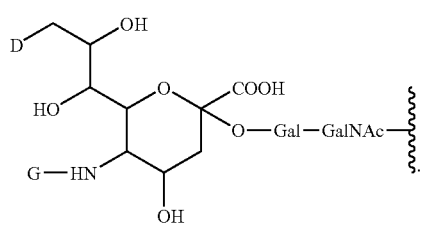

5. The peptide conjugate according to claim 1, wherein said sialic acid moiety has the formula:

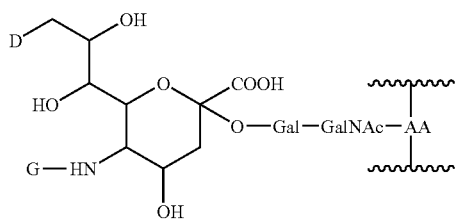

wherein AA is an amino acid residue of said peptide.

6. The peptide conjugate according to claim 5, wherein said amino acid residue is a member selected from serine and threonine.

7. The peptide conjugate according to claim 6, wherein said peptide has the amino acid sequence of SEQ ID NO:1.

8. The peptide conjugate according to claim 7, wherein said amino acid residue is a serine at position 126 of SEQ ID NO:1.

9. The peptide conjugate according to claim 1, wherein said sialic acid moiety has a formula selected from:

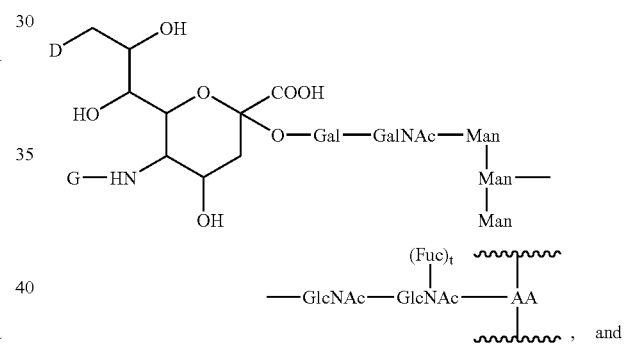

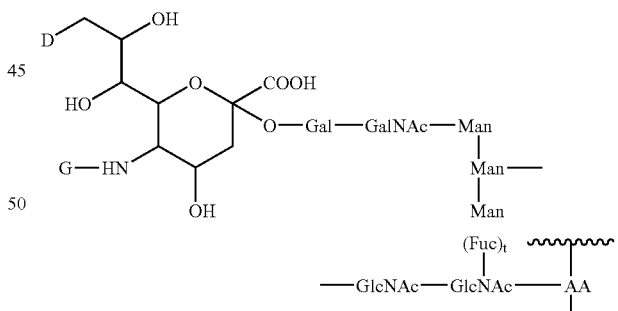

wherein AA is an amino acid residue of said peptide; and t is an integer equal to 0 or 1.

10. The peptide conjugate according to claim 9, wherein said amino acid residue is an asparagine residue.

11. The peptide conjugate according to claim 10, wherein said peptide has the amino acid sequence of SEQ ID NO:1, and wherein said amino acid residue is an asparagine residue which is a member selected from N24, N38, N83, and combinations thereof.

12. The peptide conjugate according to claim 1, wherein said sialic acid moiety has the formula:

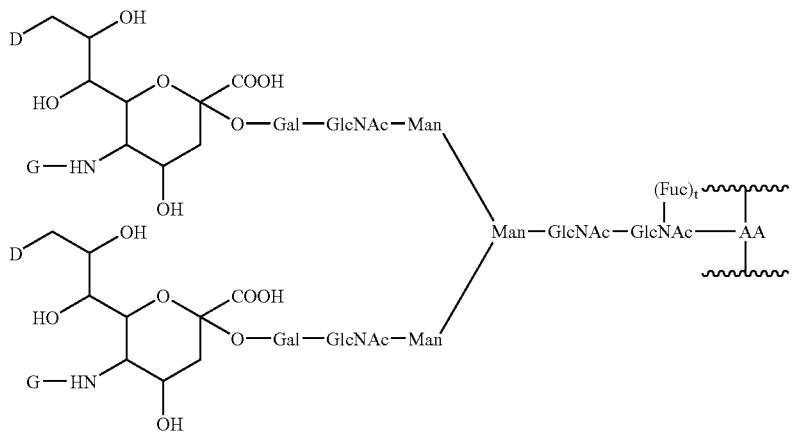

wherein AA is an amino acid residue of said peptide; and t is an integer equal to 0 or 1.

13. The peptide conjugate according to claim 12, wherein said amino acid residue is an asparagine residue.

14. The peptide conjugate according to claim 13, wherein said peptide has the amino acid sequence of SEQ ID NO:1, and wherein said amino acid residue is an asparagine residue which is a member selected from N24, N38, N83, and combinations thereof.

15. The peptide conjugate according to claim 1, wherein said amino acid residue is an asparagine residue.

16. The peptide conjugate according to claim 15, wherein said peptide has the amino acid sequence of SEQ ID NO:1, and wherein said amino acid residue is an asparagine residue which is a member selected from N24, N38, N83, and combinations thereof.

17. The peptide conjugate according to claim 1, wherein said peptide is a bioactive erythropoietin peptide.

18. The peptide conjugate according to claim 17, wherein said peptide is erythropoietically active.

19. The peptide conjugate according to claim 18, wherein said peptide is essentially non-erythropoietically active.

20. The peptide conjugate according to claim 19, wherein said peptide is tissue protective.

21. A method of making a PEG-ylated erythropoietin comprising the moiety:

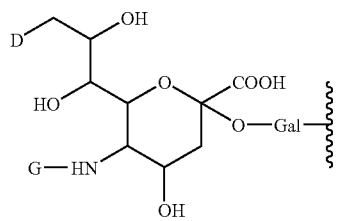

wherein
D is a member selected from -OH and $R^1$-L-NH-;
G is a member selected from $R^1$-L- and -C(O)($C_1$-$C_6$)alkyl;
$R^1$ is a moiety comprising a straight-chain or branched poly(ethylene glycol) residue; and L is a linker which is a member selected from a bond, substituted or unsubstituted alkyl and substituted or unsubstituted heteroalkyl, such that when D is OH, G is $R^1$-L-, and when G is -C(O)($C_1$-$C_6$)alkyl, D is $R^1$-L-NH-, said method comprising:
(a) contacting a substrate erythropoietin peptide comprising the glycosyl moiety:

with a PEG-sialic acid donor moiety having the formula:

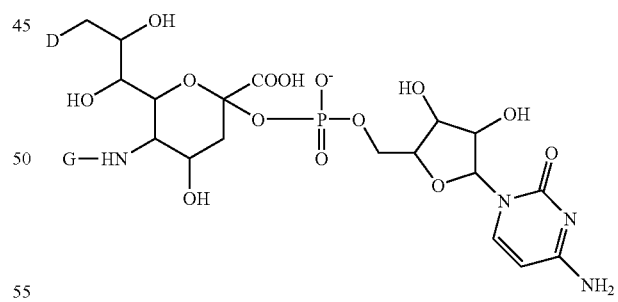

and an enzyme that transfers said PEG-sialic acid onto the Gal of said glycosyl moiety, under conditions appropriate to for said transfer.

22. The method of claim 21, further comprising, prior to step (a):
(b) expressing said substrate erythropoietin peptide in a suitable host.

23. The method of claim 22, wherein said host is selected from an insect cell and a mammalian cell.

24. The method of claim 23, wherein said insect cell is a *Spodoptera frugiperda* cell line.

25. A method of enhancing red blood cell production in a mammal, said method comprising administering to said mammal an peptide conjugate according to claim 1.

26. A pharmaceutical formulation comprising the erythropoietin peptide conjugate according to claim 1, and a pharmaceutically acceptable carrier.

27. The erythropoietin peptide according to claim 1, wherein said poly(ethylene glycol) residue has a molecular weight that is essentially homodisperse.

28. The erythropoietin peptide of claim 1, wherein said branched poly(ethylcne glycol) residue comprises monomethoxy-poly(ethylene glycol).

29. The method according to claim 28, wherein said poly (ethylene glycol) residue has a molecular weight that is essentially homodisperse.

30. The method according to claim 28, wherein said branched poly(ethylene glycol) residue comprises monomethoxy-poly(ethylene glycol).

31. The peptide of claim 1, wherein said sialic acid moiety has a formula selected from:

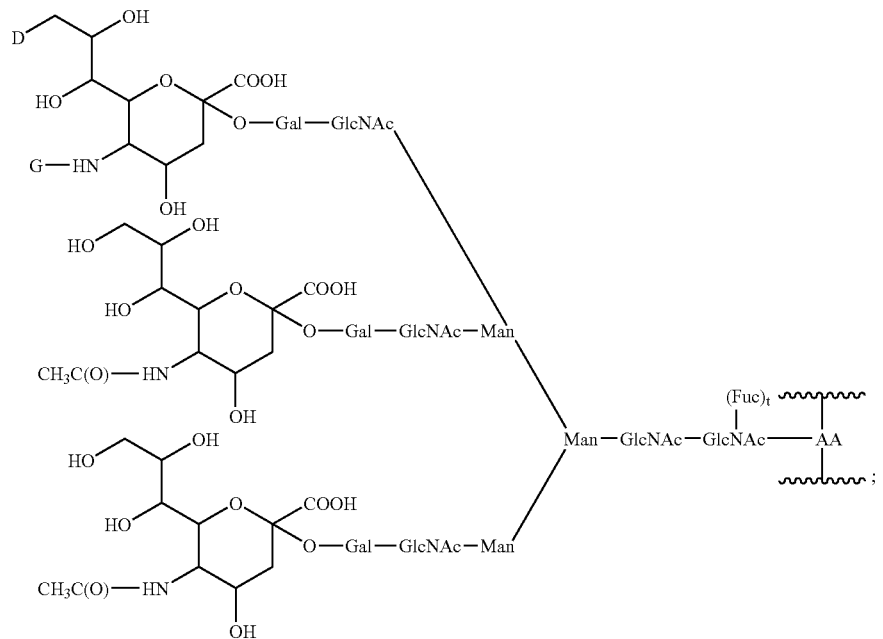

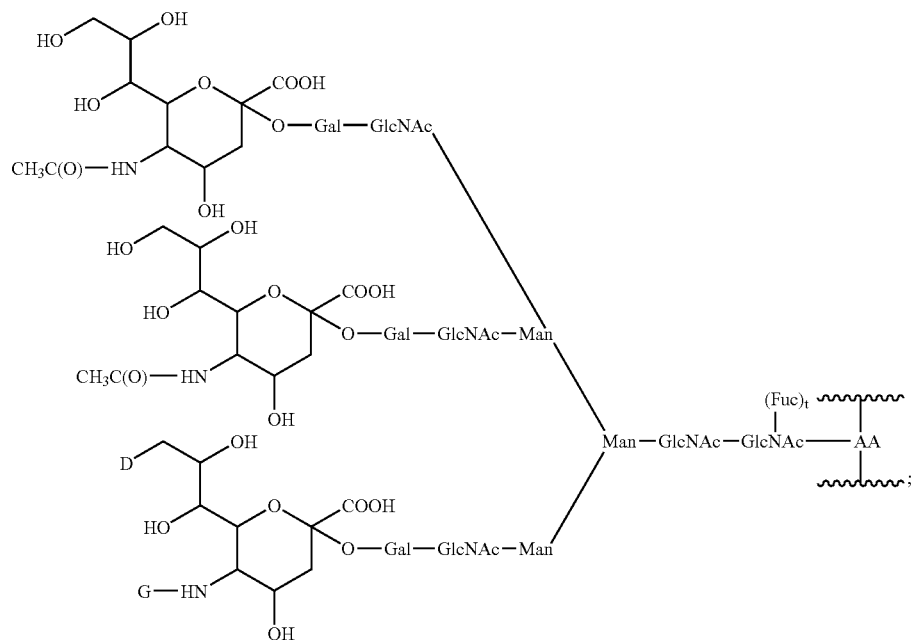

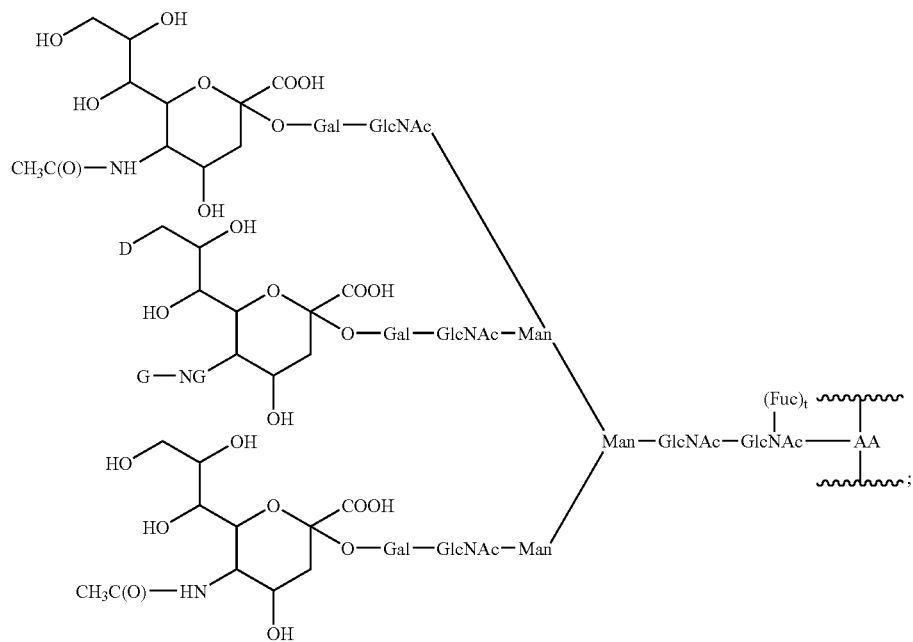
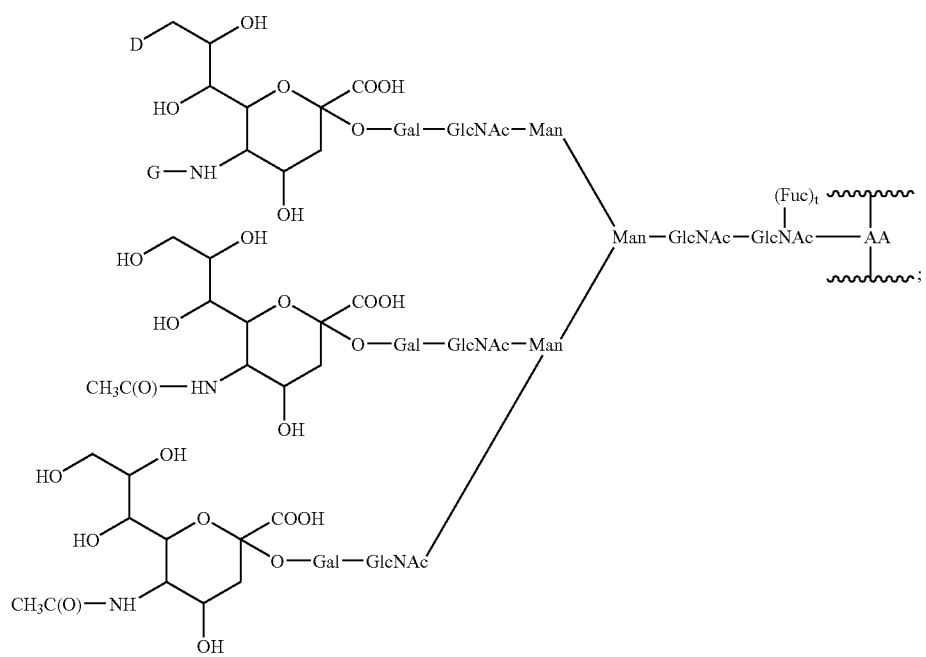

-continued
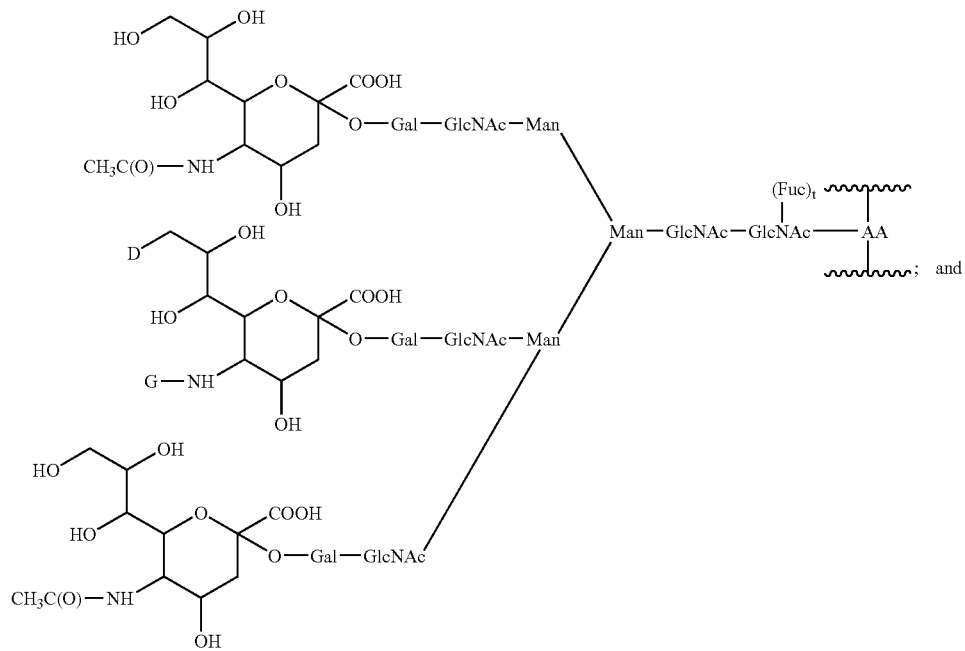
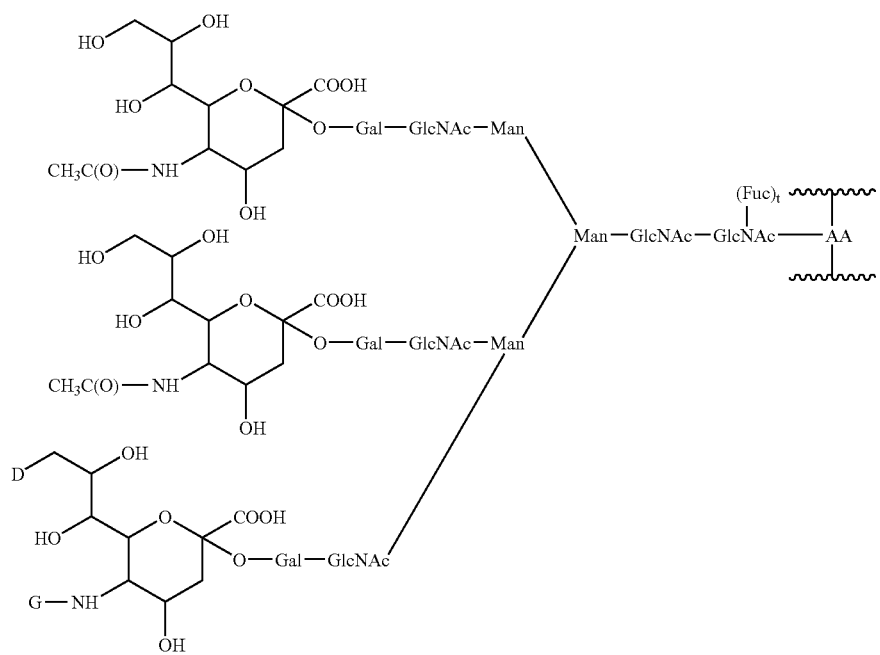
wherein AA is an amino acid residue of said peptide; and t is an integer equal to 0 or 1.

32. The peptide according to claim 1, wherein said sialic acid moiety has a formula selected from:
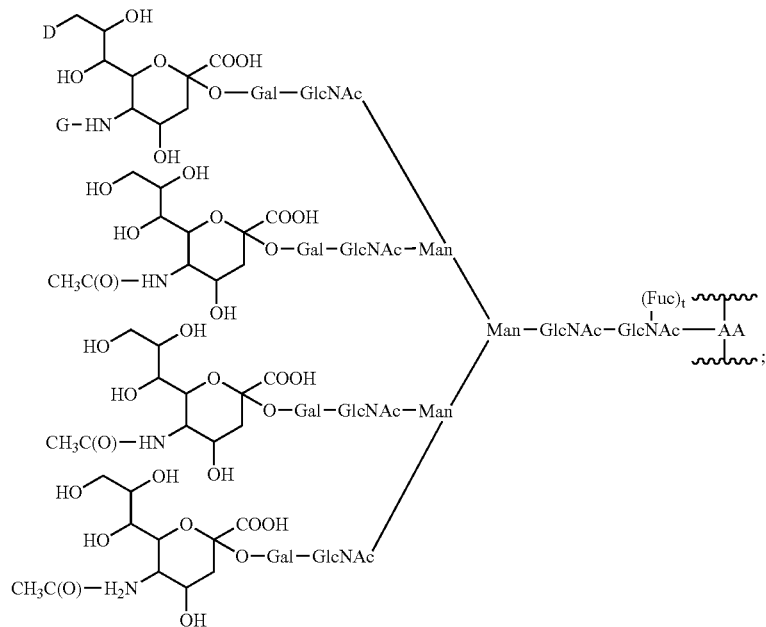
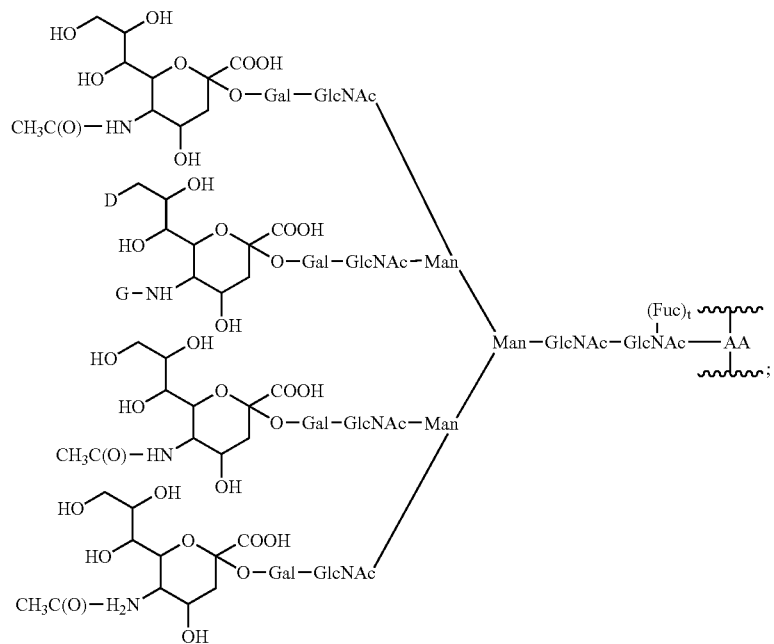

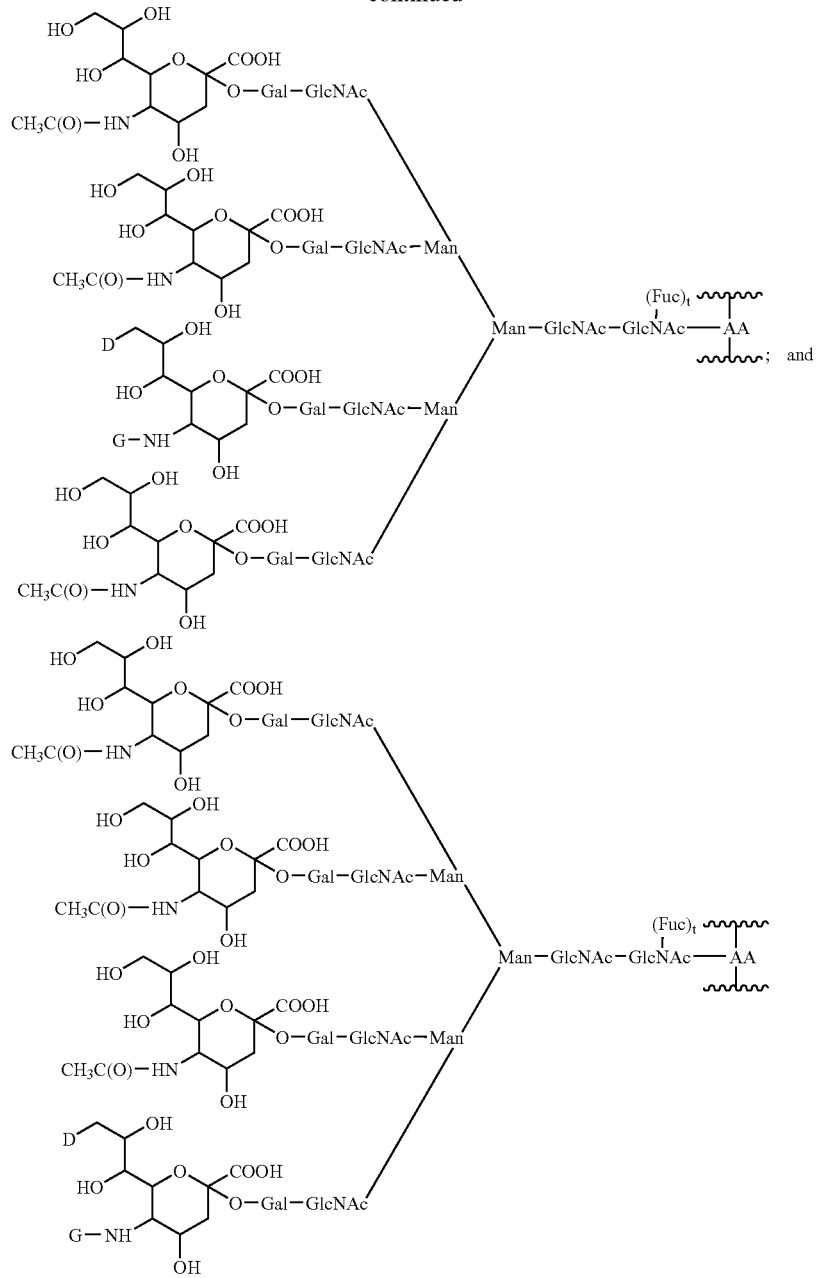

wherein AA is an amino acid residue of said peptide; and t is an integer equal to 0 or 1.

33. The peptide conjugate according to claim 1, wherein said sialic acid moiety is conjugated to a precursor erythropoietin peptide by action of a sialyltransferase.

34. The peptide conjugate according to claim 33, wherein said sialyltransferase is CST-II.

35. A method of treating anemia, anemias associated with chronic renal failure, or anemias associated with cancer chemotherapy treatment, comprising administering the peptide conjugate of claim 1 to a subject in need thereof.

36. A method of treating a tissue injury in a subject in need thereof, said injury resulting from ischemia, trauma, inflammation or contact with a toxic substance, said method comprising the step of administering to the subject an amount of an erythropoietin peptide conjugate according to claim 1, effective to ameliorate the damage associated with the tissue injury in said subject.

* * * * *

UNITED STATES PATENT AND TRADEMARK OFFICE
CERTIFICATE OF CORRECTION

PATENT NO. : 7,405,198 B2
APPLICATION NO. : 10/997405
DATED : July 29, 2008
INVENTOR(S) : Shawn DeFrees, Robert J. Bayer and David A. Zopf It is certified that error appears in the above-identified patent and that said Letters Patent is hereby corrected as shown below:

In columns 97, 98 and 99 should read:

1. An erythropoietin peptide conjugate comprising a sialic acid moiety having the formula:

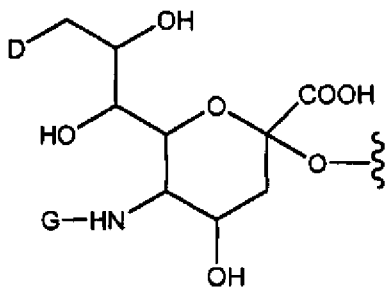

wherein

D is a member selected from -OH and $R^1$-L-HN-;

G is a member selected from $R^1$-L- and -C(O)($C_1$-$C_6$)alkyl;

$R^1$ is a moiety comprising a branched poly(ethylene glycol) residue; and

L is a linker which is a member selected from a bond, substituted or unsubstituted alkyl and substituted or unsubstituted heteroalkyl, such that when D is OH, G is $R^1$-L-, and when G is –C(O)($C_1$-$C_6$)alkyl, D is $R^1$-L-NH-, wherein said branched poly(ethylene glycol) residue has a formula which is a member selected from:

UNITED STATES PATENT AND TRADEMARK OFFICE
CERTIFICATE OF CORRECTION

PATENT NO. : 7,405,198 B2
APPLICATION NO. : 10/997405
DATED : July 29, 2008
INVENTOR(S) : Shawn DeFrees, Robert J. Bayer and David A. Zopf It is certified that error appears in the above-identified patent and that said Letters Patent is hereby corrected as shown below:

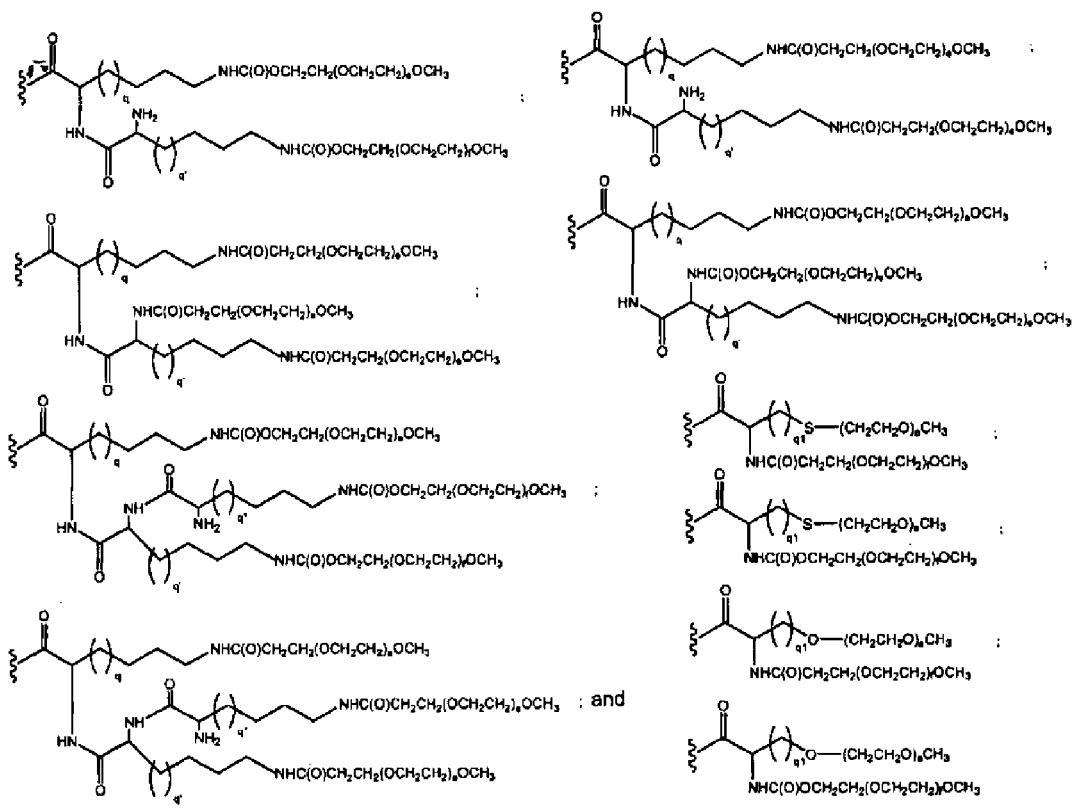

wherein q1 is an integer from 0 to 20;

q, q' and q" are integers independently selected from from 1 to 20; and e, f and f' are integers independently selected 1 to 2500.

UNITED STATES PATENT AND TRADEMARK OFFICE
CERTIFICATE OF CORRECTION

PATENT NO.           : 7,405,198 B2
APPLICATION NO. : 10/997405
DATED                    : July 29, 2008
INVENTOR(S)         : Shawn DeFrees, Robert J. Bayer and David A. Zopf It is certified that error appears in the above-identified patent and that said Letters Patent is hereby corrected as shown below:

In column 104 lines 4-6 should read:

29.  The method according to claim 21, wherein said poly(ethylene glycol) residue has a molecular weight that is essentially homodisperse.

In column 104 lines 7-9 should read:

30.  The method according to claim 21, wherein said branched poly(ethylene glycol) residue comprises monomethoxy-poly(ethylene glycol).

Signed and Sealed this

Twentieth Day of October, 2009

David J. Kappos
*Director of the United States Patent and Trademark Office*